(12) United States Patent
Uno et al.

(10) Patent No.: US 9,650,386 B2
(45) Date of Patent: May 16, 2017

(54) QUINOLINE-SUBSTITUTED COMPOUND

(71) Applicant: TAIHO PHARMACEUTICAL CO., LTD., Chiyoda-ku, Tokyo (JP)

(72) Inventors: Takao Uno, Tsukuba (JP); Katsumasa Nonoshita, Tsukuba (JP); Tadashi Shimamura, Tsukuba (JP)

(73) Assignee: Taiho Pharmaceutical Co., Inc., Tokyo (JP)

( * ) Notice: Subject to any disclaimer, the term of this patent is extended or adjusted under 35 U.S.C. 154(b) by 0 days.

(21) Appl. No.: 14/911,093

(22) PCT Filed: Aug. 22, 2014

(86) PCT No.: PCT/JP2014/071951
§ 371 (c)(1),
(2) Date: Feb. 9, 2016

(87) PCT Pub. No.: WO2015/025936
PCT Pub. Date: Feb. 26, 2015

(65) Prior Publication Data
US 2016/0194332 A1 Jul. 7, 2016

(30) Foreign Application Priority Data

Aug. 22, 2013 (JP) ................................ 2013-172746

(51) Int. Cl.
*C07D 487/14* (2006.01)
*C07D 471/14* (2006.01)

(52) U.S. Cl.
CPC ......... *C07D 487/14* (2013.01); *C07D 471/14* (2013.01)

(58) Field of Classification Search
CPC ............................ C07D 487/14; C07D 471/14
USPC .................................................... 514/214.02
See application file for complete search history.

(56) References Cited

U.S. PATENT DOCUMENTS

| | | | |
|---|---|---|---|
| 5,733,918 A | 3/1998 | Okazaki et al. | |
| 8,779,142 B2 | 7/2014 | Kitade et al. | |
| 8,889,666 B2 * | 11/2014 | Sagara ................ | C07D 487/14 514/214.02 |
| 8,912,181 B2 | 12/2014 | Kitade et al. | |
| 2014/0057899 A1 | 2/2014 | Sagara et al. | |
| 2014/0343038 A1 | 11/2014 | Sakamoto et al. | |
| 2014/0378409 A1 | 12/2014 | Fujita et al. | |

FOREIGN PATENT DOCUMENTS

| | | | |
|---|---|---|---|
| CN | 1130903 A | 9/1996 | |
| CN | 102471335 A | 5/2012 | |
| EP | 2960241 A1 | 12/2015 | |
| JP | 2008-533172 A | 8/2008 | |
| WO | 2006/102079 A1 | 9/2006 | |
| WO | 2011/046964 A2 | 4/2011 | |
| WO | 2012093708 A1 | 7/2012 | |
| WO | 2013047813 A1 | 4/2013 | |
| WO | 2013100014 A1 | 7/2013 | |
| WO | 2013/118817 A1 | 8/2013 | |
| WO | 2013/125709 A1 | 8/2013 | |
| WO | 2014/129596 A1 | 8/2014 | |

OTHER PUBLICATIONS

Lacouture, "Mechanisms of cutaneous toxicities to EGFR inhibitors", Nature Reviews Cancer, 2006, vol. 6, No. 10, pp. 803-812.
Arteaga, "The Epidermal Growth Factor Receptor: From Mutant Oncogene in Nonhuman Cancers to Therapeutic Target in Human Neoplasia", Journal of Clinical Oncology, 2001, vol. 19, No. 18s, pp. 32s-40s.
Ministry of Internal Affairs and Communications Statistics Bureau homepage / statistical data / world statistics "World Statistics 2011", p. 332 14-1.
Doebele et al., "New strategies to overcome limitations of reversible EGFR tyrosine kinase inhibitor therapy in non-small cell lung cancer", Lung Cancer, 2010, vol. 69, No. 1, pp. 1-12.
Pao et al., "Rational, biologically based treatment of EGFR-mutant non-small-cell lung cancer", Nature Reviews cancer, 2010, vol. 10, No. 11, pp. 760-774.

* cited by examiner

*Primary Examiner* — Yevegeny Valenrod
(74) *Attorney, Agent, or Firm* — Rothwell, Figg, Ernst & Manbeck, P.C.

(57) ABSTRACT

An object to be achieved by the present invention is to provide a novel compound having EGFR inhibitory effects and cell growth inhibitory effects, as well as a medication useful for the prevention and/or treatment of cancer based on the EGFR inhibitory effects.

The present invention provides a compound represented by Formula (I) below, or a salt thereof.

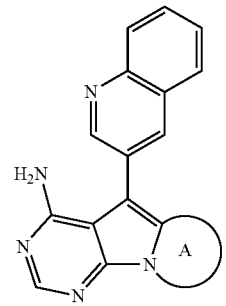

15 Claims, No Drawings

QUINOLINE-SUBSTITUTED COMPOUND

CROSS REFERENCE TO RELATED APPLICATIONS

The present application is a U.S.C. 371 National Entry Application from PCT/JP2014/071951 filed on Aug. 22, 2014 which claims priority to the specification of Japan Patent Application No. 2013-172746 (the entire disclosure is incorporated in the present specification by reference) filed on Aug. 22, 2013.

TECHNICAL FIELD

The present invention relates to quinoline-substituted compounds having an inhibitory action against Epidermal Growth Factor Receptor (EGFR), and pharmaceutical compositions containing those as an active ingredient.

BACKGROUND ART

EGFR is a receptor-type tyrosine kinase, exerts its physiological function in normal tissue when being bound to Epidermal Growth Factor (EGF), which is a ligand, and contributes to growth, apoptosis inhibition, etc., in epithelial tissues (Non-Patent Document (NPD) 1).

In addition, EGFR is one of the oncogenes, and amplification of the EGFR gene and high expression or mutation of its protein are seen in various cancer types such as head and neck cancer, breast cancer, colorectal cancer, esophagus cancer, pancreatic cancer, lung cancer, ovarian cancer, renal cancer, bladder cancer, skin cancer, and brain tumor (Non-Patent Document (NPD) 2). In Japan and western countries, approximately 170 to 375 in every 100,000 people perish due to cancer every year, and cancer ranks high as a cause of death (Non-Patent Document (NPD) 3). Among these, the death toll due to lung cancer reaches approximately 1,400,000 per year worldwide, and since non-small cell lung cancer accounts for 80% or more of lung cancers, there has been a desire for the development of an effective therapy for the same (Non-patent Document (NPD) 4).

In recent years, responsible genes for these cancers are being identified, and a mutation in the EGFR gene is also one of them and results in an active mutated EGFR protein. An active mutated EGFR protein is, for example, a deletion of amino acid at positions 746-750 (EGFR (d746-750)), a mutation of amino acid at position 858 from leucine to arginine (EGFR (L858R)), or the like. Such mutations are reported, for example, in 20-40% of non-small cell lung cancer cases in Japan, and in 10-15% of non-small cell lung cancer cases in western countries. Since non-small cell lung cancer having these mutations is highly susceptible against gefitinib (product name: Iressa (Registered trademark)) and erlotinib (product name: Tarceva (Registered trademark)) which are chemical agents (EGFR inhibitors) that inhibit the kinase activity of EGFR, these chemical agents are used as therapeutic agents in Japan and western countries. However, the cancer acquires resistance against gefitinib and erlotinib after 6 to 12 months from the beginning of use and therapeutic effect becomes weak. Therefore, this acquired resistance has been a serious problem for treating non-small cell lung cancer having a highly-susceptible mutated EGFR. It has been revealed that approximately 50% of the acquired resistance is due to emergence of a resistant mutated EGFR protein (EGFR (d746-750/T790M) or EGFR (T790M/L858R)) having a second mutation in the EGFR gene resulting in amino acid at position 790 to change from threonine to methionine. It has been an important task to develop a therapeutic agent that is effective against non-small cell lung cancer having this drug resistant mutated EGFR (Non-patent Document (NPD) 5).

On the other hand, skin abnormality and alimentary canal disorder are reported as common side effects of the EGFR inhibitors of gefitinib and erlotinib, which are clinically used as therapeutic agents at present, and of EGFR inhibitors such as BIBW2992 etc., which are under clinical trial. It is widely thought that these side effects are caused by the EGFR inhibitors inhibiting the activity of not only a mutated EGFR expressed in non-small cell lung cancer, but also the activity of the wild-type EGFR (EGFR (WT)) expressed in the skin or alimentary canal (Non-Patent Document (NPD) 1). From a standpoint of side effect reduction, it is considered to be preferable to have a weak inhibitory activity against EGFR (WT) in normal tissues.

Thus, there is expectation of possibly suppressing growth of non-small cell lung cancer cells having a drug resistant mutated EGFR through administration of a chemical agent having weaker inhibitory activity against the wild-type EGFR when compared to inhibitory activity against the drug resistant mutated EGFR whose amino acid at position 790 has mutated to methionine, at an administration dose where the side effect to the skin or alimentary canal does not appear strongly. This is predicted to contribute to treating the cancer, and prolonging life and improving QOL of patients. In addition, if the chemical agent has weak inhibitory activity against the wild-type EGFR but has strong in inhibitory activity not only against drug resistant mutated EGFR but also against highly-susceptible mutated EGFRs such as the EGFR (d746-750) and the EGFR (L858R) etc., which are highly susceptible against gefitinib and erlotinib; there is expectation of possibly suppressing growth of non-small cell lung cancer cells expressing a highly-susceptible mutated EGFR or a drug resistant mutated EGFR at an administration dose where the side effect to the skin or alimentary canal does not appear strongly, or expectation of possibly reducing the frequency of drug resistant mutated EGFR that emerges, as acquired resistance, from non-small cell lung cancer expressing a highly-susceptible mutated EGFR. This is predicted to contribute to treating the cancer, and prolonging life and improving QOL of patients. Furthermore, since expressions of highly-susceptible mutated EGFR and drug resistant mutated EGFR can be used in the actual scene of therapy as indices for stratification to enable selection of patients, they contribute greatly from an ethical viewpoint.

As a compound having a structure analogous to a compound according to present invention, N-(3-(4-amino-6,7,8,9-tetrahydropyrimido[5,4-b]indolizin-5-yl)phenyl)benzamide derivative is known (Patent Document (PTD) 1). Although Patent Document 1 describes using the amide compound for treating diseases characterized by B-RAF kinase, the document does not disclose specific tests and results therefrom corroborating a kinase inhibiting activity, and such activity is not confirmed.

CITATION LIST

Patent Documents

PTD 1: International Publication No. WO2006/102079 pamphlet

Non-Patent Documents

NPD 1: Nature Rev. Cancer, vol. 6, pp803-811 (2006)
NPD 2: J. Clin. Oncol., vol. 19, 32s-40s (2001)

NPD 3: Ministry of Internal Affairs and Communications Statistics Bureau homepage/statistical data/world statistics "World Statistics 2011"

NPD 4: Lung Cancer, vol. 69, pp1-12 (2010)

NPD 5: Nature Rev. Cancer, vol. 10, pp760-774 (2010)

SUMMARY OF INVENTION

Technical Problem

As described above, EGFR inhibitors, although expected to be effective in cancer therapy, are currently not clinically effective enough.

Therefore, an object of the present invention is to provide a novel compound that strongly inhibits EGFR or a salt thereof. A further object of the present invention is to provide: a novel compound that inhibits mutated EGFR, for example, EGFR (d746-750), EGFR (L858R), EGFR (d746-750/T790M), and EGFR (T790M/L858R), but that does not inhibit EGFR (WT); or a salt thereof.

Solution to Problem

The present inventors have conducted thorough research in order to achieve the above-described object. As a result, they have found that a group of quinoline-substituted compounds of the present invention have excellent inhibitory activity against EGFR and have cancer-cell-growth inhibitory action, and are useful as medication for treating cancer. The present inventors thereby achieved the present invention.

Thus, the present invention provides the following items.

Item 1. A compound represented by Formula (I) below or a salt thereof:

(I)

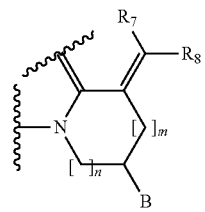

wherein the group:

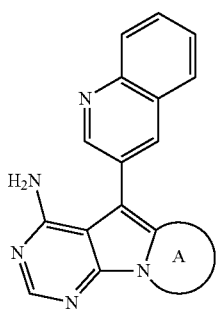

is (1) a group represented by Formula A1:

A1

(in Formula A1, B is a group represented by:

[$R_1$ is a hydrogen atom or a C1-C6 alkyl group; and $R_2$ is a group represented by:

wherein $R_3$, $R_4$, and $R_5$ are the same or different, and each represents a hydrogen atom, a halogen atom, a C1-C6 alkyl group, a C6-C12 aryl group, a C4-C9 heteroaryl group, an aminomethyl group that may be substituted with a C1-C6 alkyl group, or a 1-piperidinomethyl group, or a group represented by:

wherein $R_6$ represents a hydrogen atom or a C1-C6 alkyl group], $R_7$ and $R_8$ are the same or different, and each represents a hydrogen atom or a C1-C6 alkyl group; m is 0 or 1; and n is 1 or 2);

(2) a group represented by Formula A2:

A2

(in Formula A2, B and n are as defined in Formula A1; and $R_9$ is a hydrogen atom or a C1-C6 alkyl group); or (3) a group represented Formula A3:

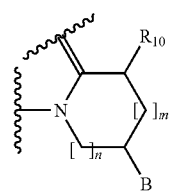

(in Formula A3, B, m, and n are as defined in Formula A1; and $R_{10}$ is a C1-C6 alkyl group).

Item 2. The compound or a salt thereof according to Item 1, wherein $R_2$ is a group represented by:

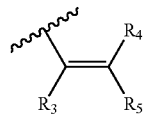

wherein $R_3$, $R_4$, and $R_5$ are the same or different, and each represents a hydrogen atom, a halogen atom, a C1-C6 alkyl group, an aminomethyl group that may be substituted with a C1-C6 alkyl group, or a 1-piperidinomethyl group, or a group represented by:

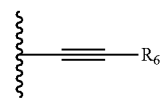

wherein $R_6$ represents a hydrogen atom or a C1-C6 alkyl group.

Item 3. The compound or a salt thereof according to Item 1 or 2, wherein $R_2$ is a group represented by:

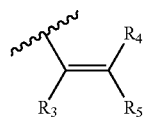

wherein $R_3$, $R_4$, and $R_5$ are the same or different, and each represents a hydrogen atom, a halogen atom, an aminomethyl group that may be substituted with a methyl group, or a 1-piperidinomethyl group.

Item 4. The compound or a salt thereof according to any one of Items 1 to 3, wherein the group:

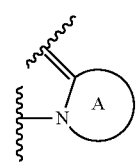

is (1) a group represented by Formula A1:

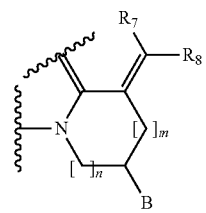

(in Formula A1, B is a group represented by:

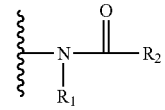

wherein $R_1$ is a hydrogen atom or a C1-C6 alkyl group; and $R_2$ is a group represented by:

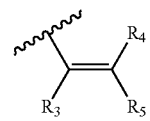

wherein $R_3$, $R_4$, and $R_5$ are the same or different, and each represents a hydrogen atom or a halogen atom, $R_7$ and $R_8$ are the same or different, and each represents a hydrogen atom or a C1-C6 alkyl group; m is 0 or 1; and n is 1); or (2) a group represented by Formula A2:

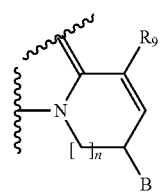

(in Formula A2, B and n are as defined in Formula A1; and $R_9$ is a hydrogen atom or a C1-C6 alkyl group).

Item 5. The compound or a salt thereof according to any one of Items 1 to 4, wherein the group:

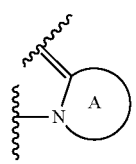

is (1) a group represented by Formula A1:

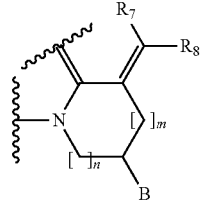

(in Formula A1, B is a group represented by:

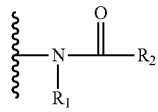

wherein $R_1$ is a hydrogen atom; and $R_2$ is a group represented by:

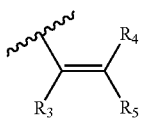

wherein $R_3$, $R_4$, and $R_5$ each represents a hydrogen atom, $R_7$ and $R_8$ each represents a hydrogen atom; m is 0; and n is 1); or (2) a group represented by Formula A2:

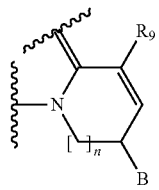

(in Formula A2, B and n are as defined in Formula A1; and $R_9$ represents a C1-C6 alkyl group).

Item 6. The compound or a salt thereof according to any one of Items 1 to 5, wherein the compound is selected from the following group of compounds:

(S)—N-(4-amino-6-methylene-5-(quinolin-3-yl)-7,8-dihydro-6H-pyrimido[5,4-b]pyrrolizin-7-yl)acrylamide (Compound 1);

(S)—N-(4-amino-6-methylene-5-(quinolin-3-yl)-7,8-dihydro-6H-pyrimido[5,4-b]pyrrolizin-7-yl)methacrylamide (Compound 2);

(S)—N-(4-amino-6-methylene-5-(quinolin-3-yl)-7,8-dihydro-6H-pyrimido[5,4-b]pyrrolizin-7-yl)but-2-enamide (mixture of E and Z) (Compound 3);

(S,E)-N-(4-amino-6-methylene-5-(quinolin-3-yl)-7,8-dihydro-6H-pyrimido[5,4-b]pyrrolizin-7-yl)-4-(dimethylamino)but-2-enamide (Compound 4);

(S,E)-N-(4-amino-6-methylene-5-(quinolin-3-yl)-7,8-dihydro-6H-pyrimido[5,4-b]pyrrolizin-7-yl)-3-chloroacrylamide (Compound 5);

(S,Z)—N-(4-amino-6-methylene-5-(quinolin-3-yl)-7,8-dihydro-6H-pyrimido[5,4-b]pyrrolizin-7-yl)-3-chloroacrylamide (Compound 6);

(S,E)-N-(4-amino-6-methylene-5-(quinolin-3-yl)-7,8-dihydro-6H-pyrimido[5,4-b]pyrrolizin-7-yl)-4-(piperidin-1-yl)but-2-enamide (Compound 7);

(S)—N-(4-amino-6-methylene-5-(quinolin-3-yl)-7,8-dihydro-6H-pyrimido[5,4-b]pyrrolizin-7-yl)propiolamide (Compound 8);

(S)—N-(4-amino-6-methylene-5-(quinolin-3-yl)-7,8-dihydro-6H-pyrimido[5,4-b]pyrrolizin-7-yl)but-2-ynamide (Compound 9);

(S,E)-N-(4-amino-6-methylene-5-(quinolin-3-yl)-7,8-dihydro-6H-pyrimido[5,4-b]pyrrolizin-7-yl)-4-(diethylamino)but-2-enamide (Compound 10);

(S,E)-N-(4-amino-6-methylene-5-(quinolin-3-yl)-7,8-dihydro-6H-pyrimido[5,4-b]pyrrolizin-7-yl)-4-(ethyl(methyl(methyl)amino)but-2-enamide (Compound 11);

(S,E)-N-(4-amino-6-methylene-5-(quinolin-3-yl)-7,8-dihydro-6H-pyrimido[5,4-b]pyrrolizin-7-yl)-4-(isopropyl(methyl)amino)but-2-enamide (Compound 12);

(R)—N-(4-amino-6-methylene-5-(quinolin-3-yl)-6,7,8,9-tetrahydropyrimido[5,4-b]indolizin-7-yl)acrylamide (Compound 13);

(S)—N-(4-amino-6-methyl-5-(quinolin-3-yl)-8,9-dihydropyrimido[5,4-b]indolizin-8-yl) acrylamide (Compound 14);

(S)—N-(4-amino-6-methylene-5-(quinolin-3-yl)-6,7,8,9-tetrahydropyrimido[5,4-b]indolizin-8-yl)acrylamide (Compound 15);

(R)—N-(4-amino-6-methyl-5-(quinolin-3-yl)-8,9-dihydropyrimido[5,4-b]indolizin-8-yl)acrylamide (Compound 16);

(R)—N-(4-amino-6-methylene-5-(quinolin-3-yl)-6, 7, 8,9-tetrahydropyrimido[5,4-b]indolizin-8-yl)acrylamide (Compound 17);

(S)—N-(4-amino-6-methylene-5-(quinolin-3-yl)-7,8,9,10-tetrahydro-6H-pyrimido[5',4':4,5]pyrrolo[1,2-a]azepin-8-yl)acrylamide (Compound 18);

(S,E)-N-(4-amino-6-ethylidene-5-(quinolin-3-yl)-6, 7,8,9-tetrahydropyrimido[5,4-b]indolizin-8-yl)acrylamide (Compound 19);

(S)—N-(4-amino-6-isopropyl-5-(quinolin-3-yl)-8,9-dihydropyrimido[5,4-b]indolizin-8-yl)acrylamide (Compound 20A);

(S)—N-(4-amino-6-(propan-2-ylidene)-5-(quinolin-3-yl)-6,7,8,9-tetrahydropyrimido[5,4-b]indolizin-8-yl)acrylamide (Compound 20B);

(R)—N-(4-amino-6-methylene-5-(quinolin-3-yl)-7,8-dihydro-6H-pyrimido[5,4-b]pyrrolizin-7-yl)-N-methylacrylamide (Compound 21);

(R)—N-(4-amino-6-methylene-5-(quinolin-3-yl)-6,7,8,9-tetrahydropyrimido[5,4-b]indolizin-8-yl)-N-methylacrylamide (Compound 22);

(R)—N-(4-amino-6-methyl-5-(quinolin-3-yl)-8,9-dihydropyrimido[5,4-b]indolizin-8-yl)-N-methylacrylamide (Compound 23);

N-((7S)-4-amino-6-methyl-5-(quinolin-3-yl)-7,8-dihydro-6H-pyrimido[5,4-b]pyrrolizin-7-yl)acrylamide (Compound 24);

(R)—N-(4-amino-6-methylene-5-(quinolin-3-yl)-7,8-dihydro-6H-pyrimido[5,4-b]pyrrolizin-7-yl)acrylamide (Compound 25);

(S)—N-(4-amino-6-methylene-5-(quinolin-3-yl)-7,8-dihydro-6H-pyrimido[5,4-b]pyrrolizin-7-yl)-N-methylacrylamide (Compound 26);

(S)—N-(4-amino-5-(quinolin-3-yl)-8,9-dihydropyrimido[5,4-b]indolizin-8-yl)acrylamide (Compound 27);
(R)—N-(4-amino-5-(quinolin-3-yl)-9,10-dihydro-8H-pyrimido[5',4':4,5]pyrrolo[1,2-a]azepin-8-yl)acrylamide (Compound 28);
N-((6R*,8S)-4-amino-6-methyl-5-(quinolin-3-yl)-6,7,8,9-tetrahydropyrimido[5,4-b]indolizin-8-yl)acrylamide (Compound 29A); and
N-((6S*, 8S)-4-amino-6-methyl-5-(quinolin-3-yl)-6, 7,8,9-tetrahydropyrimido[5,4-b]indolizin-8-yl)acrylamide (Compound 29B).

Item 7. The compound or a salt thereof according to any one of Items 1 to 5, wherein the compound is selected from the following group of compounds:
(S)—N-(4-amino-6-methylene-5-(quinolin-3-yl)-7,8-dihydro-6H-pyrimido[5,4-b]pyrrolizin-7-yl)acrylamide (Compound 1);
(S,E)-N-(4-amino-6-methylene-5-(quinolin-3-yl)-7,8-dihydro-6H-pyrimido[5,4-b]pyrrolizin-7-yl)-3-chloroacrylamide (Compound 5);
(S,Z)—N-(4-amino-6-methylene-5-(quinolin-3-yl)-7,8-dihydro-6H-pyrimido[5,4-b]pyrrolizin-7-yl)-3-chloroacrylamide (Compound 6);
(S)—N-(4-amino-6-methyl-5-(quinolin-3-yl)-8,9-dihydropyrimido[5,4-b]indolizin-8-yl)acrylamide (Compound 14); (S)—N-(4-amino-6-methylene-5-(quinolin-3-yl)-6,7,8,9-tetrahydropyrimido[5,4-b]indolizin-8-yl)acrylamide (Compound 15);
(S,E)-N-(4-amino-6-ethylidene-5-(quinolin-3-yl)-6,7,8,9-tetrahydropyrimido[5,4-b]indolizin-8-yl)acrylamide (Compound 19);
(R)—N-(4-amino-6-methylene-5-(quinolin-3-yl)-7,8-dihydro-6H-pyrimido[5,4-b]pyrrolizin-7-yl)-N-methylacrylamide (Compound 21);
(R)—N-(4-amino-6-methylene-5-(quinolin-3-yl)-6,7,8,9-tetrahydropyrimido[5,4-b]indolizin-8-yl)-N-methylacrylamide (Compound 22);
(R)—N-(4-amino-6-methyl-5-(quinolin-3-yl)-8,9-dihydropyrimido[5,4-b]indolizin-8-yl)-N-methylacrylamide (Compound 23); and
(R)—N-(4-amino-5-(quinolin-3-yl)-9,10-dihydro-8H-pyrimido[5',4':4,5]pyrrolo[1,2-a]azepin-8-yl)acrylamide (Compound 28).

Item 8. (S)—N-(4-amino-6-methylene-5-(quinolin-3-yl)-7,8-dihydro-6H-pyrimido[5,4-b]pyrrolizin-7-yl)acrylamide (Compound 1) or a salt thereof.

Item 9. (S)—N-(4-amino-6-methyl-5-(quinolin-3-yl)-8,9-dihydropyrimido[5,4-b]indolizin-8-yl)acrylamide (Compound 14) or a salt thereof.

Item 10. An EGFR inhibitor comprising the compound or a salt thereof according to any one of Items 1 to 9, as an active ingredient.

Item 11. A pharmaceutical composition comprising the compound or a salt thereof according to any one of Items 1 to 9.

Item 12. An antitumor agent comprising the compound or a salt thereof according to any one of Items 1 to 9, as an active ingredient.

Item 13. A method for treating or preventing cancer, the method comprising the step of administering, to a mammal, the compound or a salt thereof according to any one of Items 1 to 9 at a dose effective for treating or preventing cancer.

Item 14. Use of the compound or a salt thereof according to any one of Items 1 to 9 in the manufacture of an antitumor agent.

Item 15. The compound or a salt thereof according to any one of Items 1 to 9 for use in the prevention or treatment of cancer.

Advantageous Effects of Invention

According to the present invention, a novel compound represented by Formula (I) above or a salt thereof useful as an EGFR inhibitor is provided.

It has been clarified that the compound of the present invention or a salt thereof has excellent EGFR inhibition activity and a cancer cell strain growth inhibitory effect. In addition, the compound of the present invention or a salt thereof has advantageously few side effects as a result of excellent selectivity against EGFRs. Therefore, the compound of the present invention or a salt thereof is useful as an agent for preventing and/or treating cancer.

DESCRIPTION OF EMBODIMENTS

The compound represented by Formula (I) according to the present invention is a quinoline-substituted compound having a quinoline structure and an α,β-unsaturated amide structure, and is a novel compound nowhere disclosed in any of the above-mentioned prior art documents etc.

Specifically, the compound specifically disclosed in PTD 1 is an N-(3-(4-amino-6,7,8,9-tetrahydropyrimido[5,4-b]indolizin-5-yl)phenyl)benzamide derivative. The compound of the present invention is different from the compound disclosed in PTD 1 in that the compound of the present invention has a quinoline structure and an α,β-unsaturated amide structure.

In the specification of the present invention, examples of the "halogen atom" include fluorine, chlorine, bromine, and iodine.

In the specification of the present invention, the term "C1-C6 alkyl group" refers to a linear or branched alkyl group having 1 to 6 carbon atoms. Specific examples thereof include methyl, ethyl, n-propyl, isopropyl, n-butyl, isobutyl, sec-butyl, tert-butyl, pentyl, and hexyl.

In the specification of the present invention, the term "C6-C12 aryl group" refers to an aryl group having 6 to 12 carbon atoms. Specific examples thereof include phenyl, naphthyl, and biphenyl.

In the specification of the present invention, the term "C4-C9 heteroaryl group" refers to a monocyclic or bicyclic C4-C9 heteroaryl group containing 1 to 3 same or different heteroatoms selected from nitrogen, oxygen, and sulfur atoms; and is preferably a monocyclic or bicyclic C4-C9 heteroaryl group containing 1 to 3 nitrogen atoms. Specific examples thereof include thienyl, furyl, pyrrolyl, triazolyl, imidazolyl, pyrazolyl, isothiazolyl, isoxazolyl, pyridyl, pyrazinyl, pyrimidinyl, pyridazinyl, isobenzofuryl, indolizinyl, isoindolyl, indolyl, indazolyl, quinolyl, isoquinolyl, phthalazinyl, and naphthyridinyl.

In the specification of the present invention, the term "aminomethyl group that may be substituted with a C1-C6 alkyl group" refers to an aminomethyl group in which at least one hydrogen atom of the amino moiety may be substituted with a linear or branched alkyl group having 1 to 6 carbon atoms. Specific examples include aminomethyl, N-methylaminomethyl, N,N-dimethylaminomethyl, N-ethylaminomethyl, N,N-diethylaminomethyl, N-methylN-ethylaminomethyl, N-methylN-isopropylaminomethyl, N-propylaminomethyl, N-butylaminomethyl, N-pentylaminomethyl, and N-hexylaminomethyl.

In Formula (I) above, the moiety represented by:

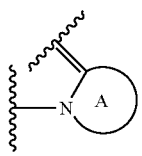

is (1) a group represented by Formula A1:

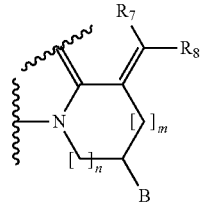

(in Formula A1, B, m, n, $R_7$, and $R_8$ are as defined above);
(2) a group represented by Formula A2:

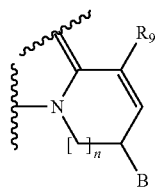

(in Formula A2, B, n, and $R_9$ are as defined above); or (3) a group represented by Formula A3:

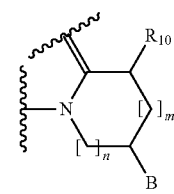

(in Formula A3, B, m, n, $R_7$, and Re are as defined above),
and is preferably (1) the group represented by Formula A1:

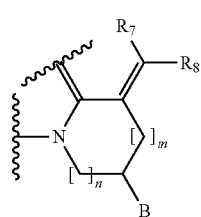

(in the formula, B, m, n, $R_7$, and $R_8$ are as defined above), or (2) the group represented by Formula A2:

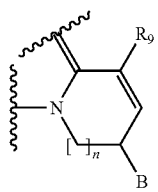

(in the formula, B, n and $R_9$ are as defined above)
m in Formula (I) is preferably 0.
n in Formula (I) is preferably 1.
$R_1$ in Formula (I) is preferably a hydrogen atom.
$R_2$ in Formula (I) is preferably a group represented by:

(wherein $R_3$, $R_4$, and $R_5$ are as defined above).
$R_3$, $R_4$, and $R_5$ in Formula (I) are preferably the same or different, and each represents a hydrogen atom, a halogen atom, a C1-C6 alkyl group, an aminomethyl group that may be substituted with a C1-C6 alkyl group, or a 1-piperidinomethyl group; more preferably, $R_3$, $R_4$, and $R_5$ are the same or different, and each represents a hydrogen atom, a halogen atom, an aminomethyl group that may be substituted with a methyl group, or a 1-piperidinomethyl group; further preferably, $R_3$, $R_4$, and $R_5$ are the same or different, and each represents a hydrogen atom or a halogen atom, particular preferably a hydrogen atom.

$R_7$ and $R_8$ in Formula (I) are preferably the same or different, and each represents a hydrogen atom or a C1-C6 alkyl group (preferably a C1-C3 alkyl group, more preferably a methyl group); further preferably, at least one of $R_7$ and $R_8$ is a hydrogen atom; particular preferably, both of $R_7$, and $R_8$ are hydrogen atoms.

$R_9$ in Formula (I) is preferably a C1-C6 alkyl group, more preferably a C1-C3 alkyl group, further preferably a methyl group.

The compound of the present invention or a salt thereof preferably has a strong enzyme inhibitory activity against EGFR (T790M/L858R); more preferably, the concentration of the compound by which 50% of the enzyme can be inhibited is 2 nM or less. Further, the compound of the present invention or a salt thereof preferably has a strong enzyme inhibitory activity against EGFR (d746-750/T790M); the 50% inhibitory concentration of the compound is also preferably 2 nM or less. Further, the compound of the present invention or a salt thereof preferably has a strong cell growth inhibitory effect against tumor cells with EGFR (T790M/L858R); the compound more preferably has a 50% inhibitory concentration of 200 nM or less, further preferably 100 nM or less, and particular preferably 40 nM or less.

Subsequently, the production method of the compound of the present invention is explained.

The compound (I) of the present invention may be produced, for example, through the following production method, the methods described in the Examples, and the like. However, the production method of the compound of the present invention is not limited to these reaction examples.

Production method 1

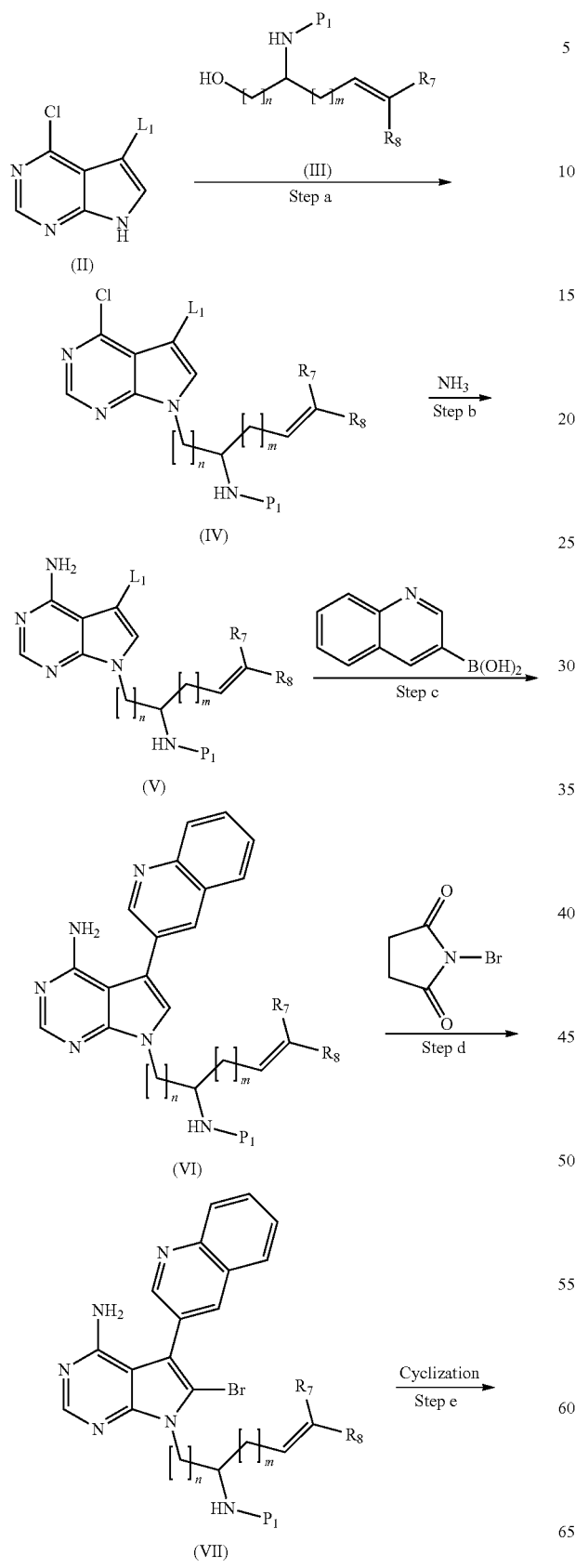

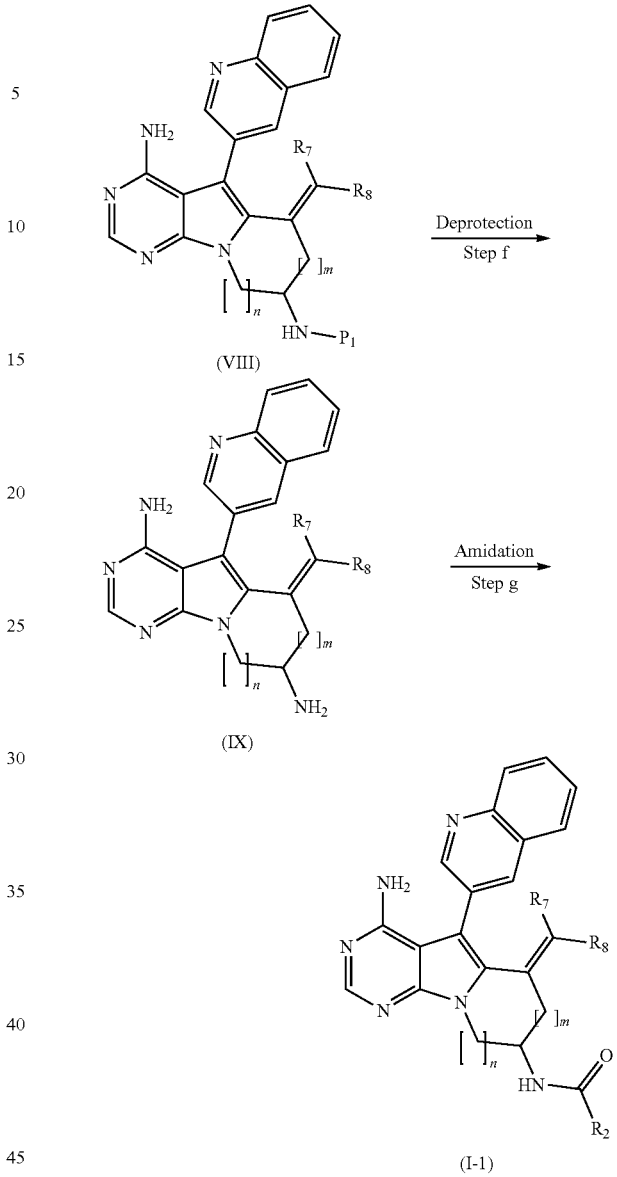

wherein $P_1$ is a protecting group of an amino group; $L_1$ is a leaving group; and $R_1$, $R_7$, $R_8$, m, and n are as defined above.

Step a

In this step, the compound represented by Formula (IV) is produced through a Mitsunobu reaction using the compounds represented by Formulas (II) and (III).

Examples of the leaving group represented by $L_1$ in the compound represented by Formula (II) include a bromine or iodine atom. The compound represented by Formula (II) may be a commercially available product, or can be produced by a known method. Examples of the protecting group of an amino group represented by P: in Formula (III) include a tert-butoxycarbonyl group and a benzoyl group. The compound represented by Formula (III) may be a commercially available product, or can be produced by a known method. The compound represented by Formula (III) can be used in an amount of 1 to 10 moles, and preferably 1 to 5 moles, per mole of the compound represented by Formula (II).

The Mitsunobu reaction may be performed according to a known method (for example, the method disclosed in Synthesis, p.1, 1981) or a similar method.

Examples of azodicarboxylic acid esters include diethyl azodicarboxylate and diisopropyl azodicarboxylate. Such an azodicarboxylic acid ester can be used in an amount of 1 to 10 moles, and preferably 1 to 5 moles, per mole of the compound represented by Formula (II).

As the phosphine compound, triphenylphosphine, tributylphosphine, or the like can be used. The phosphine compound can be used in an amount of 1 to 10 moles, and preferably 1 to 5 moles, per mole of the compound represented by Formula (II).

As a solvent, tetrahydrofuran, 1,2-dimethoxyethane, 1,4-dioxane, toluene, N,N-dimethylformamide, N,N-dimethylacetamide, dimethyl sulfoxide, N-methylpyrrolidin-2-one, and the like can be used alone, or as a mixture. The reaction time is 0.1 to 100 hours, and preferably 0.1 to 24 hours. The reaction temperature is 0° C. to the boiling temperature of the solvent, and preferably 0° C. to 100° C.

The thus-obtained compound represented by Formula (IV) can be subjected to the subsequent step after or without isolation or purification by known isolation and purification means, such as concentration, vacuum concentration, crystallization, solvent extraction, reprecipitation, and chromatography.

Step b

In this step, the compound represented by Formula (IV) is reacted with ammonia or a salt thereof to produce the compound represented by Formula (V).

The amount of ammonia or a salt thereof used in this step is typically an equimolar to excessive molar amount per mole of the compound represented by Formula (IV).

Any reaction solvent that does not adversely affect the reaction can be used. Examples of usable reaction solvents include water, methanol, ethanol, isopropanol, tert-butyl alcohol, tetrahydrofuran, 1,2-dimethoxyethane, 1,4-dioxane, N,N-dimethylformamide, N-methylpyrrolidin-2-one, dimethyl sulfoxide, and mixed solvents thereof.

The reaction temperature is typically 0° C. to 200° C., preferably from room temperature to 150° C. The reaction time is typically 5 minutes to 7 days, and preferably 30 minutes to 24 hours.

The thus-obtained compound represented by Formula (V) can be subjected to the subsequent step after or without isolation and purification by known isolation and purification means, such as concentration, vacuum concentration, crystallization, solvent extraction, reprecipitation, and chromatography.

Step c

In this step, the compound represented by Formula (V) is subjected to a coupling reaction with 3-quinolineboronic acid or 3-quinolineboronic acid ester to produce the compound represented by Formula (VI).

This step can be performed according to a generally known method (for example, Chemical Reviews, Vol. 95, p. 2457, 1995). This step can be performed in the presence of a transition metal catalyst and a base in a solvent that does not adversely affect the reaction.

The amount of 3-quinolineboronic acid or 3-quinolineboronic acid ester used may be 1 to 10 moles, and preferably 1 to 3 moles, per mole of the compound represented by Formula (V).

Examples of transition metal catalysts include palladium catalysts (e.g., palladium acetate, palladium chloride, tetrakis(triphenylphosphine)palladium, 1,1'-bis(diphenylphosphino)ferrocene-palladium (II) dichloride, and tris(dibenzylideneacetone)dipalladium (0)), nickel catalysts (e.g., nickel chloride), and the like. If necessary, a ligand (e.g., triphenylphosphine, tri-tert-butylphosphine, or 2-dicyclohexylphosphino-2',4',6'-triisopropylbiphenyl) can be added, and a metal oxide (such as copper oxide or silver oxide) can be used as a co-catalyst. The amount of the transition metal catalyst used may vary depending on the type of catalyst. The transition metal catalyst is typically used in an amount of 0.0001 to 1 mole, and preferably 0.01 to 0.5 moles, per mole of the compound represented by Formula (V). The amount of the ligand used is typically 0.0001 to 4 moles, and preferably 0.01 to 2 moles, per mole of the compound represented by Formula (V). The amount of the co-catalyst used is typically 0.0001 to 4 moles, and preferably 0.01 to 2 moles, per mole of the compound represented by Formula (V).

Examples of usable bases include organic amines (e.g., trimethylamine, triethylamine, diisopropylethylamine, N-methylmorpholine, 1,8-diazabicyclo[5,4,0]undec-7-ene, pyridine, and N,N-dimethylaniline), alkali metal salts (e.g., sodium hydrogen carbonate, potassium hydrogen carbonate, sodium carbonate, potassium carbonate, cesium carbonate, sodium phosphate, potassium phosphate, sodium hydroxide, and potassium hydroxide), metal hydrides (e.g., potassium hydride and sodium hydride), alkali metal alkoxides (e.g., sodium methoxide, sodium ethoxide, sodium tert-butoxide, and potassium tert-butoxide), alkali metal disilazides (e.g., lithium disilazide, sodium disilazide, and potassium disilazide), and the like. Among them, alkali metal salts such as sodium carbonate, potassium carbonate, cesium carbonate, sodium phosphate, and potassium phosphate; alkali metal alkoxides such as sodium tert-butoxide and potassium tert-butoxide; and organic amines such as triethylamine and diisopropylethylamine are preferable. The amount of the base used is typically 0.1 to 10 moles, and preferably 1 to 5 moles, per mole of the compound represented by Formula (V).

Any solvent that does not adversely affect the reaction can be used. Examples of usable solvent include hydrocarbons (e.g., benzene, toluene, and xylene), halogenated hydrocarbons (e.g., chloroform and 1,2-dichloroethane), nitriles (e.g., acetonitrile), ethers (e.g., 1,2-dimethoxyethane, tetrahydrofuran, and 1,4-dioxane), alcohols (e.g., methanol and ethanol), aprotic polar solvents (e.g., N,N-dimethylformamide, dimethyl sulfoxide, and hexamethyl phosphoryl amide), water, and mixed solvents thereof. The reaction time is 0.1 to 100 hours, and preferably 0.5 to 24 hours. The reaction temperature is 0° C. to the boiling temperature of the solvent, and preferably 20 to 150° C.

The thus-obtained compound represented by Formula (VI) can be subjected to the subsequent step after or without isolation and purification by known isolation and purification means, such as concentration, vacuum concentration, crystallization, solvent extraction, reprecipitation, and chromatography.

Step d

In this step, the compound represented by Formula (VI) is brominated by being reacted with N-bromosuccinimide to produce the compound represented by Formula (VII).

The halogenation can be performed by the method disclosed in WO 2006/102079, or by a similar method.

The amount of N-bromosuccinimide used in this step is 0.5 to 2.0 moles, and preferably 0.9 to 1.2 moles, per mole of the compound represented by Formula (VI).

Any reaction solvent that does not adversely affect the reaction can be used. For example, tetrahydrofuran, 1,4- dioxane, N,N-dimethylformamide, N-methylpyrrolidin-2-one, or a mixed solvent thereof can be preferably used.

The reaction temperature is typically −20 to 50° C., and preferably 0° C. to room temperature. The reaction time is typically 1 minute to 2 days, and preferably 5 minutes to 12 hours.

The thus-obtained compound represented by Formula (VI) can be subjected to the subsequent step after or without isolation or purification by known isolation and purification means, such as concentration, vacuum concentration, crystallization, solvent extraction, reprecipitation, and chromatography.

Step e

This step subjects the compound represented by Formula (VII) to an intramolecular cyclization reaction to produce the compound represented by Formula (VIII).

This step can be performed according to a generally known method (for example, the method disclosed in Chemical Reviews, Vol. 103, p. 2945, 2003).

Examples of transition metal catalysts include bivalent palladium catalysts (e.g., palladium acetate, palladium chloride, 1,1'-bis(diphenylphosphino)ferrocene-palladium(II)dichloride, etc.), and zero-valent palladium catalysts (e.g., tetrakis(triphenylphosphine)palladium, tris(dibenzylideneacetone)dipalladium, etc.). If necessary, a ligand (e.g., triphenylphosphine, tri-tert-butylphosphine, etc.) can be added. The amount of the transition metal catalyst used may vary depending on the type of catalyst. The transition metal catalyst is typically used in an amount of 0.0001 to 1 mole, and preferably 0.01 to 0.5 moles, per mole of the compound represented by Formula (VII). The amount of the ligand used is typically 0.0001 to 4 moles, and preferably 0.01 to 2 moles, per mole of the compound represented by Formula (VII).

Examples of usable bases include inorganic bases such as sodium hydrogen carbonate, sodium carbonate, potassium carbonate, cesium carbonate, sodium hydroxide, potassium hydroxide, cesium hydroxide, sodium hydride, or potassium hydride. Such a base can be used in an amount of 1 to 100 moles, and preferably 2 to 20 moles, per mole of the compound represented by Formula (VII).

Any solvent that does not adversely affect the reaction can be used. Examples of usable solvents include hydrocarbons (e.g., benzene, toluene, and xylene), ethers (e.g., 1,2-dimethoxyethane, tetrahydrofuran, and 1,4-dioxane), aprotic polar solvents (e.g., N,N-dimethylformamide, dimethyl sulfoxide, and hexamethyl phosphoryl amide), water, and mixed solvents thereof. The reaction time is 0.1 to 100 hours, and preferably 0.5 to 24 hours. The reaction temperature is −20° C. to the boiling temperature of the solvent, and preferably 0° C. to 150° C.

The thus-obtained compound represented by Formula (VIII) can be subjected to the subsequent step after or without isolation or purification by known isolation and purification means, such as concentration, vacuum concentration, crystallization, solvent extraction, reprecipitation, and chromatography.

Step f

In this step, the protected amino group of the compound represented by Formula (VIII) is deprotected to produce the compound represented by Formula (IX).

The deprotection can be performed by a known method, such as the method described in Protective Groups in Organic Synthesis, T. W. Greene, John Wiley & Sons (1981); or a similar method.

When a tert-butoxycarbonyl group is used as a protecting group, hydrochloric acid, sulfuric acid, methanesulfonic acid, trifluoroacetic acid, and the like are used as a deprotection reagent. The amount of the reagent used is preferably 1 to 100 moles per mole of the compound (VIII).

Any solvent that does not adversely affect the reaction can be used. Examples of usable solvents include water, methanol, ethanol, methylene chloride, chloroform, and the like, and mixed solvents thereof. The reaction time is 0.1 to 100 hours, and preferably 0.5 to 24 hours. The reaction temperature is 0° C. to the boiling temperature of the solvent, and is preferably from 0 to 50° C.

The thus-obtained compound represented by Formula (IX) can be subjected to the subsequent step after or without isolation and purification by known isolation and purification means, such as concentration, vacuum concentration, crystallization, solvent extraction, reprecipitation, and chromatography.

Step g

In this step, the compound represented by Formula (IX) is amidated with an α,β-unsaturated carboxylic acid, or α,β-unsaturated acid chloride or bromide to produce the compound represented by Formula (I-1) of the present invention.

When a carboxylic acid is used as an amidation reagent, the carboxylic acid can be used in an amount of 0.5 to 10 moles, preferably 1 to 3 moles, per mole of the compound represented by Formula (IX), in the presence of a suitable condensing agent. The carboxylic acid may be a commercially available product, or can be produced according to a known method.

Any reaction solvent that does not adversely affect the reaction can be used. Examples of usable solvent include toluene, benzene, methylene chloride, chloroform, tetrahydrofuran, 1,4-dioxane, N,N-dimethylformamide, dimethylacetamide, N-methylpyrrolidin-2-one, dimethyl sulfoxide, and mixed solvents thereof. The reaction temperature is typically −78 to 200° C., and preferably 0 to 50° C. The reaction time is typically 5 minutes to 3 days, and preferably 5 minutes to 10 hours.

Examples of condensation agents include diphenylphosphoryl azide, N,N'-dicyclohexylcarbodiimide, benzotriazol-1-yloxy-trisdimethylaminophosphonium salts, 4-(4,6-dimethoxy-1,3,5-triazin-2-yl)-4-methylmorpholinium chloride, 1-ethyl-3-(3-dimethylaminopropyl)carbodiimide, a combination of 1-ethyl-3-(3-dimethylaminopropyl)carbodiimide and 1-hydroxybenzotriazole, 2-chloro-1,3-dimethylimidazolinium chloride, O-(7-azabenzotriazo-1-yl)-N,N,N',N'-tetramethylhexauronium hexafluorophosphate, and the like.

If necessary, a base can be optionally added for the reaction. Examples of usable bases include organic bases such as triethylamine, diisopropylethylamine, pyridine, lutidine, collidine, 4-(N,N-dimethylamino)pyridine, potassium tert-butyrate, sodium tert-butyrate, sodium methoxide, sodium ethoxide, lithium hexamethyldisilazide, sodium hexamethyldisilazide, potassium hexamethyldisilazide, and butyl lithium; and inorganic bases such as sodium hydrogen carbonate, sodium carbonate, potassium carbonate, cesium carbonate, sodium hydroxide, and sodium hydride. Such a base can be added in an amount of 1 to 100 moles, and preferably 1 to 10 moles, per mole of the compound represented by Formula (IX).

When an acid chloride or acid bromide is used as an amidation reagent, the acid halide is used in an amount of 0.5 to 5 moles, and preferably 0.9 to 1.1 moles, per mole of the compound represented by Formula (IX). The acid halide may be a commercially available product, or can be produced according to a known method.

Any reaction solvent that does not adversely affect the reaction can be used. Examples thereof include toluene, benzene, methylene chloride, chloroform, tetrahydrofuran, 1,4-dioxane, N,N-dimethylformamide, dimethylacetamide, N-methylpyrrolidin-2-one, acetonitrile, water, and mixed solvents thereof. The reaction temperature is typically −78 to 200° C., preferably 0 to 50° C. The reaction time is typically 5 minutes to 3 days, and preferably 5 minutes to 10 hours.

If necessary, a base can be added for the reaction. Examples of usable bases include organic bases such as triethylamine, diisopropylethylamine, pyridine, lutidine, collidine, 4-(N,N-dimethylamino)pyridine, potassium tert-butyrate, sodium tert-butyrate, sodium methoxide, sodium ethoxide, lithium hexamethyldisilazide, sodium hexamethyldisilazide, potassium hexamethyldisilazide, and butyl lithium; and inorganic bases such as sodium hydrogen carbonate, sodium carbonate, potassium carbonate, cesium carbonate, sodium hydroxide, and sodium hydride. Such a base can be added in an amount of 1 to 100 moles, and preferably 1 to 20 moles, per mole of the compound represented by Formula (IX). The thus-obtained compound represented by Formula (I-1) can be isolated and purified by known isolation and purification means, such as concentration, vacuum concentration, crystallization, solvent extraction, reprecipitation, and chromatography.

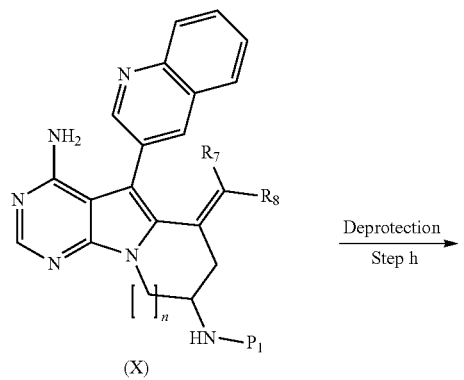

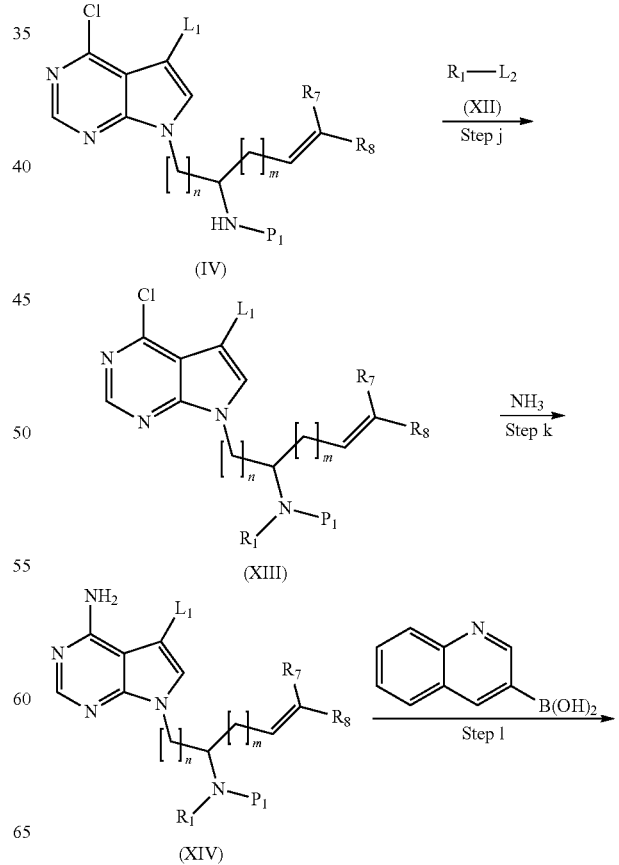

wherein $P_1$ represents a protecting group of an amino group; and $R_2$, $R_7$, $R_8$, $R_9$, and n are as defined above.

Step h

In this step, the protected amino group of the compound represented by Formula (X) is deprotected to produce the compound represented by Formula (XI).

The deprotection can be performed by a known method, such as the method described in Protective Groups in Organic Synthesis, T. W. Greene, John Wiley & Sons (1981); or a similar method.

When tert-butoxycarbonyl is used as a protecting group, hydrochloric acid, sulfuric acid, methanesulfonic acid, trifluoroacetic acid, or the like can be used as a deprotection reagent. The reagent is preferably used in an amount of 1 to 100 moles per mole of Compound (X).

Any solvent that does not adversely affect the reaction can be used. Examples of usable solvents include water, methanol, ethanol, methylene chloride, chloroform, and mixed solvents thereof. The reaction time is 0.1 to 100 hours, and preferably 0.5 to 24 hours. The reaction temperature is 0° C. to the boiling temperature of the solvent, and is preferably from 50° C. to the boiling temperature of the solvent.

The thus-obtained compound represented by Formula (XXI) can be subjected to the subsequent step after or without isolation and purification by known isolation and purification means, such as concentration, vacuum concentration, crystallization, solvent extraction, reprecipitation, and chromatography.

Step i

This step can be performed in the same manner as in Step g.

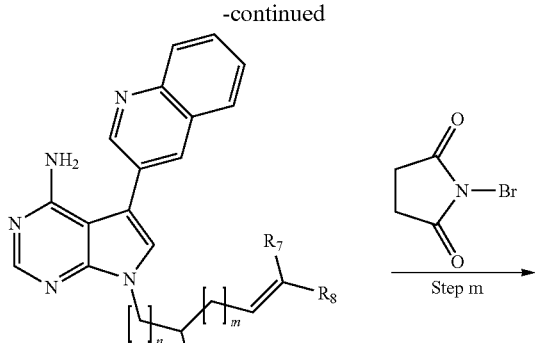

(XV)

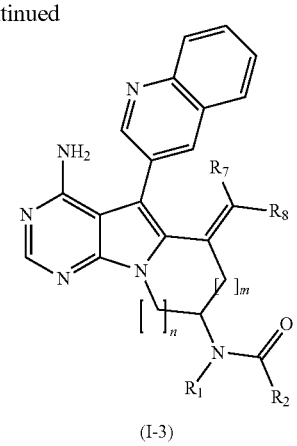

(I-3)

wherein P₁ represents a protecting group of an amino group; L₁ and L₂ represent a leaving group; and $R_1$, $R_2$, $R_7$, $R_8$, m, and n are as defined above.

Step j

In this step, the compound represented by Formula (XIII) is produced through an alkylation reaction using the compounds represented by Formulas (IV) and (XII) in the presence of a base.

In the compound represented by Formula (XII), examples of the leaving group represented by L₂ include bromine atom, iodine atom, methanesulfonic acid ester, p-toluenesulfonic acid ester, and the like. The compound represented by Formula (XII) may be a commercially available product, or can be produced by a known method. The compound represented by Formula (XII) can be used in an amount of 1 to 10 moles, and preferably 1 to 5 moles, per mole of the compound represented by Formula (IV). Examples of usable bases include organic amines (e.g., trimethylamine, triethylamine, diisopropylethylamine, N-methylmorpholine, 1,8-diazabicyclo[5,4,0]undec-7-ene, pyridine, and N,N-dimethylaniline), alkali metal salts (e.g., sodium hydrogen carbonate, potassium hydrogen carbonate, sodium carbonate, potassium carbonate, cesium carbonate, sodium phosphate, potassium phosphate, sodium hydroxide, and potassium hydroxide), metal hydrides (e.g., potassium hydride and sodium hydride), alkali metal alkoxides (e.g., sodium methoxide, sodium ethoxide, sodium tert-butoxide, and potassium tert-butoxide), alkali metal disilazides (e.g., lithium disilazide, sodium disilazide, and potassium disilazide), and the like. Among them, alkali metal salts such as sodium carbonate, potassium carbonate, cesium carbonate, sodium phosphate, and potassium phosphate; and metal hydrides such as sodium hydride; alkali metal alkoxides such as sodium tert-butoxide and potassium tert-butoxide are preferable. The amount of the base used is typically 0.1 to 10 moles, and preferably 1 to 5 moles, per mole of the compound represented by Formula (V).

As a solvent, tetrahydrofuran, 1,2-dimethoxyethane, 1,4-dioxane, N,N-dimethylformamide, N,N-dimethylacetamide, dimethyl sulfoxide, N-methylpyrrolidin-2-one, and the like can be used alone, or as a mixture. The reaction time is 0.1 to 100 hours, and preferably 0.5 to 24 hours. The reaction temperature is 0° C. to the boiling temperature of the solvent, and is preferably from 20° C. to 150° C.

The thus-obtained compound represented by Formula (XIII) can be subjected to the subsequent step after or without isolation or purification by known isolation and purification means, such as concentration, vacuum concentration, crystallization, solvent extraction, reprecipitation, and chromatography.

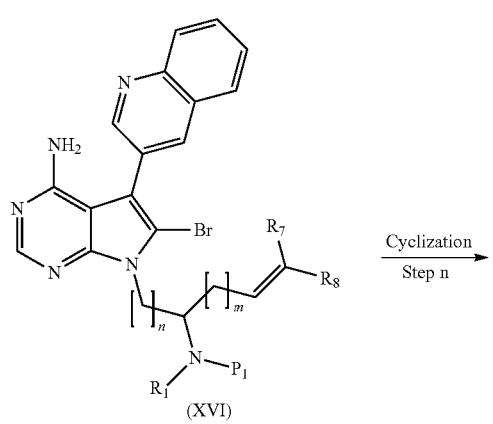

(XVI)

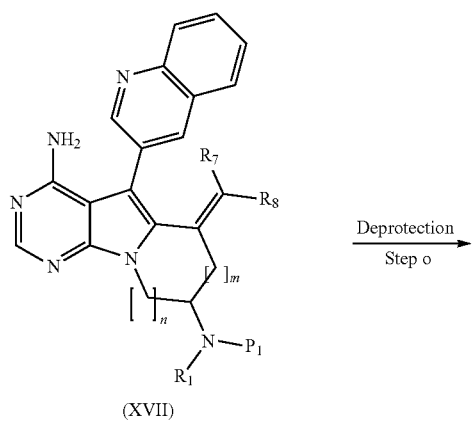

(XVII)

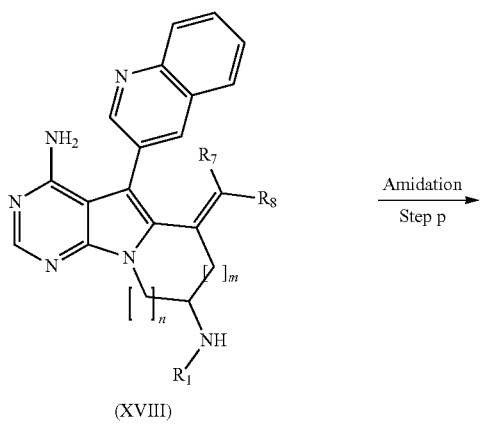

(XVIII)

Step k

This step can be performed in the same manner as in Step b.

Step l

This step can be performed in the same manner as in Step c.

Step m

This step can be performed in the same manner as in Step d.

Step n

This step can be performed in the same manner as in Step e.

Step o

This step can be performed in the same manner as in Step f.

Step p

This step can be performed in the same manner as in Step g.

wherein $P_1$ represents a protecting group of an amino group; and $R_1$, $R_2$, R?, $R_8$, $R_9$, and n are as defined above.

Step q

This step can be performed in the same manner as in Step h.

Step r

This step can be performed in the same manner as in Step g.

Production Method 4

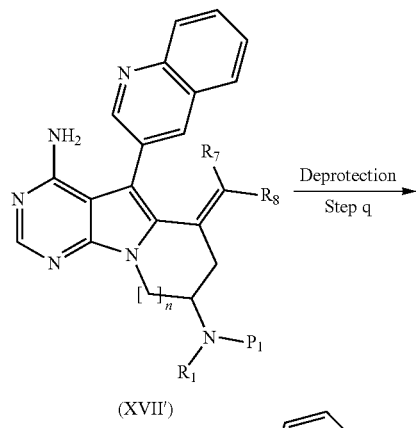

(XVII')

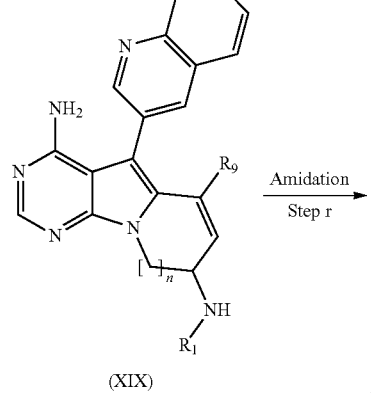

(XIX)

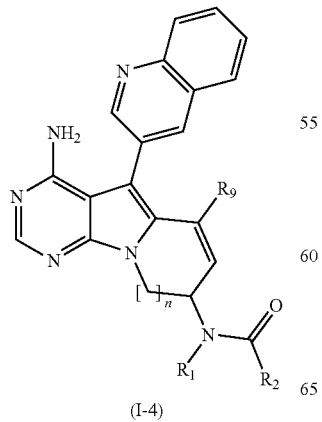

(I-4)

Production Method 5

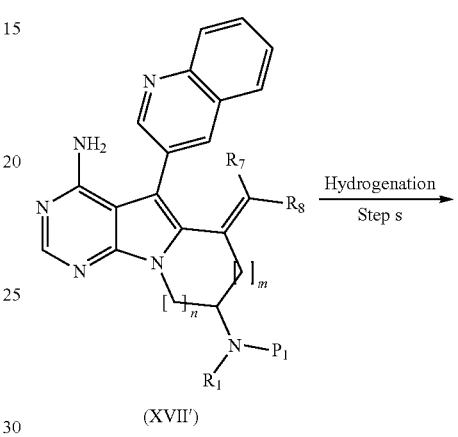

(XVII')

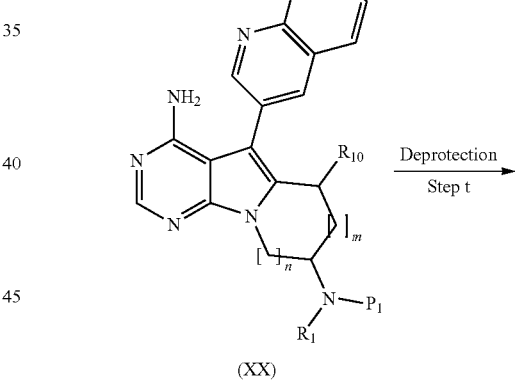

(XX)

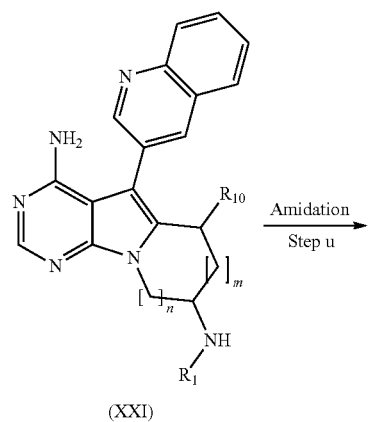

(XXI)

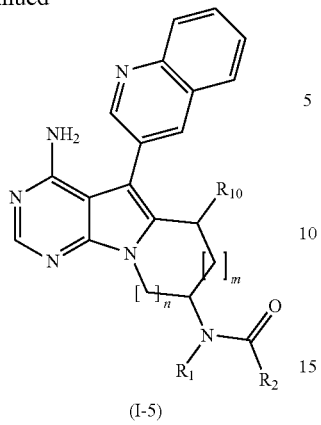

(I-5)

wherein P₁ represents a protecting group of an amino group; and $R_1$, $R_2$, $R_7$, $R_8$, $R_{10}$, m, and n are as defined above.

Step s

In this step, the compound represented by Formula (XX) is produced through hydrogenation with respect to the compound represented by Formula (XVII) in the presence of a catalyst.

Examples of catalyst include palladium-carbon catalyst, palladium hydroxide-carbon catalyst, and Raney nickel catalyst. The catalyst can be used in an amount of 0.01 moles to an excessive amount, preferably from 0.1 moles to 10 moles, per mole of the compound represented by Formula (XVII).

The hydrogenation can be performed at 1 atm to 100 atm, preferably 1 atm to 10 atm. As a solvent, methanol, ethanol, ethyl acetate, tetrahydrofuran, 1,2-dimethoxyethane, 1,4-dioxane, N,N-dimethylformamide, N,N-dimethylacetamide, N-methylpyrrolidin-2-one, water, and the like can be used alone, or as a mixture. The reaction time is from 0.1 to 100 hours, preferably from 0.5 to 48 hours. The reaction temperature ranges from room temperature to the boiling temperature of the solvent, preferably from room temperature to 100° C.

The thus-obtained compound represented by Formula (XX) can be subjected to the subsequent step after or without isolation or purification by known isolation and purification means, such as concentration, vacuum concentration, crystallization, solvent extraction, reprecipitation, and chromatography.

Step t

This step can be performed in the same manner as in Step f.

Step u

This step can be performed in the same manner as in Step g.

Production Method 6

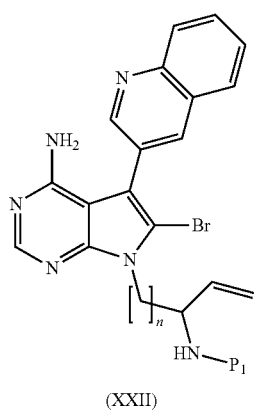

(XXII)

Cyclization
Step v

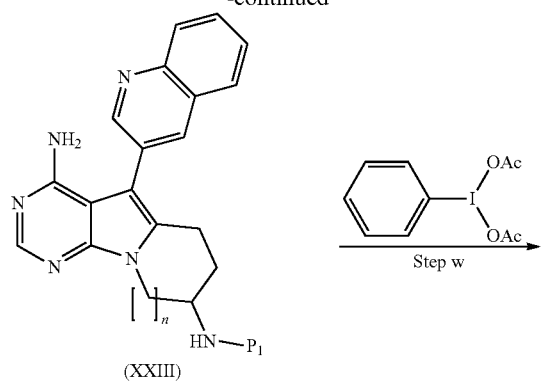

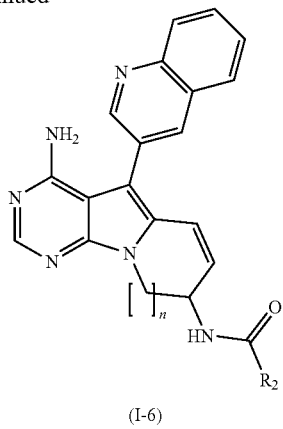

(I-6)

wherein P₁ represents a protecting group of an amino group; and R₂ and n are as defined above.

Step v

In this step, an organic borane reagent is allowed to act on the compound represented by Formula (XXII) to prepare an alkyl borane intermediate in the system, and then the compound represented by Formula (XXIII) is produced in the presence of a transition metal catalyst and a base.

This step can be performed according to a generally known method (for example, WO 2006/102079).

Examples of organic borane reagents include 9-BBN(9-borabicyclo[3.3.1]-nonane), 9-BBN(9-borabicyclo[3.3.1]-nonane) dimer, disiamylborane(bis(1,2-dimethylpropyl)borane), thexylborane(1,1,2-trimethylpropyl)borane), and the like. The organic borane reagent is preferably 9-BBN(9-borabicyclo[3.3.1]-nonane) or 9-BBN(9-borabicyclo[3.3.1]-nonane) dimer, and particularly preferably 9-BBN(9-borabicyclo[3.3.1]-nonane). The amount of the organic borane reagent used is not particularly limited insofar as an alkyl borane intermediate can be produced. The organic borane reagent can be used in an amount of 1 to 20 moles per mole of the compound represented by Formula (XXII); the amount of the organic borane reagent is preferably 6 to 10 moles from the viewpoint of facilitating the progress of the reaction.

As a transition metal catalyst, for example, a bivalent palladium catalyst (e.g., palladium acetate, palladium chloride, and 1,1'-bis(diphenylphosphino)ferrocene-palladium (II) dichloride) can be used. If necessary, a ligand (e.g., triphenylphosphine and tri-tert-butylphosphine) can be used. The amount of the transition metal catalyst used may vary depending on the type of catalyst. The transition metal catalyst is typically used in an amount of 0.0001 to 1 mole, and preferably 0.01 to 0.5 moles, per mole of the compound represented by Formula (XXII). The ligand is typically used in an amount of 0.0001 to 4 moles, and preferably 0.01 to 2 moles, per mole of the compound represented by Formula (XXII).

Alternatively, for example, a zero-valent palladium catalyst can be used. Examples of zero-valent palladium catalysts include tetrakis(triphenylphosphine)palladium, tris(dibenzylideneacetone)dipalladium, palladium carbon, and the like. Tetrakis(triphenylphosphine)palladium or tris(dibenzylideneacetone)dipalladium is preferable, and tetrakis(triphenylphosphine)palladium is particularly preferable. The amount of the zero-valent palladium catalyst used is not particularly limited insofar as the intramolecular cyclization reaction can proceed, and may vary depending on the type of catalyst. The zero-valent palladium catalyst can be used in an amount of 0.0001 to 1 mole, and preferably 0.01 to 0.5 moles, per mole of the compound represented by Formula (XXII).

If necessary, a ligand may be added with a zero-valent palladium catalyst. Examples of such ligands include triphenylphosphine, 1,1'-bis(diphenylphosphino)ferrocene, tri-tert-butylphosphine, tricyclohexylphosphine, 2-dicyclohexylphosphino-2',6'-dimethoxybiphenyl, 2-dicyclohexylphosphino-2',4',6'-triisopropylbiphenyl, 2-(di-tert-butylphosphino)biphenyl, 2-dicyclohexylphosphino-2'-(N,N-dimethylamino)biphenyl, 4,5'-bis(diphenylphosphino)-9,9'-dimethylxanthene, and the like. When tris(dibenzylideneacetone)dipalladium is used as a zero-valent palladium catalyst, triphenylphosphine can be added as a ligand. The amount of the ligand used is not particularly limited insofar as the intramolecular cyclization reaction can proceed. The ligand can be used in an amount of 0.0001 to 4 moles, and preferably 0.01 to 2 moles, per mole of the compound represented by Formula (XXII).

Examples of bases include inorganic bases such as sodium hydrogen carbonate, sodium carbonate, potassium carbonate, cesium carbonate, and alkali metal hydroxides. Alkali metal hydroxides are preferable. Examples of alkali metal hydroxides include lithium hydroxide, sodium hydroxide, potassium hydroxide, and cesium hydroxide. Lithium hydroxide, sodium hydroxide, potassium hydroxide, or cesium hydroxide is preferably used. Lithium hydroxide or sodium hydroxide is particularly preferable. The amount of the base used is not particularly limited insofar as the reaction proceeds. The base can be used in an amount of 1 to 100 moles, and preferably 2 to 20 moles, per mole of the compound represented by Formula (XXII). Alkali metal hydroxide can be used in the form of an aqueous alkali metal hydroxide solution.

As the combination of an organic borane reagent, an alkali metal hydroxide, and a zero-valent palladium catalyst, a combination of a preferable organic borane reagent, a preferable alkali metal hydroxide, and a preferable zero-valent palladium catalyst is preferable. A combination of a particularly preferable organic borane reagent, a particularly preferable alkali metal hydroxide, and a particularly preferable zero-valent palladium catalyst is particularly preferable.

Any solvent that does not adversely affect the reaction can be used. Examples thereof include hydrocarbons (e.g., benzene, toluene, and xylene), ethers (e.g., 1,2-dimethoxyethane, tetrahydrofuran, and 1,4-dioxane), aprotic polar solvents (e.g., N,N-dimethylformamide, dimethyl sulfoxide, and hexamethyl phosphoryl amide), water, and mixtures thereof. 1,2-Dimethoxyethane or tetrahydrofuran is preferably used. Tetrahydrofuran is particularly preferable from the viewpoint of stability of the organic borane reagent and the generated alkylborane intermediate. The amount of the solvent used is not particularly limited insofar as the reaction proceeds. The solvent can be used in an amount that is 1 to 300 times, and preferably 10 to 96 times, the weight of the compound represented by Formula (XXII).

The reaction time is not particularly limited insofar as the compound of Formula (XXIII) can be obtained. The reaction time may be 0.1 to 100 hours, and preferably 0.5 to 24 hours.

The reaction temperature is not particularly limited insofar as the compound represented by Formula (XXIII) can ultimately be obtained. The reaction temperature may be −20° C. to the boiling temperature of the solvent, and preferably 0° C. to 150° C. In the intramolecular cyclization reaction of the alkylborane intermediate using a zero-valent palladium catalyst and an alkali metal hydroxide aqueous solution, a low reaction temperature tends to cause side reactions, which results in a low yield. Therefore, the temperature is preferably 61° C. or higher.

The thus-obtained compound represented by Formula (XXIII) can be subjected to the subsequent step after or without isolation or purification by known isolation and purification means, such as concentration, vacuum concentration, crystallization, solvent extraction, reprecipitation, and chromatography.

In this step, generation of an alkylborane intermediate in the system can be confirmed. For example, LCMS spectra can be used as the confirmation method.

Step w

In this step, the compound represented by Formula (XXIV) is produced by reacting the compound represented by Formula (XXIII) with iodobenzene diacetate.

The amount of the iodobenzene diacetate used in this step is 1 to 10 moles, preferably 1 to 2 moles, per mole of the compound represented by Formula (XXIII).

In the above reaction, if necessary, tetrabutylammonium iodide may be added. The tetrabutylammonium iodide can be added in an amount of 0.01 to 10 moles, preferably 0.1 to 1 mole, per mole of the compound represented by Formula (XXIII).

Any reaction solvent that does not adversely affect the reaction can be used. Examples of suitable reaction solvents include methylene chloride, chloroform, 1,2-dichloroethane, acetic acid and mixed solvents thereof.

The reaction temperature is generally 0° C. to the boiling temperature of the solvent, and is preferably from 0° C. to room temperature. The reaction time is 0.1 to 100 hours, preferably 0.1 to 24 hours.

The thus-obtained compound represented by Formula (XXIV) can be subjected to the subsequent step after or without isolation or purification by known isolation and purification means, such as concentration, vacuum concentration, crystallization, solvent extraction, reprecipitation, and chromatography.

Step x

In this step, the protected hydroxy group of the compound represented by Formula (XXIV) is deprotected to produce the compound of Formula (XXV).

The deprotection can be performed by a known method, such as the method described in Protective Groups in Organic Synthesis, T. W. Greene, John Wiley & Sons (1981); or a similar method.

When the acetyl group is deprotected, examples of the deprotection reagent include sodium hydroxide, potassium hydroxide, and the like. The amount of the reagent used is preferably 1 to 100 moles per mole of the compound represented by Formula (XXIV).

Any solvent that does not adversely affect the reaction can be used. Examples of the solvent include water, methanol, ethanol, tetrahydrofuran, and mixed solvents thereof. The reaction time is 0.1 to 100 hours, and preferably 0.5 to 24 hours. The reaction temperature is 0° C. to the boiling temperature of the solvent, and is preferably from 0 to 50° C.

The thus-obtained compound represented by Formula (XXV) can be subjected to the subsequent step after or without isolation or purification by known isolation and purification means, such as concentration, vacuum concentration, crystallization, solvent extraction, reprecipitation, and chromatography.

Step y

In this step, the compound represented by Formula (XXVI) is produced by subjecting the compound represented by Formula (XXV) to an elimination reaction.

In the elimination reaction, acids such as p-toluenesulfonic acid monohydrate, 10-camphorsulfonic acid, and the like are used. The amount of the acid used is 0.1 to 100 moles, preferably 1 to 10 moles, per mole of the compound represented by Formula (XXV).

Any solvent that does not adversely affect the reaction can be used. Examples of the solvent include toluene, xylene, and mixed solvents thereof. The reaction time is 0.1 to 100 hours, and preferably 0.5 to 24 hours. The reaction temperature ranges from room temperature to the boiling temperature of the solvent.

The thus-obtained compound represented by Formula (XXVI) can be subjected to the subsequent step after or without isolation or purification by known isolation and purification means, such as concentration, vacuum concentration, crystallization, solvent extraction, reprecipitation, and chromatography.

Step z

This step can be performed in the same manner as in Step g.

In the above production methods 1 to 6, for functional groups having an active proton, such as amino, imino, hydroxy, carboxy, carbonyl, and amide groups, and indole, protected reagents can be used, or a protecting group can be introduced into such a functional group according to a usual method; afterward, the protecting group can be removed in an appropriate step in each production method.

The "protecting group of an amino group or protecting group of an imino group" is not particularly limited, insofar as it has a protecting function. Examples of such protecting groups include aralkyl groups such as benzyl, p-methoxybenzyl, 3,4-dimethoxybenzyl, o-nitrobenzyl, p-nitrobenzyl, benzhydryl, trityl, and cumyl; lower alkanoyl groups such as formyl, acetyl, propionyl, butyryl, pivaloyl, trifluoroacetyl, and trichloroacetyl; benzoyl; arylalkanoyl groups such as phenylacetyl and phenoxyacetyl; lower alkoxycarbonyl groups such as methoxycarbonyl, ethoxycarbonyl, propyloxycarbonyl, and tert-butoxycarbonyl; aralkyloxycarbonyl groups such as p-nitrobenzyloxycarbonyl and phenethyloxycarbonyl; lower alkylsilyl groups such as trimethylsilyl and tert-butyldimethylsilyl; tetrahydropyranyl; trimethylsilylethoxymethyl; lower alkylsulfonyl groups such as methylsulfonyl, ethylsulfonyl, and tert-butylsulfonyl; lower alkylsulfinyl groups such as tert-butylsulfinyl; arylsulfonyl groups such as benzenesulfonyl and toluenesulfonyl; and imido groups such as phthalimido. In particular, trifluoroacetyl, acetyl, tert-butoxycarbonyl, benzyloxycarbonyl, trimethylsilylethoxymethyl, cumyl, and the like are preferable.

The "protecting group of a hydroxy group" is not particularly limited insofar as it has a protecting function. Examples of such protecting groups include lower alkyl groups such as methyl, ethyl, propyl, isopropyl, and tert-butyl; lower alkylsilyl groups such as trimethylsilyl and tert-butyldimethylsilyl; lower alkoxymethyl groups such as methoxymethyl and 2-methoxyethoxymethyl; tetrahydropyranyl; trimethylsilylethoxymethyl; aralkyl groups such as benzyl, p-methoxybenzyl, 2,3-dimethoxybenzyl, o-nitrobenzyl, p-nitrobenzyl, and trityl; and acyl groups such as formyl, acetyl, and trifluoroacetyl. In particular, methyl, methoxymethyl, tetrahydropyranyl, trimethylsilylethoxymethyl, tert-butyldimethylsilyl, and acetyl are preferable.

The "protecting group of a carboxy group" is not particularly limited insofar as it has a protecting function. Examples of such protecting groups include lower alkyl groups such as methyl, ethyl, propyl, isopropyl, and tert-butyl; halo-lower-alkyl groups such as 2,2,2-trichloroethyl; lower alkenyl groups such as allyl; trimethylsilylethoxymethyl; and aralkyl groups such as benzyl, p-methoxybenzyl, p-nitrobenzyl, benzhydryl, and trityl. In particular, methyl, ethyl, tert-butyl, allyl, benzyl, p-methoxybenzyl, trimethylsilylethoxymethyl, and the like are preferable.

The "protecting group of a carbonyl group" is not particularly limited insofar as it has a protecting function. Examples of such protecting groups include ethylene ketal, trimethylene ketal, dimethyl ketal, and like ketals and acetals.

The method for removing such a protecting group may vary depending on the type of protecting group, stability of the desired compound (I), etc. For example, the following methods can be used: solvolysis using an acid or a base according to the method disclosed in a publication (Protective Groups in Organic Synthesis, third edition, T. W. Green, John Wiley & Sons (1999)) or a similar method, i.e., a method comprising reacting with 0.01 moles or a large excess of an acid, preferably trifluoroacetic acid, formic acid, or hydrochloric acid, or an equimolar to large excessive molar amount of a base, preferably potassium hydroxide or calcium hydroxide; chemical reduction using a metal hydride complex, etc.; or catalytic reduction using a palladium-carbon catalyst, Raney nickel catalyst, etc.

The compound of the present invention can be isolated and purified by usual isolation and purification means. Examples of such means include solvent extraction, recrystallization, preparative reversed-phase high-performance liquid chromatography, column chromatography, preparative thin-layer chromatography, and the like.

When the compound of the present invention has isomers such as optical isomers, stereoisomers, regioisomers, and rotational isomers, any of the isomers and mixtures thereof is included within the scope of the compound of the present invention. For example, when the compound has optical isomers, the optical isomer separated from a racemic mixture is also included within the scope of the compound of the present invention. Each of such isomers can be obtained as a single compound by known synthesis and separation means (e.g., concentration, solvent extraction, column chromatography, recrystallization, etc.).

In the present invention, the carbon atom bound to a substituent B in Formula (I) is an asymmetric carbon; therefore, the compound includes isomers. As stated above, unless otherwise specified, the compound of the present invention includes all of the enantiomers and mixtures thereof. The compound of the present invention may be a mixture of R and S enantiomers. Such a mixture may be a mixture comprising 90% or more, 95% or more, or 99% or more of R enantiomer; or a mixture comprising 90% or more, 95% or more, or 99% or more of S enantiomer.

Methods for chiral resolution include, for example: diastereomer method of causing a chiral resolving agent to act on the compound of the present invention to form a salt, and resolving one of the enantiomers using a solubility difference etc., of the obtained salt; preferential crystallization method of adding one of the enantiomers to a supersaturated solution of a racemate as a seed for crystallization; and column chromatography such as HPLC using a chiral column. A chiral resolving agent that can be used in the diastereomer method can be appropriately selected from, for example, acid resolving agents such as tartaric acid, malic acid, lactic acid, mandelic acid, 10-camphorsulfonic acid, and derivatives thereof; and basic resolving agents such as brucine, strychnine, quinine, and like alkaloid compounds, amino acid derivatives, cinchonidine, and α-methylbenzylamine. In addition, one of the enantiomers of the compound of the present invention alone can be obtained not only by obtaining the compound of the present invention as a mixture of each of the enantiomers and then conducting the above described methods of chiral resolution, but also by obtaining, through chiral resolution by the above described methods etc., and using one enantiomer of the compound of the present invention as a synthetic raw material. Furthermore, methods for obtaining one of the enantiomers of the compound of the present invention or its raw material compound include a method of preferentially obtaining one of the enantiomers by adjusting reaction conditions for a catalyst or the like in a reaction step of generating asymmetric carbon.

The compound of the present invention or a salt thereof may be in the form of crystals. Single crystals and polymorphic mixtures are included within the scope of the compound of the present invention or a salt thereof. Such crystals can be produced by crystallization according to a crystallization method known per se in the art. The compound of the present invention or a salt thereof may be a solvate (e.g., a hydrate) or a non-solvate. Any of such forms are included within the scope of the compound of the present invention or a salt thereof. Compounds labeled with an isotope (e.g., 3H, 14C, 35S, and 125I) are also included within the scope of the compound of the present invention or a salt thereof.

The salt of the compound of the present invention or of the intermediate thereof refers to a common salt used in the field of organic chemistry. Examples of such salts include base addition salts to carboxy when the compound has carboxy, and acid addition salts to an amino or basic heterocyclic group when the compound has an amino or basic heterocyclic group.

Examples of base addition salts include alkali metal salts such as sodium salts and potassium salts; alkaline earth metal salts such as calcium salts and magnesium salts; ammonium salts; and organic amine salts such as trimethylamine salts, triethylamine salts, dicyclohexylamine salts, ethanolamine salts, diethanolamine salts, triethanolamine salts, procaine salts, and N,N'-dibenzylethylenediamine salts.

Examples of acid addition salts include inorganic acid salts such as hydrochlorides, sulfates, nitrates, phosphates, and perchlorates; organic acid salts such as acetates, formates, maleates, fumarates, tartrates, citrates, ascorbates, and trifluoroacetates; and sulfonates such as methanesulfonates, isethionates, benzenesulfonates, and p-toluenesulfonates.

The compound of the present invention or a salt thereof has excellent EGFR inhibitory activity and is useful as an antitumor agent. Further, the compound of the present invention or a salt thereof has excellent selectivity toward EGFR, and advantageously fewer side effects caused by other kinases. The type of malignant tumor to be treated by the compound of the present invention or a salt thereof is not particularly limited. Examples of malignant tumors include epithelial cancers (e.g., respiratory system cancers, digestive system cancers, reproductive system cancers, secretion system cancers, and the like), sarcomas, hematopoietic tumors, central nervous system tumors, and peripheral nerve tumors. Preferable examples include epithelial cancers. More preferable examples include respiratory system cancers. Further, the organ from which the tumor is developed is not particularly limited. Examples include head and neck cancers, esophagus cancer, gastric cancer, colon cancer, rectum cancer, liver cancer, gallbladder cancer, cholangiocarcinoma, biliary tract cancer, pancreatic cancer, lung cancer, breast cancer, ovarian cancer, cervical cancer, endometrial cancer, renal cancer, bladder cancer, prostate cancer, testicular tumor, osteosarcoma, soft-tissue sarcoma, blood cancer, multiple myeloma, skin cancer, brain tumor, and mesothelioma. Preferably, the target cancer is head and neck cancers, gastric cancer, colon cancer, rectum cancer, liver cancer, pancreatic cancer, lung cancer, breast cancer, ovarian cancer, renal cancer, or prostate cancer, particularly preferably lung cancer.

Further, the compound of the present invention or a salt thereof has excellent inhibitory activity against mutated EGFR. Examples of such a mutated EGFR include drug-tolerant mutated EGFR and hypersensitive mutated EGFR. Therefore, the compound of the present invention or a salt thereof is useful as an antitumor agent for treating the above malignant tumors having mutated EGFR.

When the compound of the present invention or a salt thereof is used as a pharmaceutical preparation, a pharmaceutical carrier can be added, if required, thereby forming a suitable dosage form according to prevention and treatment purposes. Examples of the dosage form include oral preparations, injections, suppositories, ointments, patches, and the like. Of these, oral preparations are preferable. Such dosage forms can be formed by methods conventionally known to persons skilled in the art.

As the pharmaceutical carrier, various conventional organic or inorganic carrier materials used as preparation materials may be blended as an excipient, binder, disintegrant, lubricant, or colorant in solid preparations; or as a solvent, solubilizing agent, suspending agent, isotonizing agent, buffer, or soothing agent in liquid preparations. Moreover, pharmaceutical preparation additives, such as antiseptics, antioxidants, colorants, sweeteners, and stabilizers, may also be used, if required.

Oral solid preparations are prepared as follows. After an excipient is added optionally with a binder, disintegrant, lubricant, colorant, taste-masking or flavoring agent, etc., to the compound of the present invention, the resulting mixture is formulated into tablets, coated tablets, granules, powders, capsules, or the like by ordinary methods.

Examples of excipients include lactose, sucrose, D-mannitol, glucose, starch, calcium carbonate, kaolin, microcrystalline cellulose, and silicic acid anhydride. Examples of binders include water, ethanol, 1-propanol, 2-propanol, simple syrup, liquid glucose, liquid α-starch, liquid gelatin, D-mannitol, carboxymethyl cellulose, hydroxypropyl cellulose, hydroxypropyl starch, methyl cellulose, ethyl cellulose, shellac, calcium phosphate, polyvinylpyrrolidone, and the like. Examples of disintegrators include dry starch, sodium alginate, powdered agar, sodium hydrogen carbonate, calcium carbonate, sodium lauryl sulfate, stearic acid monoglyceride, lactose, and the like. Examples of lubricants include purified talc, stearic acid salt sodium, magnesium stearate, borax, polyethylene glycol, and the like. Examples of colorants include titanium oxide, iron oxide, and the like. Examples of taste-masking or flavoring agents include sucrose, bitter orange peel, citric acid, tartaric acid, and the like.

When a liquid preparation for oral administration is prepared, a taste-masking agent, a buffer, a stabilizer, a flavoring agent, and the like may be added to the compound of the present invention; and the resulting mixture may be formulated into an oral liquid preparation, syrup, elixir, etc., according to an ordinary method.

In this case, the same taste-masking or flavoring agent as those mentioned above may be used. An example of the buffer is sodium citrate, and examples of the stabilizer include tragacanth, gum arabic, and gelatin. As necessary, these preparations for oral administration may be coated according to methods known in the art with an enteric coating or other coating for the purpose of, for example, persistence of effects. Examples of such coating agents include hydroxypropyl methylcellulose, ethyl cellulose, hydroxymethyl cellulose, hydroxypropyl cellulose, polyoxyethylene glycol, and Tween 80 (registered trademark).

When an injection agent is prepared, a pH regulator, a buffer, a stabilizer, an isotonizing agent, a local anesthetic, and the like, may be added to the compound of the present invention; and the mixture may be formulated into a subcutaneous, intramuscular, or intravenous injection according to an ordinary method.

Examples of the pH adjuster and the buffer used herein include sodium citrate, sodium acetate, and sodium phosphate. Examples of the stabilizer include sodium pyrosulfite, EDTA, thioglycolic acid, and thiolactic acid. Examples of the local anesthetic include procaine hydrochloride and lidocaine hydrochloride. Examples of the tonicity agent include sodium chloride, dextrose, D-mannitol, and glycerol.

When a suppository is prepared, pharmaceutically acceptable carriers known in the art, such as polyethylene glycol, lanolin, cacao butter, and fatty acid triglyceride; and as necessary, surfactants such as Tween 80 (registered trademark), may be added to the compound of the present invention, and the resulting mixture may be formulated into a suppository according to an ordinary method.

When an ointment is prepared, a commonly used base, stabilizer, wetting agent, preservative, and the like, may be blended into the compound of the present invention, as necessary; and the obtained mixture may be mixed and formulated into an ointment according to an ordinary method.

Examples of the base include liquid paraffin, white petrolatum, white beeswax, octyl dodecyl alcohol, and paraffin.

Examples of the preservative include methyl paraoxybenzoate, ethyl paraoxybenzoate, and propyl paraoxybenzoate.

When a patch is prepared, the above-described ointment, cream, gel, paste, or the like, may be applied to an ordinary substrate according to an ordinary method.

As the substrate, woven fabrics or non-woven fabrics comprising cotton, staple fibers, or chemical fibers; and films or foam sheets of soft vinyl chloride, polyethylene, polyurethane, etc., are suitable.

The amount of the compound of the present invention to be incorporated in each of such dosage unit forms depends on the condition of the patient to whom the compound is administered, the dosage form thereof, etc. In general, in the case of an oral agent, the amount of the compound is 0.05 to 1000 mg per dosage unit form. In the case of an injection, the amount of the compound is 0.01 to 500 mg per dosage unit form; and in the case of a suppository, the amount of the compound is 1 to 1000 mg per dosage unit form.

The daily dose of the medicine in such a dosage form depends on the condition, body weight, age, gender, etc., of the patient, and cannot be generalized. For example, the daily dose for an adult (body weight: 50 kg) may be generally 0.05 to 5,000 mg, and preferably 0.1 to 1,000 mg; and is preferably administered in one dose, or in two to three divided doses, per day.

Examples of mammals to which the compound of the present invention is administered include humans, monkeys, mice, rats, rabbits, dogs, cats, cows, horses, pigs, and sheep.

EXAMPLES

The present invention is more specifically explained below with reference to Examples; however, the present invention is not limited to these Examples.

In the Examples, commercially available reagents were used, unless otherwise specified. Purif-Pack® SI, produced by Moritex Corp. (produced by Shoko Scientific Co., Ltd.); KP-Sil® Silica prepacked column, produced by Biotage; HP-Sil® Silica prepacked column, produced by Biotage, or HP-Sphere® Silica prepacked column, produced by Biotage, was used for the silica gel column chromatography. Purif-Pack® NH, produced by Moritex Corp. (produced by Shoko Scientific Co., Ltd.); or KP-NH® prepacked column, produced by Biotage, was used for the basic silica gel column chromatography. Kieselgel™ 60F254, Art. 5744, produced by Merck, or NH2 Silica Gel 60F254 Plate, produced by Wako, was used for the preparative thin-layer chromatography. NMR spectrum was measured by using AL400 (400 MHz; produced by JEOL), or Mercury 400 (400 MHz; produced by Agilent Technologies, Inc.) spectrometer. When the deuterated solvent contains tetramethylsilane, tetramethylsilane was used as the internal reference. Otherwise, an NMR solvent was used as the internal reference. All of the δ values are shown by ppm. The microwave reaction was performed using an Initiator, produced by Biotage.

Further, the LCMS spectrum was measured using an Acquity SQD (quadrupole), produced by Waters Corporation, under the following conditions.
Column: Acquity UPLC® BEH C18, 2.1×50 mm, 1.7 μm, produced by Waters Corporation
MS detection: ESI positive
UV detection: 254 and 210 nm
Column flow rate: 0.5 mL/min
Mobile phase: Water/acetonitrile (0.1% formic acid)
Injection volume: 1 μL

TABLE 1

| Gradient | | |
|---|---|---|
| Time (min) | Water | Acetonitrile |
| 0 | 95 | 5 |
| 0.1 | 95 | 5 |
| 2.1 | 5 | 95 |
| 3.0 | STOP. | |

Reversed-phase preparative HPLC purification was performed using a preparative separation system available from Gilson.
Column: CombiPrep Pro C18, 50×30 mm I.D., S-5 μm (produced by YMC).
UV detection: 254 nm
Column flow rate: 40 mL/min
Mobile phase: Water/acetonitrile (0.1% trifluoroacetic acid)
Injection volume: 0.1 to 1 mL.

Each symbol stands for the following.
s: Singlet
d: Doublet
t: Triplet
q: Quartet
dd: Double Doublet
dt: Double Triplet
ddd: Double Double Doublet
m: Multiplet
brs: Broad Singlet
DMSO-d$_6$: Deuterated dimethyl sulfoxide
CDCl$_3$: Deuterated chloroform
CD$_3$OD: Deuterated methanol
THF: Tetrahydrofuran
DMF: N,N-dimethylformamide
DME: 1,2-Dimethoxyethane
DMSO: Dimethylsulfoxide
HATU: O-(7-azabenzotriazol-1-yl)-N,N,N',N'-tetramethyluronium hexafluorophosphate Example 1

(S)—N-(4-amino-6-methylene-5-(quinolin-3-yl)-7,8-dihydro-6H-pyrimido[5,4-b]pyrrolizin-7-yl)acrylamide (Compound 1)

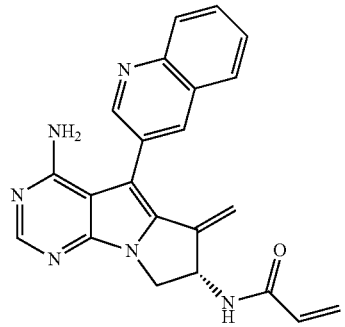 [SMILES: C=CC(=O)N[C@@H]1Cn2c(c(-c3cnc4ccccc4c3)c3c(N)ncnc32)C1=C]

Step 1: Synthesis of (S)-tert-butyl (1-(4-chloro-5-iodo-7H-pyrrolo[2,3-d]pyrimidin-7-yl)but-3-en-2-yl)carbamate

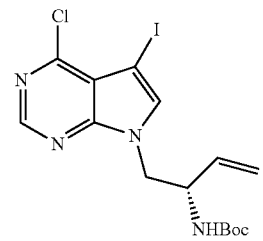 [SMILES: C=C[C@@H](Cn1cc(I)c2c(Cl)ncnc21)NC(=O)OC(C)(C)C]

Diisopropyl azodicarboxylate (2.44 ml) was slowly added to a solution of triphenylphosphine (13.1 g) in THF (70 ml) under ice-cooling. The reaction mixture was stirred under ice-cooling for 1 hour, and then a solution of (S)-tert-butyl (1-hydroxybut-3-en-2-yl)carbamate (7.0 g) synthesized according to the method disclosed in NPD Org. Lett., 2005, vol. 7, No. 5, pp. 847-849 and 4-chloro-5-iodo-7H-pyrrolo[2,3-d]pyrimidine (6.97 g) in THF (35 ml) was slowly added thereto. After the reaction mixture was stirred at room temperature for 2 hours, the solvent was distilled off under reduced pressure. The resulting residue was purified by silica gel column chromatography (developing solvent: hexane/ethyl acetate), thereby obtaining the title compound (20.84 g) as a light-yellow, oily substance.
ESI-MS m/z 448, 450 [M+H]$^+$.

Step 2: Synthesis of (S)-tert-butyl (1-(4-amino-5-iodo-7H-pyrrolo[2,3-d]pyrimidin-7-yl)but-3-en-2-yl)carbamate

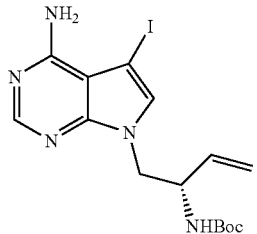 [SMILES: C=C[C@@H](Cn1cc(I)c2c(N)ncnc21)NC(=O)OC(C)(C)C]

An 8 N ammonia-methanol solution (89.4 ml) was added to the (S)-tert-butyl (1-(4-chloro-5-iodo-7H-pyrrolo[2,3-d]pyrimidin-7-yl)but-3-en-2-yl)carbamate (20.84 g) obtained in Step 1, and the mixture was stirred in an autoclave at 120° C. for 6 hours. The reaction mixture was cooled with ice, and the solvent was distilled off under reduced pressure. After the resulting residue was diluted with a small amount of methanol, the resulting precipitate was collected by filtration, washed with cold methanol (11 ml), and then dried under reduced pressure, thereby obtaining the title compound (8.28 g) as a milky-white solid.
ESI-MS m/z 430 [M+H]+.

Step 3: Synthesis of (S)-tert-butyl (1-(4-amino-5-(quinolin-3-yl)-7H-pyrrolo[2,3-d]pyrimidin-7-yl)but-3-en-2-yl)carbamate

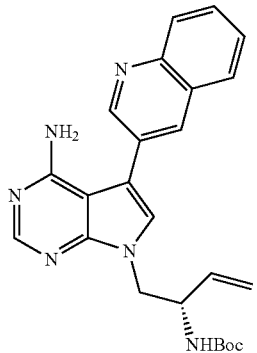 [SMILES: C=C[C@@H](Cn1cc(-c2cnc3ccccc3c2)c2c(N)ncnc21)NC(=O)OC(C)(C)C]

A mixture of the (S)-tert-butyl (1-(4-amino-5-iodo-7H-pyrrolo[2,3-d]pyrimidin-7-yl)but-3-en-2-yl)carbamate (8.26 g) obtained in Step 2, 3-quinolineboronic acid (4.99 g), cesium carbonate (12.54 g), 1,1'-bis(diphenylphosphino)ferrocene-palladium(II)dichloride (785.6 mg), DME (66 ml), and water (33 ml) was stirred under a nitrogen atmosphere at 100° C. for 2 hours. After cooling the reaction mixture, water and ethyl acetate were added thereto to separate the organic layer. The aqueous layer was then extracted with ethyl acetate twice. The resulting organic layer was dried over anhydrous magnesium sulfate, and the solvent was distilled off under reduced pressure. The resulting residue was purified by silica gel column chromatography (developing solvent: hexane/ethyl acetate, ethyl acetate/methanol), thereby obtaining the title compound (8.0 g) as a light-orange solid.
ESI-MS m/z 431 [M+H]+.

Step 4: Synthesis of (S)-tert-butyl (1-(4-amino-6-bromo-5-(quinolin-3-yl)-7H-pyrrolo[2,3-d]pyrimidin-7-yl)but-3-en-2-yl)carbamate

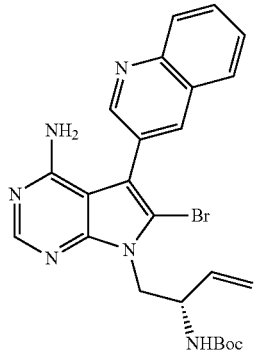 [SMILES: C=C[C@@H](Cn1c(Br)c(-c2cnc3ccccc3c2)c2c(N)ncnc21)NC(=O)OC(C)(C)C]

N-Bromosuccinimide (3.63 g) was added to a solution of the (S)-tert-butyl (1-(4-amino-5-(quinolin-3-yl)-7H-pyrrolo[2,3-d]pyrimidin-7-yl)but-3-en-2-yl)carbamate (71.98 g) obtained in Step 3 in DMF (64 ml) at −15° C., and the mixture was stirred at −15° C. for 1 hour. A 10% aqueous sodium thiosulfate solution and ethyl acetate were added to the reaction mixture, and stirred at room temperature for 10 minutes. The organic layer was separated, and the aqueous layer was extracted with ethyl acetate twice. The resulting organic layer was washed with a saturated sodium chloride solution twice, and dried over anhydrous magnesium sulfate. The solvent was distilled off under reduced pressure. The resulting residue was purified by silica gel column chromatography (developing solvent: ethyl acetate/methanol), thereby obtaining the title compound (6.30 g) as a light-brown solid.
ESI-MS m/z 509, 511 [M+H]+.

Step 5: Synthesis of (S)-tert-butyl (4-amino-6-methylene-5-(quinolin-3-yl)-7,8-dihydro-6H-pyrimido[5,4-b]pyrrolizin-7-yl)carbamate

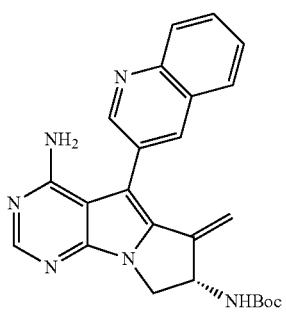 [SMILES: C=C1c2c(-c3cnc4ccccc4c3)c3c(N)ncnc3n2C[C@H]1NC(=O)OC(C)(C)C]

4N sodium hydroxide aqueous solution (28.8 ml) was added to a solution of the (S)-tert-butyl (1-(4-amino-6-bromo-5-(quinolin-3-yl)-7H-pyrrolo[2,3-d]pyrimidin-7-yl)but-3-en-2-yl)carbamate (5.00 g) obtained in Step 4 in THF (100 ml), and the mixture was degassed under reduced pressure, followed by nitrogen purging. After tetrakis(triphenylphosphine)palladium (1.13 g) was added, the mixture was stirred overnight while being heated under reflux. After the reaction mixture was cooled to room temperature, extraction was performed using ethyl acetate, and the resulting organic layer was washed with a saturated sodium chloride solution and dried over anhydrous sodium sulfate. After filtration and concentration, the resulting residue was purified by silica gel chromatography (developing solvent: ethyl acetate/methanol), thereby obtaining the title compound as an orange solid (5.01 g).

ESI-MS m/z 429 [M+H]$^+$.

Step 6: Synthesis of Compound 1

A 4 N hydrogen chloride-dioxane solution (1 ml) and methanol (1 ml) were added to a solution of the (S)-tert-butyl (4-amino-6-methylene-5-(quinolin-3-yl)-7,8-dihydro-6H-pyrimido[5,4-b]pyrrolizin-7-yl)carbamate (100 mg) obtained in Step 5 in chloroform (1 ml), and the mixture was stirred for 5 hours at room temperature. The reaction mixture was concentrated under reduced pressure, thereby yielding (S)-6-methylene-5-(quinolin-3-yl)-7,8-dihydro-6H-pyrimido[5,4-b]pyrrolizin-4,7-diamine hydrochloride.

Diisopropylethylamine (0.187 ml) was added to a solution of (S)-6-methylene-5-(quinolin-3-yl)-7,8-dihydro-6H-pyrimido[5,4-b]pyrrolizin-4,7-diamine hydrochloride in chloroform (4 ml), and a 100 mg/ml solution of acryloyl chloride in chloroform (0.19 ml) was added under ice-cooling. The mixture was stirred for 40 minutes. The reaction mixture was purified by silica gel chromatography (developing solvent: ethyl acetate/methanol); after concentration, the resulting residue was suspended and washed in ethyl acetate/hexane. The resulting solid was collected by filtration and dried under reduced pressure, thereby obtaining the title compound (49 mg) as a light-green solid.

$^1$H-NMR (DMSO-d$_6$) δ: 3.88-3.93 (1H, m), 4.57-4.63 (1H, m), 5.03 (1H, d, J=2.4 Hz), 5.24 (1H, d, J=2.4 Hz), 5.55-5.62 (1H, m), 5.68 (1H, dd, J=10.0, 2.4 Hz), 6.12-6.38 (4H, m), 7.65 (1H, dd, J=7.8, 7.8 Hz), 7.77-7.83 (1H, m), 8.04-8.11 (2H, m), 8.15 (1H, s), 8.41 (1H, d, J=2.2 Hz), 8.82 (1H, d, J=7.8 Hz), 8.98 (1H, d, J=2.2 Hz).

ESI-MS m/z 383[M+H]$^+$.

Example 2

(S)—N-(4-amino-6-methylene-5-(quinolin-3-yl)-7,8-dihydro-6H-pyrimido[5,4-b]pyrrolizin-7-yl)methacrylamide (Compound 2)

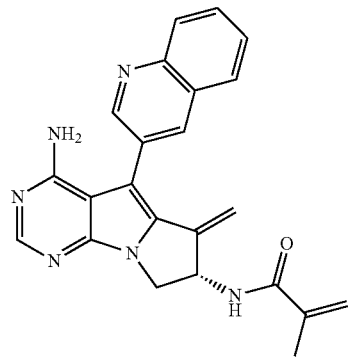 [SMILES: C=C(C)C(=O)N[C@@H]1Cn2c(c(-c3cnc4ccccc4c3)c3c(N)ncnc32)C1=C]

Step 1: Synthesis of (S)-6-methylene-5-(quinolin-3-yl)-7,8-dihydro-6H-pyrimido[5,4-b]pyrrolizin-4,7-diamine

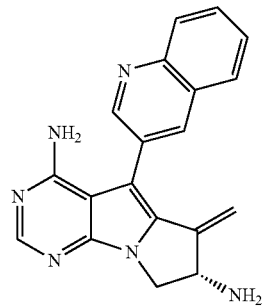 [SMILES: C=C1c2c(-c3cnc4ccccc4c3)c3c(N)ncnc3n2C[C@H]1N]

5 N hydrochloric acid (12 ml) was added to a solution of the (S)-tert-butyl (4-amino-6-methylene-5-(quinolin-3-yl)-7,8-dihydro-6H-pyrimido[5,4-b]pyrrolizin-7-yl)carbamate (5.01 g) obtained in Step 5 of Example 1 in ethanol (25 ml), and the resulting mixture was stirred for 1 hour at an external temperature of 70 to 80° C. After the reaction mixture was cooled to room temperature, the reaction mixture was washed with chloroform, and the aqueous layer was adjusted to about pH 10 using a 5 N sodium hydroxide aqueous solution, followed by extraction with chloroform. The resulting organic layer was dried over anhydrous sodium sulfate, followed by filtration and concentration. The resulting residue was purified by basic silica gel chromatography (developing solvent: chloroform/methanol), thereby obtaining the title compound (2.10 g) as a yellow solid.

ESI-MS m/z 329 [M+H]$^+$.

Step 2: Synthesis of Compound 2

Diisopropylethylamine (0.0318 ml) and methacryloyl chloride (0.0148 ml) were successively added to a solution of the (S)-6-methylene-5-(quinolin-3-yl)-7,8-dihydro-6H-pyrimido[5,4-b]pyrrolizin-4,7-diamine (50.0 mg) obtained in Step 1 in acetonitrile (2.0 ml) and water (2.0 ml) at 0° C., and the resulting mixture was stirred for 45 minutes at the same temperature. The reaction mixture was poured into a saturated aqueous sodium bicarbonate solution, followed by extraction with chloroform. After the organic layer was dried over anhydrous sodium sulfate, the solvent was distilled off under reduced pressure. The resulting residue was purified by silica gel column chromatography (developing solvent: ethyl acetate/methanol), thereby obtaining the title compound (38.0 mg) as a light-yellow solid.

$^1$H-NMR (CDCl$_3$) δ: 2.02 (3H, s), 4.03 (1H, dd, J=11.6, 4.9 Hz), 4.70 (1H, dd, J=11.6, 8.2 Hz), 5.20-5.22 (3H, m), 5.44 (2H, d, J=1.7 Hz), 5.73-5.75 (1H, m), 5.82 (1H, s), 6.89 (1H, d, J=7.6 Hz), 7.61-7.65 (1H, m), 7.76-7.80 (1H, m), 7.87 (1H, d, J=8.3 Hz), 8.15 (1H, d, J=8.5 Hz), 8.21-8.25 (2H, m), 9.06 (1H, d, J=2.2 Hz).

ESI-MS m/z 397[M+H]$^+$.

Example 3

(S)—N-(4-amino-6-methylene-5-(quinolin-3-yl)-7,8-dihydro-6H-pyrimido[5,4-b]pyrrolizin-7-yl)but-2-enamide (mixture of E and Z) (Compound 3)

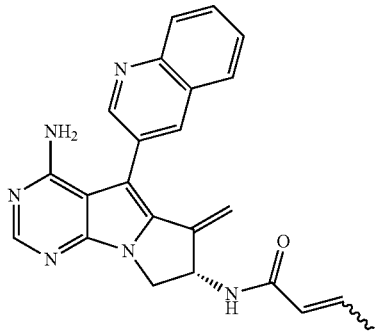

The same synthesis as in Step 2 of Example 2 was performed using crotonoyl chloride instead of the methacryloyl chloride used in Step 2 of Example 2, thereby obtaining the title mixture (8.8 mg) as a light-yellow solid.

$^1$H-NMR (CDCl$_3$) δ: 1.83-1.90 (3H, m), 4.01 (1H, dd, J=11.6, 5.2 Hz), 4.73 (1H, dd, J=11.6, 8.2 Hz), 5.00 (2H, s), 5.19 (1H, d, J=1.5 Hz), 5.44 (1H, d, J=2.0 Hz), 5.75-5.77 (1H, m), 5.87-5.91 (1H, m), 6.27 (1H, d, J=8.3 Hz), 6.92-7.01 (1H, m), 7.62-7.66 (1H, m), 7.78-7.82 (1H, m), 7.88 (1H, d, J=7.3 Hz), 8.18 (1H, d, J=8.0 Hz), 8.28-8.29 (2H, m), 9.08 (1H, d, J=2.2 Hz).
ESI-MS m/z 397[M+H]$^+$.

Example 4

(S,E)-N-(4-amino-6-methylene-5-(quinolin-3-yl)-7,8-dihydro-6H-pyrimido[5,4-b]pyrrolizin-7-yl)-4-(dimethylamino)but-2-enamide (Compound 4)

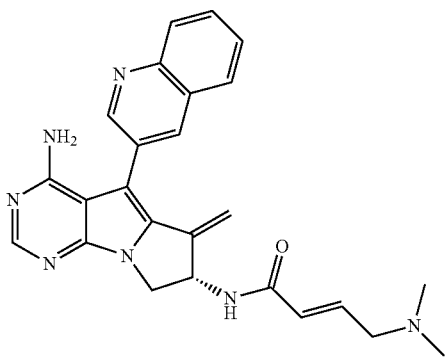 [SMILES: C=C1c2c(-c3cnc4ccccc4c3)c3c(N)ncnc3n2C[C@H]1NC(=O)/C=C/CN(C)C]

(E)-4-(dimethylamino) but-2-enoic acid hydrochloride (60.6 mg), HATU (139 mg), diisopropylethylamine (0.106 ml), and DMF (1.0 ml) were successively added to a suspension of the (S)-6-methylene-5-(quinolin-3-yl)-7,8-dihydro-6H-pyrimido[5,4-b]pyrrolidin-4,7-diamine (100 mg) obtained in Step 1 of Example 2 in methylene chloride (3.0 ml) at room temperature, and the mixture was stirred for 1.5 hours at the same temperature. The reaction mixture was poured into a saturated aqueous sodium bicarbonate solution, followed by extraction with ethyl acetate. After the organic layer was dried over anhydrous sodium sulfate, the solvent was distilled off under reduced pressure. The resulting residue was purified by silica gel column chromatography (developing solvent: ethyl acetate/methanol), thereby obtaining the title compound (114 mg) as a light-yellow solid.

$^1$H-NMR (CDCl$_3$) δ: 2.23 (6H, s), 3.07 (2H, dd, J=6.0, 1.3 Hz), 4.01 (1H, dd, J=11.6, 5.0 Hz), 4.70 (1H, dd, J=11.6, 8.2 Hz), 5.09 (2H, brs), 5.20 (1H, d, J=2.0 Hz), 5.43 (1H, d, J=2.0 Hz), 5.73-5.79 (1H, m), 6.07 (1H, dt, J=15.4, 1.3 Hz), 6.72 (1H, brs), 6.94 (1H, dt, J=15.4, 6.0 Hz), 7.61-7.65 (1H, m), 7.77-7.81 (1H, m), 7.87 (1H, d, J=8.0 Hz), 8.16 (1H, d, J=8.5 Hz), 8.25-8.26 (2H, m), 9.05 (1H, d, J=2.0 Hz).
ESI-MS m/z 440[M+H]$^+$.

Example 5

(S,E)-N-(4-amino-6-methylene-5-(quinolin-3-yl)-7,8-dihydro-6H-pyrimido[5,4-b]pyrrolizin-7-yl)-3-chloroacrylamide (Compound 5)

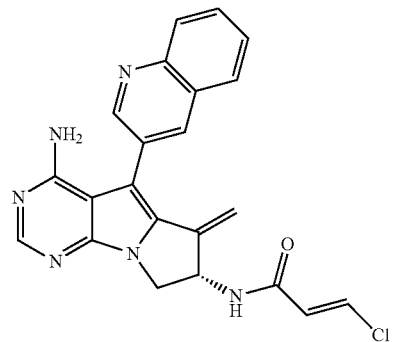 [SMILES: C=C1c2c(-c3cnc4ccccc4c3)c3c(N)ncnc3n2C[C@H]1NC(=O)/C=C/Cl]

The same synthesis as in Example 4 was performed using trans-3-chloroacrylic acid instead of the (E)-4-(dimethylamino)but-2-enoic acid hydrochloride used in Example 4, thereby obtaining the title compound (49.2 mg) as a yellow solid.

$^1$H-NMR (CDCl$_3$) δ: 4.04 (1H, dd, J=11.7, 4.6 Hz), 4.69 (1H, dd, J=11.7, 8.0 Hz), 5.03 (2H, s), 5.22 (1H, d, J=1.7 Hz), 5.44 (1H, d, J=1.7 Hz), 5.72-5.75 (1H, m), 6.34 (1H, d, J=13.0 Hz), 6.89 (1H, brs), 7.41 (1H, d, J=13.0 Hz), 7.63-7.65 (1H, m), 7.79-7.81 (1H, m), 7.81 (1H, d, J=8.0 Hz), 8.16 (1H, d, J=8.3 Hz), 8.25-8.26 (2H, m), 9.02 (1H, d, J=2.0 Hz).
ESI-MS m/z 417, 419[M+H]$^+$.

Example 6

(S,Z)—N-(4-amino-6-methylene-5-(quinolin-3-yl)-7,8-dihydro-6H-pyrimido[5,4-b]pyrrolizin-7-yl)-3-chloroacrylamide (Compound 6)

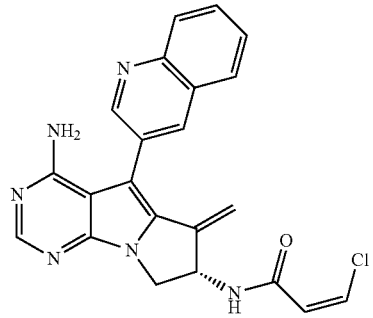 [SMILES: C=C1c2c(-c3cnc4ccccc4c3)c3c(N)ncnc3n2C[C@H]1NC(=O)/C=C\Cl]

The same synthesis as in Example 4 was performed using cis-3-chloroacrylic acid instead of the (E)-4-(dimethylamino)but-2-enoic acid hydrochloride used in Example 4, thereby obtaining the title compound (74.7 mg) as a yellow solid.

¹H-NMR (CDCl₃) δ: 4.07 (1H, dd, J=11.6, 5.4 Hz), 4.82 (1H, dd, J=11.6, 8.2 Hz), 4.96 (2H, s), 5.26 (1H, d, J=2.0 Hz), 5.48 (1H, d, J=2.0 Hz), 5.75-5.78 (1H, m), 6.28 (1H, d, J=8.3 Hz), 6.61 (1H, d, J=8.3 Hz), 6.81 (1H, d, J=7.3 Hz), 7.64-7.67 (1H, m), 7.79-7.83 (1H, m), 7.90 (1H, d, J=7.1 Hz), 8.19 (1H, d, J=8.5 Hz), 8.31 (1H, d, J=2.0 Hz), 8.33 (1H, s), 9.12 (1H, d, J=2.2 Hz).

ESI-MS m/z 417, 419[M+H]⁺.

Example 7

(S,E)-N-(4-amino-6-methylene-5-(quinolin-3-yl)-7,8-dihydro-6H-pyrimido[5,4-b]pyrrolizin-7-yl)-4-(piperidin-1-yl)but-2-enamide (Compound 7)

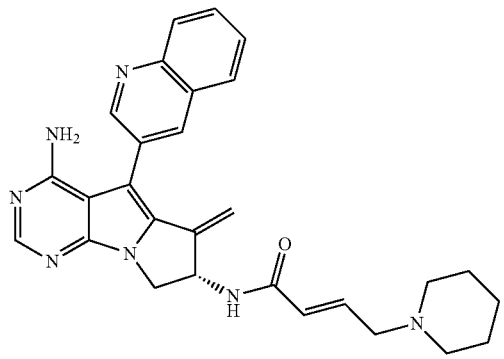 [SMILES: C=C1c2c(-c3cnc4ccccc4c3)c3c(N)ncnc3n2C[C@H]1NC(=O)/C=C/CN1CCCCC1]

The same synthesis as in Example 4 was performed using (E)-4-(piperidin-1-yl)but-2-enoic acid hydrochloride instead of the (E)-4-(dimethylamino)but-2-enoic acid hydrochloride used in Example 4, thereby obtaining the title compound (122 mg) as a yellow solid.

¹H-NMR (CDCl₃) δ: 1.42-1.59 (5H, m), 2.14 (1H, s), 2.39 (4H, brs), 3.10 (2H, dd, J=6.0, 1.4 Hz), 4.01 (1H, dd, J=11.6, 5.0 Hz), 4.69 (1H, dd, J=11.5, 8.0 Hz), 5.10 (2H, brs), 5.20 (1H, d, J=2.1 Hz), 5.43 (1H, d, J=2.1 Hz), 5.73-5.79 (1H, m), 6.06 (1H, dt, J=15.3, 1.4 Hz), 6.76 (1H, brs), 6.96 (1H, dt, J=15.3, 6.0 Hz), 7.62-7.64 (1H, m), 7.77-7.80 (1H, m), 7.87 (1H, d, J=8.0 Hz), 8.16 (1H, d, J=8.3 Hz), 8.24-8.25 (2H, m), 9.04 (1H, d, J=2.0 Hz).

ESI-MS m/z 480[M+H]⁺.

Example 8

(S)-N-(4-amino-6-methylene-5-(quinolin-3-yl)-7,8-dihydro-6H-pyrimido[5,4-b]pyrrolizin-7-yl)propiolamide (Compound 8)

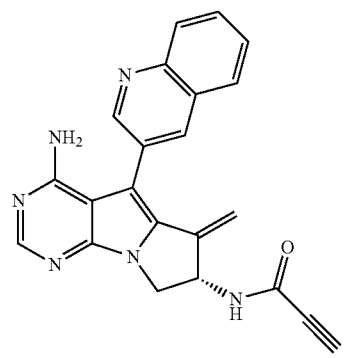 [SMILES: C#CC(=O)N[C@@H]1Cn2c(c(-c3cnc4ccccc4c3)c3c(N)ncnc32)C1=C]

The same synthesis as in Example 4 was performed using propiolic acid instead of the (E)-4-(dimethylamino)but-2-enoic acid hydrochloride used in Example 4, thereby obtaining the title compound (30.0 mg) as a yellow solid.

¹H-NMR (CDCl₃) δ: 2.91 (1H, s), 4.08 (1H, dd, J=11.7, 4.9 Hz), 4.76 (1H, dd, J=11.7, 8.0 Hz), 4.91 (2H, s), 5.24 (1H, d, J=1.2 Hz), 5.49 (1H, d, J=1.7 Hz), 5.68-5.69 (1H, m), 6.34-6.37 (1H, m), 7.65-7.67 (1H, m), 7.81-7.83 (1H, m), 7.90 (1H, d, J=8.3 Hz), 8.20 (1H, d, J=8.5 Hz), 8.30 (1H, d, J=2.0 Hz), 8.34 (1H, s), 9.11 (1H, d, J=2.2 Hz).

ESI-MS m/z 381[M+H]⁺.

Example 9

(S)-N-(4-amino-6-methylene-5-(quinolin-3-yl)-7,8-dihydro-6H-pyrimido[5,4-b]pyrrolizin-7-yl)but-2-ynamide (Compound 9)

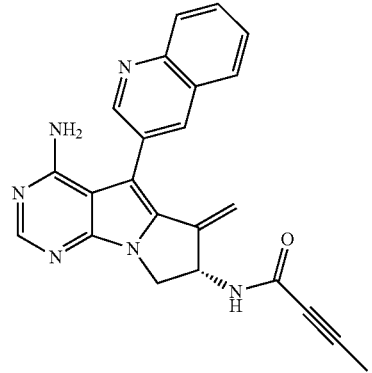 [SMILES: C=C1c2c(-c3cnc4ccccc4c3)c3c(N)ncnc3n2C[C@H]1NC(=O)C#CC]

The same synthesis as in Example 4 was performed using but-2-ynoic acid instead of the (E)-4-(dimethylamino)but-2-enoic acid hydrochloride used in Example 4, thereby obtaining the title compound (98.0 mg) as a yellow solid.

¹H-NMR (CDCl₃) δ: 1.96 (3H, s), 4.02 (1H, dd, J=11.6, 5.0 Hz), 4.70 (1H, dd, J=11.6, 8.3 Hz), 5.05 (2H, s), 5.24 (1H, d, J=1.6 Hz), 5.45 (1H, d, J=1.6 Hz), 5.70-5.72 (1H, m), 6.95-7.01 (1H, brs), 7.63-7.67 (1H, m), 7.78-7.83 (1H, m), 7.88 (1H, d, J=8.3 Hz), 8.21 (1H, d, J=8.5 Hz), 8.26-8.28 (2H, m), 9.02 (1H, d, J=2.0 Hz).

ESI-MS m/z 395[M+H]⁺.

Example 10

(S,E)-N-(4-amino-6-methylene-5-(quinolin-3-yl)-7,8-dihydro-6H-pyrimido[5,4-b]pyrrolizin-7-yl)-4-(diethylamino)but-2-enamide (Compound 10)

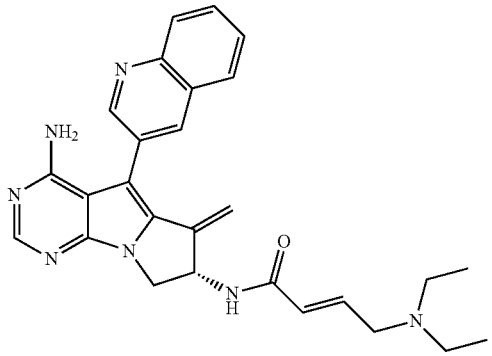 [SMILES: C=C1c2c(-c3cnc4ccccc4c3)c3c(N)ncnc3n2C[C@H]1NC(=O)/C=C/CN(CC)CC]

The same synthesis as in Example 4 was performed using (E)-4-(diethylamino)but-2-enoic acid hydrochloride instead of the (E)-4-(dimethylamino)but-2-enoic acid hydrochloride used in Example 4, thereby obtaining the title compound (38.2 mg) as a yellow solid.

¹H-NMR (CDCl₃) δ: 1.00 (6H, t, J=7.2 Hz), 2.51 (4H, q, J=7.2 Hz), 3.22 (2H, dd, J=5.9, 1.5 Hz), 4.00 (1H, dd, J=11.5, 4.9 Hz), 4.62 (1H, dd, J=11.5, 8.2 Hz), 5.22-5.24 (3H, m), 5.40 (1H, d, J=2.0 Hz), 5.74-5.80 (1H, m), 6.12 (1H, dt, J=15.4, 1.5 Hz), 6.98 (1H, dt, J=15.4, 5.9 Hz), 7.50 (1H, brs), 7.58-7.62 (1H, m), 7.74-7.78 (1H, m), 7.84 (1H, d, J=7.6 Hz), 8.12-8.14 (2H, m), 8.22 (1H, d, J=1.7 Hz), 8.99 (1H, d, J=2.0 Hz).
ESI-MS m/z 468[M+H]⁺.

Example 11

(S,E)-N-(4-amino-6-methylene-5-(quinolin-3-yl)-7,8-dihydro-6H-pyrimido[5,4-b]pyrrolizin-7-yl)-4-(ethyl(methyl)amino)but-2-enamide (Compound 11)

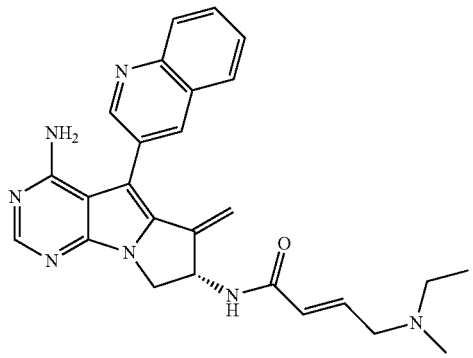 [SMILES: C=C1c2c(-c3cnc4ccccc4c3)c3c(N)ncnc3n2C[C@H]1NC(=O)/C=C/CN(C)CC]

The same synthesis as in Example 4 was performed using (E)-4-(ethyl(methyl)amino)but-2-enoic acid hydrochloride instead of the (E)-4-(dimethylamino)but-2-enoic acid hydrochloride used in Example 4, thereby obtaining the title compound (13.5 mg) as a yellow solid.

¹H-NMR (CDCl₃) δ: 1.06 (3H, t, J=7.2 Hz), 2.24 (3H, s), 2.44 (2H, q, J=7.2 Hz), 3.15 (2H, dd, J=6.0, 1.6 Hz), 4.03 (1H, dd, J=11.6, 5.1 Hz), 4.73 (1H, dd, J=11.6, 8.2 Hz), 5.01 (2H, s), 5.20 (1H, d, J=1.7 Hz), 5.44 (1H, d, J=1.7 Hz), 5.75-5.77 (1H, m), 6.05 (1H, dt, J=15.4, 1.6 Hz), 6.42 (1H, d, J=6.8 Hz), 6.96 (1H, dt, J=15.4, 6.0 Hz), 7.62-7.66 (1H, m), 7.78-7.82 (1H, m), 7.88 (1H, d, J=8.0 Hz), 8.18 (1H, d, J=8.5 Hz), 8.29 (2H, s), 9.08 (1H, d, J=2.2 Hz).
ESI-MS m/z 454[M+H]⁺.

Example 12

(S,E)-N-(4-amino-6-methylene-5-(quinolin-3-yl)-7,8-dihydro-6H-pyrimido[5,4-b]pyrrolizin-7-yl)-4-(isopropyl(methyl)amino)but-2-enamide (Compound 12)

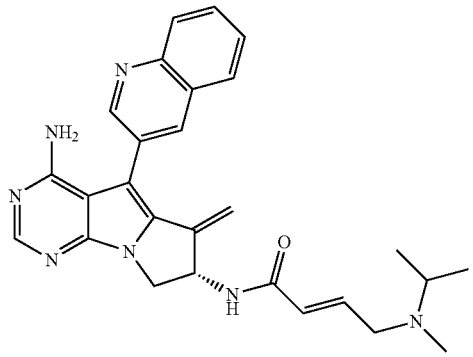 [SMILES: C=C1c2c(-c3cnc4ccccc4c3)c3c(N)ncnc3n2C[C@H]1NC(=O)/C=C/CN(C)C(C)C]

The same synthesis as in Example 4 was performed using (E)-4-(isopropyl(methyl)amino)but-2-enoic acid hydrochloride instead of the (E)-4-(dimethylamino)but-2-enoic acid hydrochloride used in Example 4, thereby obtaining the title compound (25.8 mg) as a yellow solid.

¹H-NMR (CDCl₃) δ: 1.00 (6H, d, J=6.6 Hz), 2.15-2.36 (3H, m), 2.79-2.88 (1H, m), 3.18 (2H, dd, J=5.9, 1.5 Hz), 4.01 (1H, dd, J=11.5, 5.0 Hz), 4.70 (1H, dd, J=11.5, 8.0 Hz), 5.11 (2H, s), 5.21 (1H, d, J=1.8 Hz), 5.43 (1H, d, J=1.8 Hz), 5.73-5.79 (1H, m), 6.10 (1H, dt, J=15.4, 1.5 Hz), 6.74 (1H, brs), 6.94 (1H, dt, J=15.4, 5.9 Hz), 7.61-7.65 (1H, m), 7.77-7.81 (1H, m), 7.87 (1H, d, J=8.5 Hz), 8.16 (1H, d, J=8.8 Hz), 8.23-8.26 (2H, m), 9.05 (1H, d, J=2.2 Hz). ESI-MS m/z 468[M+H]⁺.

Example 13

(R)-N-(4-amino-6-methylene-5-(quinolin-3-yl)-6,7,8,9-tetrahydropyrimido[5,4-b]indolizin-7-yl)acrylamide (Compound 13)

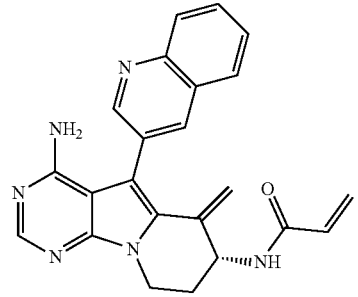 [SMILES: C=CC(=O)N[C@@H]1CCn2c(c(-c3cnc4ccccc4c3)c3c(N)ncnc32)C1=C]

Step 1: Synthesis of (R)-tert-butyl (1-hydroxy-5-(methylthio)pentan-3-yl)carbamate

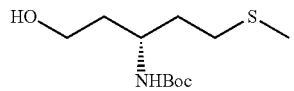 [SMILES: CSCC[C@@H](CCO)NC(=O)OC(C)(C)C]

N-methylmorpholine (3.63 ml) and ethyl chloroformate (3.01 ml) were added to a solution of (R)-3-((tert-butoxycarbonyl)amino)-5-(methylthio)pentanoic acid (7.92 g) in THF (79.2 ml) at −10° C. After stirring at −10° C. for 15 minutes, the generated insoluble matter was filtered off. An aqueous solution of sodium borohydride (1.55 g) (15 ml) was added to the filtrate at −10° C., and the mixture was stirred at −10° C. for 1 hour. A saturated aqueous ammonium chloride solution was added to the reaction mixture, and the mixture was stirred at room temperature for 30 minutes. Ethyl acetate was added to the reaction mixture to separate the organic layer. The organic layer was washed with a 0.5 N aqueous potassium hydrogen sulfate solution, water, a 0.5 N aqueous sodium hydroxide solution, and a saturated sodium chloride solution, and dried over anhydrous sodium sulfate. The solvent was then distilled off under reduced pressure. The resulting residue was purified by silica gel column chromatography (developing solvent: chloroform/ethyl acetate), thereby obtaining the title compound as a light-yellow, oily substance (7.18 g).

Step 2: Synthesis of tert-butyl ((3R)-1-hydroxy-5-(methylsulfinyl)pentan-3-yl)carbamate

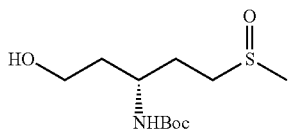 [SMILES: CS(=O)CC[C@@H](CCO)NC(=O)OC(C)(C)C]

A suspension of sodium periodate (7.0 g) in water (32 ml) was added to a solution of the (R)-tert-butyl (1-hydroxy-5-(methylthio)pentan-3-yl)carbamate (8.16 g) obtained in Step 1 in methanol (98 ml) at a temperature 10° C. or lower, and the mixture was stirred at room temperature for 2 hours. The generated insoluble matter was filtered off, and the filtrate was distilled off under reduced pressure. The resulting residue was dissolved in a saturated sodium chloride solution, followed by extraction with chloroform 3 times. The organic layer was dried over anhydrous sodium sulfate, and the solvent was distilled off under reduced pressure, thereby obtaining the title compound (9.38 g) as a light-yellow solid.

Step 3: Synthesis of (R)-tert-butyl (5-hydroxypent-1-en-3-yl)carbamate

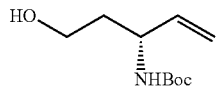

Sodium acetate (13.45 g) was added to a solution of the tert-butyl ((3R)-1-hydroxy-5-(methylsulfinyl)pentan-3-yl)carbamate (9.38 g) obtained in Step 2 in 1,2-dichlorobenzene (140 ml) at room temperature. The mixture was stirred at an internal temperature of 166° C. for 18 hours. After cooling the reaction mixture, the insoluble matter was filtered off, and 1,2-dichlorobenzene was distilled off under reduced pressure. The resulting residue was dissolved in ethyl acetate, washed with a sodium hypochlorite aqueous solution, water, and a saturated sodium chloride solution, and dried over anhydrous sodium sulfate. The solvent was then distilled off under reduced pressure. The resulting residue was purified by silica gel column chromatography (developing solvent: hexane/ethyl acetate), thereby obtaining the title compound (2.50 g) as a light-yellow, oily substance.

Step 4: Synthesis of (R)-tert-butyl (5-(4-chloro-5-iodo-7H-pyrrolo[2,3-d]pyrimidin-7-yl)pent-1-en-3-yl)carbamate

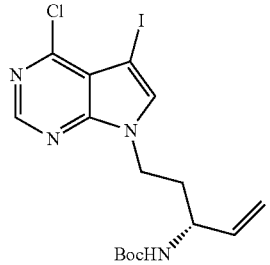 [SMILES: C=C[C@@H](CCn1cc(I)c2c(Cl)ncnc21)NC(=O)OC(C)(C)C]

Triphenylphosphine (3.25 g) was added to and dissolved in a solution of the (R)-tert-butyl (5-hydroxypent-1-en-3-yl)carbamate (2.5 g) obtained in Step 3 and 4-chloro-5-iodo-7H-pyrrolo[2,3-d]pyrimidine (2.31 g) in DME (23 ml) under ice-cooling. Thereafter, diisopropyl azodicarboxylate (2.44 ml) was gradually added. The reaction mixture was stirred under ice-cooling for 30 minutes, and at room temperature for 1 hour, and the solvent was then distilled off under reduced pressure. The resulting residue was dissolved in ethyl acetate, washed with water, and dried over anhydrous sodium sulfate. The solvent was then distilled off under reduced pressure. The resulting residue was purified by silica gel column chromatography (developing solvent: hexane/ethyl acetate), thereby obtaining the title compound (3.49 g) as a light-yellow solid.
ESI-MS m/z 463, 465 [M+H]$^+$.

Step 5: Synthesis of (R)-tert-butyl (5-(4-amino-5-iodo-7H-pyrrolo[2,3-d]pyrimidin-7-yl)pent-1-en-3-yl)carbamate

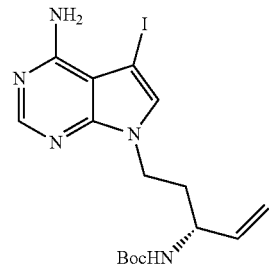 [SMILES: C=C[C@@H](CCn1cc(I)c2c(N)ncnc21)NC(=O)OC(C)(C)C]

28% aqueous ammonia (17.5 ml) was added to a solution of the (R)-tert-butyl (5-(4-chloro-5-iodo-7H-pyrrolo[2,3-d]pyrimidin-7-yl)pent-1-en-3-yl)carbamate (3.49 g) obtained in Step 4 in DME (17.5 ml), and the mixture was stirred in an autoclave at an internal temperature of 105° C. for 8 hours. After cooling the reaction mixture, water (70 ml) was added, and the mixture was stirred at room temperature for 4 hours. The resulting precipitate was collected by filtration, washed with water, and dried, thereby obtaining the title compound (3.20 g) as a light-yellow solid.
ESI-MS m/z 444 [M+H]$^+$.

Step 6: Synthesis of (R)-tert-butyl (5-(4-amino-5-(quinolin-3-yl)-7H-pyrrolo[2,3-d]pyrimidin-7-yl)pent-1-en-3-yl)carbamate

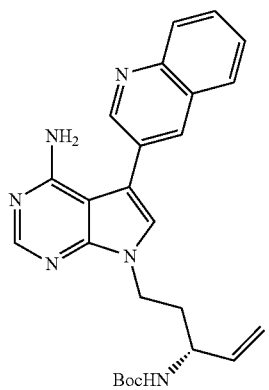 [SMILES: C=C[C@@H](CCn1cc(-c2cnc3ccccc3c2)c2c(N)ncnc21)NC(=O)OC(C)(C)C]

A mixture of the (R)-tert-butyl (5-(4-amino-5-iodo-7H-pyrrolo[2,3-d]pyrimidin-7-yl)pent-1-en-3-yl)carbamate (3.2 g) obtained in Step 5, 3-quinolineboronic acid (1.37 g), sodium carbonate (843 mg), tetrakis(triphenylphosphine) palladium (250 mg), DME (32 ml) and water (32 ml) was stirred under a nitrogen atmosphere at 100° C. for 6 hours. After cooling the reaction mixture, a saturated aqueous sodium bicarbonate solution and ethyl acetate were added.

The resulting mixture was stirred at room temperature for 30 minutes. After filtering off the insoluble matter, the organic layer was separated and dried over anhydrous sodium sulfate. The solvent was then distilled off under reduced pressure. The resulting residue was purified by silica gel column chromatography (developing solvent: hexane/ethyl acetate, ethyl acetate/methanol), thereby obtaining the title compound (3.21 g) as a light-orange solid.

ESI-MS m/z 445 [M+H]⁺.

Step 7: Synthesis of (R)-tert-butyl (5-(4-amino-6-bromo-5-(quinolin-3-yl)-7H-pyrrolo[2,3-d]pyrimidin-7-yl)pent-1-en-3-yl)carbamate

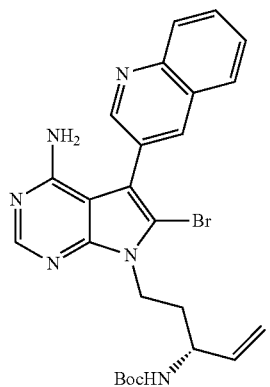 [SMILES: C=C[C@@H](CCn1c(Br)c(-c2cnc3ccccc3c2)c2c(N)ncnc21)NC(=O)OC(C)(C)C]

A solution of N-bromosuccinimide (1.35 g) in THF (23 ml) was added to a solution of the (R)-tert-butyl (5-(4-amino-5-(quinolin-3-yl)-7H-pyrrolo[2,3-d]pyrimidin-7-yl)pent-1-en-3-yl)carbamate (3.21 g) obtained in Step 6 in THF (26 ml) under ice-cooling over 30 minutes. The mixture was stirred under ice-cooling for 30 minutes. After adding a 5% aqueous sodium thiosulfate solution to the reaction mixture, the mixture was poured into a saturated aqueous sodium bicarbonate solution, followed by extraction with ethyl acetate. The organic layer was washed with a saturated sodium chloride solution, and dried over anhydrous sodium sulfate. The solvent was then distilled off under reduced pressure. The resulting residue was purified by silica gel column chromatography (developing solvent: hexane/ethyl acetate, ethyl acetate/methanol), thereby obtaining the title compound (3.15 g) as a light-brown solid.

ESI-MS m/z 523, 525 [M+H]⁺.

Step 8: Synthesis of (R)-tert-butyl (4-amino-6-methylene-5-(quinolin-3-yl)-6,7,8,9-tetrahydropyrimido[5,4-b]indolizin-7-yl)carbamate

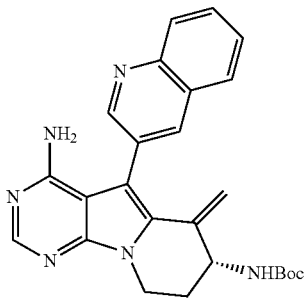 [SMILES: C=C1c2c(-c3cnc4ccccc4c3)c3c(N)ncnc3n2CC[C@H]1NC(=O)OC(C)(C)C]

A 4 N sodium hydroxide aqueous solution (0.454 ml) was added to a solution of the (R)-tert-butyl (5-(4-amino-6-bromo-5-(quinolin-3-yl)-7H-pyrrolo[2,3-d]pyrimidin-7-yl)pent-1-en-3-yl)carbamate (475 mg) obtained in Step 7 in THF (5 ml). Thereafter, the mixture was degassed under reduced pressure, followed by nitrogen purging. After tetrakis(triphenylphosphine)palladium (41.6 mg) was added, the mixture was stirred overnight while being heated under reflux. After the reaction mixture was cooled to room temperature, the reaction mixture was poured into water, and extracted with ethyl acetate. The resulting organic layer was washed with a saturated sodium chloride solution, and dried over anhydrous sodium sulfate. After filtration and concentration, the resulting residue was purified by silica gel chromatography (developing solvent: ethyl acetate/methanol), thereby obtaining the title compound (293 mg) as a yellow solid.

ESI-MS m/z 443 [M+H]⁺.

Step 9: Synthesis of (R)-6-methylene-5-(quinolin-3-yl)-6,7,8,9-tetrahydropyrimido[5,4-b]indolizin-4,7-diamine

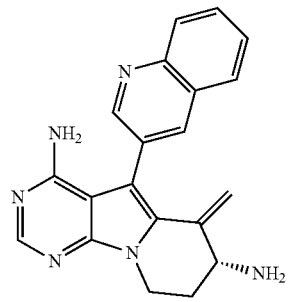 [SMILES: C=C1c2c(-c3cnc4ccccc4c3)c3c(N)ncnc3n2CC[C@H]1N]

5 N hydrochloric acid (1 ml) was added to a solution of the (R)-tert-butyl (4-amino-6-methylene-5-(quinolin-3-yl)-6,7,8,9-tetrahydropyrimido[5,4-b]indolizin-7-yl)carbamate (290 mg) obtained in Step 8 in ethanol (4 ml). Thereafter, the mixture was stirred for 6 hours at 70° C. After the reaction mixture was cooled to room temperature, the reaction mixture was adjusted to about pH 10 using a 5 N sodium hydroxide aqueous solution, followed by extraction with chloroform. The resulting organic layer was dried over anhydrous sodium sulfate, followed by filtration and concentration. The resulting residue was purified by basic silica gel chromatography (developing solvent: chloroform/methanol), thereby obtaining the title compound (218 mg) as a light-brown solid.

ESI-MS m/z 343 [M+H]⁺.

Step 10: Synthesis of Compound 13

Diisopropylethylamine (0.129 ml) and a solution of acryloyl chloride (56.1 mg) in chloroform (0.5 ml) were added to a solution of the (R)-6-methylene-5-(quinolin-3-yl)-6,7,8,9-tetrahydropyrimido[5,4-b]indolizin-4,7-diamine (215 mg) obtained in Step 9 in chloroform (4 ml) under ice-cooling, and the resulting mixture was stirred for 30 minutes. After the reaction mixture was concentrated, the residue was purified by silica gel chromatography (developing solvent: ethyl acetate/methanol), thereby obtaining the title compound (117 mg) as a yellow solid.

¹H-NMR (CDCl₃) δ: 2.28-2.41 (2H, m), 4.32-4.50 (2H, m), 4.64 (2H, brs), 4.97 (1H, s), 5.07 (1H, s), 5.05-5.12 (1H, m), 5.72 (1H, dd, J=10.2, 1.2 Hz), 5.75-5.85 (1H, m), 6.14 (1H, dd, J=16.8, 10.2 Hz), 6.36 (1H, dd, J=16.8, 1.2 Hz), 7.61-7.68 (1H, m), 7.77-7.84 (1H, m), 7.87 (1H, d, J=8.4 Hz), 8.18 (1H, d, J=8.4 Hz), 8.2'1 (1H, d, J=2.0 Hz), 8.33 (1H, s), 8.98 (1H, d, J=2.0 Hz).

ESI-MS m/z 397[M+H]$^+$.

Example 14

(S)—N-(4-amino-6-methyl-5-(quinolin-3-yl)-8,9-dihydropyrimido[5,4-b]indolizin-8-yl)acrylamide (Compound 14)

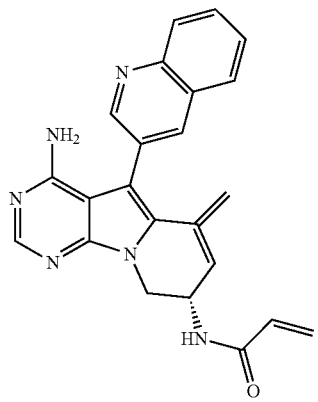

Step 1: Synthesis of (S)-methyl 2-((tert-butoxycarbonyl)amino)pent-4-enoate

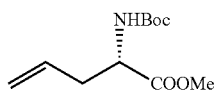

5 N sodium hydroxide aqueous solution (2.1 ml) and di-tert-butyl dicarbonate (2.128 ml) were added to a suspension of (S)-2-amino-4-pentenoic acid (1.016 g) in methanol (20 ml) at room temperature, and the resulting mixture was stirred for 8 hours at the same temperature. Di-tert-butyl dicarbonate (0.304 ml) was added at room temperature, and the mixture was stirred for 1 hour at the same temperature. 4-hydroxy-1H-benzotriazole (1.796 g) and 1-(3-dimethylaminopropyl)-3-ethylcarbodiimide hydrochloride (3.882 g) were added to the reaction mixture at room temperature, and the mixture was stirred overnight at the same temperature. The reaction mixture was concentrated under reduced pressure, and then was poured into a saturated aqueous sodium bicarbonate solution, followed by extraction with ethyl acetate. The resulting organic layer was dried over anhydrous sodium sulfate, followed by filtration and concentration. The resulting residue was purified by silica gel chromatography (developing solvent: chloroform/methanol), thereby obtaining the title compound (2.0311 g) as a light-yellow, oily substance.

Step 2: Synthesis of (S)-tert-butyl (1-hydroxypent-4-en-2-yl)carbamate

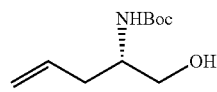

Lithium aluminium hydride (668.2 mg) was added to a solution of the (S)-methyl2-((tert-butoxycarbonyl)amino)pent-4-enoate (1.983 g) obtained in Step 1 in THF (50 ml) under ice cooling, and the mixture was stirred for 1.5 hours at the same temperature. Sodium sulfate decahydrate (1.1375 g) and THF (10 ml) were added to the reaction mixture at room temperature, and the mixture was stirred overnight at the same temperature. The insoluble matter was filtered off. After washing with THF and ethyl acetate, the filtrate was concentrated under reduced pressure. The resulting residue was purified by silica gel chromatography (developing solvent: hexane/ethyl acetate), thereby obtaining the title compound (1.2601 g) as a light-yellow, oily substance.

Step 3: Synthesis of (S)-tert-butyl (1-(4-chloro-5-iodo-7H-pyrrolo[2,3-d]pyrimidin-7-yl)pent-4-en-2-yl)carbamate

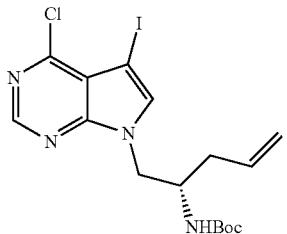 [SMILES: C=CC[C@@H](Cn1cc(I)c2c(Cl)ncnc21)NC(=O)OC(C)(C)C]

The same synthesis as in Step 4 of Example 13 was performed using the (S)-tert-butyl (1-hydroxypent-4-en-2-yl)carbamate obtained in Step 2 instead of the (R)-tert-butyl (5-hydroxypent-1-en-3-yl)carbamate used in Step 4 of Example 13, thereby obtaining the title compound (2.7679 g) as a light-yellow solid.

ESI-MS m/z 463, 465 [M+H]$^+$.

Step 4: Synthesis of (S)-tert-butyl (1-(4-amino-6-bromo-5-(quinolin-3-yl)-7H-pyrrolo[2,3-d]pyrimidin-7-yl)pent-4-en-2-yl)carbamate

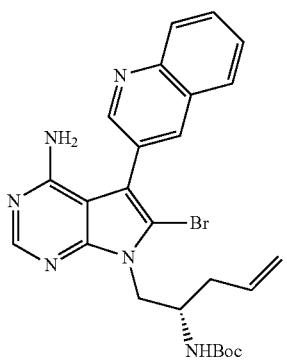 [SMILES: C=CC[C@@H](Cn1c(Br)c(-c2cnc3ccccc3c2)c2c(N)ncnc21)NC(=O)OC(C)(C)C]

The same synthesis as in Steps 5 to 7 of Example 13 was performed using the (S)-tert-butyl (1-(4-chloro-5-iodo-7H-pyrrolo[2,3-d]pyrimidin-7-yl)pent-4-en-2-yl)carbamate obtained in Step 3 instead of the (R)-tert-butyl (5-(4-chloro- 5-iodo-7H-pyrrolo[2,3-d]pyrimidin-7-yl)pent-1-en-3-yl) carbamate used in Step 5 of Example 13, thereby obtaining the title compound (2.669 g) as a light-brown solid.

ESI-MS m/z 523, 525 [M+H]⁺.

Step 5: Synthesis of (S)-tert-butyl (4-amino-6-methyl-5-(quinolin-3-yl)-8,9-dihydropyrimido[5,4-b]indolizin-8-yl)carbamate and (S)-tert-butyl (4-amino-6-methylene-5-(quinolin-3-yl)-6,7,8,9-tetrahydropyrimido[5,4-b]indolizin-8-yl)carbamate

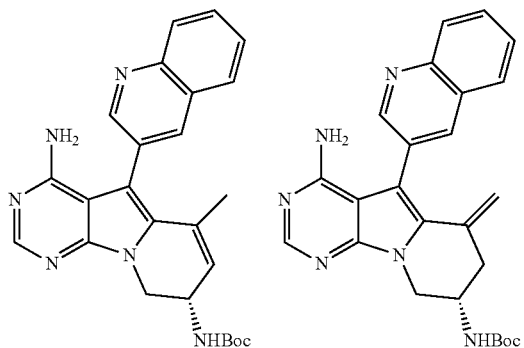

A 4 N sodium hydroxide aqueous solution (5.1 ml) and tetrakis(triphenylphosphine)palladium (235.4 mg) were added to a solution of the (S)-tert-butyl (1-(4-amino-6-bromo-5-(quinolin-3-yl)-7H-pyrrolo[2,3-d]pyrimidin-7-yl)pent-4-en-2-yl)carbamate (2.669 g) obtained in Step 4 in THF (50 ml), and the mixture was degassed under reduced pressure, followed by nitrogen purging. The reaction mixture was stirred overnight while being heated under reflux. After the reaction mixture was cooled to room temperature, the reaction mixture was poured into a saturated aqueous sodium bicarbonate solution, and extracted with ethyl acetate. The resulting organic layer was dried over anhydrous sodium sulfate. After filtration and concentration, the resulting residue was purified by silica gel chromatography (developing solvent: chloroform/methanol), thereby obtaining a mixture of the title compound (2.427 g) as a yellow solid.

ESI-MS m/z 443 [M+H]⁺.

Step 6: Synthesis of (S)-6-methyl-5-(quinolin-3-yl)-8,9-dihydropyrimido[5,4-b]indolizin-4,8-diamine and (S)-6-methylene-5-(quinolin-3-yl)-6,7,8,9-tetrahydropyrimido[5,4-b]indolizin-4,8-diamine

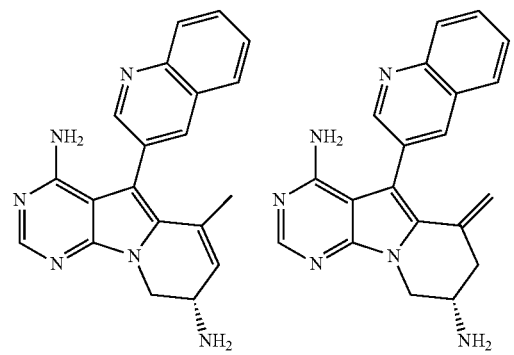

5 N hydrochloric acid (5.1 ml) was added to a solution of a mixture (2.427 g) of the (S)-tert-butyl (4-amino-6-methyl-5-(quinolin-3-yl)-8,9-dihydropyrimido[5,4-b]indolizin-8-yl)carbamate and (S)-tert-butyl (4-amino-6-methylene-5-(quinolin-3-yl)-6,7,8,9-tetrahydropyrimido[5,4-b]indolizin-8-yl)carbamate obtained in Step 5 in ethanol (20 ml), and the mixture was stirred overnight at 60° C. After an additional 5 N hydrochloric acid (5.1 ml) was added, the mixture was stirred for 10 hours while being heated under reflux. After the reaction mixture was cooled to room temperature, the reaction mixture was diluted with water, and washed with chloroform. A 5 N sodium hydroxide aqueous solution (10 ml) was added to the aqueous layer, followed by extraction with chloroform. The resulting organic layer was dried over anhydrous sodium sulfate, followed by filtration and concentration. The resulting residue was purified by basic silica gel chromatography (developing solvent: ethyl acetate/methanol), thereby obtaining a mixture of the title compound (1.4098 g) as a light-yellow solid.

ESI-MS m/z 343 [M+H]⁺.

Step 7: Synthesis of Compound 14

Diisopropylethylamine (0.8452 ml) and a solution of acryloyl chloride (0.35 ml) in acetonitrile (3.5 ml) were successively added to a solution of a mixture (1.407 g) of the (S)-6-methyl-5-(quinolin-3-yl)-8,9-dihydropyrimido[5,4-b]indolizin-4,8-diamine and (S)-6-methylene-5-(quinolin-3-yl)-6,7,8,9-tetrahydropyrimido[5,4-b]indolizin-4, 8-diamine obtained in Step 6 in acetonitrile (10 ml) and water (10 ml) at 0° C., and the mixture was stirred for 45 minutes at the same temperature. After the reaction mixture was diluted with water, the reaction mixture was poured into a saturated aqueous sodium bicarbonate solution, followed by extraction with ethyl acetate. After the organic layer was dried over anhydrous sodium sulfate, the solvent was distilled off under reduced pressure. The resulting residue was purified by silica gel column chromatography (developing solvent: ethyl acetate/methanol), thereby obtaining the title compound (897.1 mg) as a light-yellow solid.

¹H-NMR (DMSO-d₆) δ: 1.51 (3H, s), 4.17 (1H, dd, J=13.2, 5.1 Hz), 4.25 (1H, dd, J=13.2, 5.1 Hz), 4.73-4.83 (1H, m), 5.61 (1H, dd, J=9.8, 2.7 Hz), 5.65-6.00 (2H, brs), 5.81 (1H, dd, J=5.1, 1.2 Hz), 6.14 (1H, dd, J=17.1, 2.4 Hz), 6.24 (1H, dd, J=17.1, 9.8 Hz), 7.67 (1H, ddd, J=8.1, 7.1, 1.0 Hz), 7.81 (1H, ddd, J=8.3, 7.1, 1.5 Hz), 8.05 (1H, d, J=8.1 Hz), 8.09 (1H, d, J=8.3 Hz), 8.13 (1H, s), 8.39 (1H, brs), 8.46 (1H, d, J=7.3 Hz), 8.94 (1H, s).

ESI-MS m/z 397[M+H]⁺.

Example 15

(S)—N-(4-amino-6-methylene-5-(quinolin-3-yl)-6,7,8,9-tetrahydropyrimido[5,4-b]indolizin-8-yl) acrylamide (Compound 15)

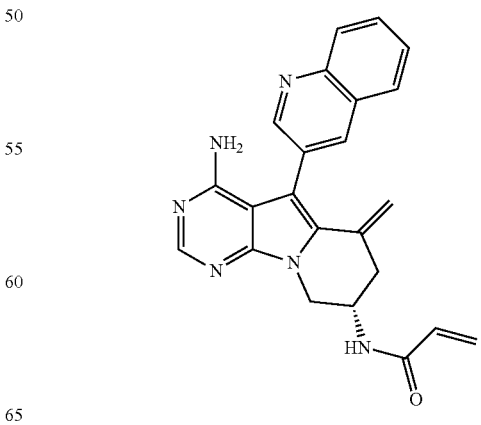

The mixed fraction obtained by the silica gel column chromatography purification in Step 7 of Example 14 was purified by reversed-phase preparative HPLC, thereby obtaining the title compound (32.2 mg) as a light-yellow solid.

¹H-NMR (DMSO-d₆) δ: 2.56-2.70 (1H, m), 2.72-2.82 (1H, m), 4.19 (1H, dd, J=14.1, 8.3 Hz), 4.25-4.36 (1H, m), 4.72 (1H, d, J=13.7 Hz), 5.62 (1H, dd, J=10.0, 2.2 Hz), 5.80 (1H, dt, J=12.2, 4.6 Hz), 6.00-6.20 (3H, m), 6.20-6.31 (2H, m), 7.65 (1H, t, J=8.1 Hz), 7.80 (1H, t, 8.3 Hz), 8.05 (1H, d, J=8.5 Hz), 8.08 (1H, d, J=8.3 Hz), 8.15 (1H, s), 8.28-8.39 (2H, m), 8.87 (1H, d, J=2.2 Hz).

ESI-MS m/z 397[M+H]⁺.

Example 16

(R)—N-(4-amino-6-methyl-5-(quinolin-3-yl)-8,9-dihydropyrimido[5,4-b]indolizin-8-yl)acrylamide (Compound 16)

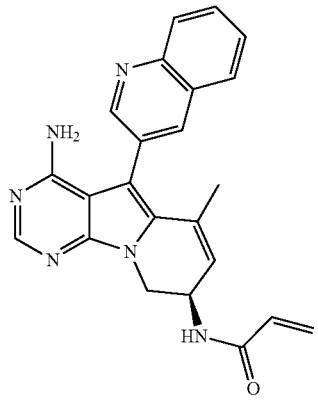 [SMILES: C=CC(=O)N[C@@H]1C=C(C)c2c(-c3cnc4ccccc4c3)c3c(N)ncnc3n2C1]

Step 1: Synthesis of (R)-tert-butyl (1-(4-chloro-5-iodo-7H-pyrrolo[2,3-d]pyrimidin-7-yl)pent-4-en-2-yl)carbamate

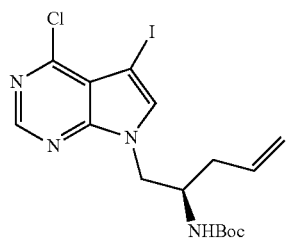 [SMILES: C=CC[C@H](Cn1cc(I)c2c(Cl)ncnc21)NC(=O)OC(C)(C)C]

The same synthesis as in Steps 1 to 3 of Example 14 was performed using (R)-2-amino-4-pentenoic acid instead of the (S)-2-amino-4-pentenoic acid used in Step 1 of Example 14, thereby obtaining the title compound (1.4217 g) as a light-yellow solid.

ESI-MS m/z 463, 465 [M+H]⁺.

Step 2: Synthesis of Compound 16

The same synthesis as in Steps 4 to 7 of Example 14 was performed using the (R)-tert-butyl (1-(4-chloro-5-iodo-7H-pyrrolo[2,3-d]pyrimidin-7-yl)pent-4-en-2-yl)carbamate obtained in Step 1, thereby obtaining the title compound (21.0 mg) as a light-yellow solid.

¹H-NMR (DMSO-d₆) δ: 1.51 (3H, s), 4.17 (1H, dd, J=13.2, 5.1 Hz), 4.25 (1H, dd, J=13.2, 5.1 Hz), 4.73-4.83 (1H, m), 5.61 (1H, dd, J=9.8, 2.7 Hz), 5.65-6.00 (2H, brs), 5.81 (1H, dd, J=5.1, 1.2 Hz), 6.14 (1H, dd, J=17.1, 2.4 Hz), 6.24 (1H, dd, J=17.1, 9.8 Hz), 7.67 (1H, t, J=7.1 Hz), 7.81 (1H, t, J=7.6 Hz), 8.05 (1H, d, J=8.1 Hz), 8.09 (1H, d, J=8.6 Hz), 8.13 (1H, s), 8.39 (1H, brs), 8.46 (1H, d, J=7.1 Hz), 8.94 (1H, s).

ESI-MS m/z 397[M+H]⁺.

Example 17

(R)—N-(4-amino-6-methylene-5-(quinolin-3-yl)-6,7,8,9-tetrahydropyrimido[5,4-b]indolizin-8-yl)acrylamide (Compound 17)

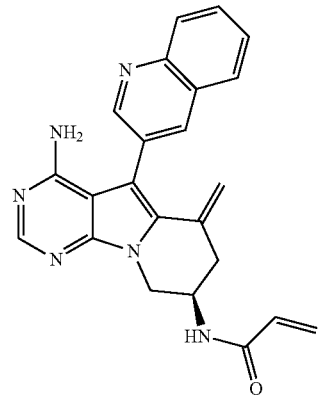 [SMILES: C=CC(=O)N[C@@H]1CC(=C)c2c(-c3cnc4ccccc4c3)c3c(N)ncnc3n2C1]

The mixed fraction obtained by the silica gel column chromatography purification in Example 16 was purified in the same method as in Example 15, thereby obtaining the title compound (8.4 mg) as a light-yellow solid.

¹H-NMR (DMSO-d₆) δ: 2.57-2.70 (1H, m), 2.71-2.82 (1H, m), 4.19 (1H, dd, J=13.2, 8.3 Hz), 4.25-4.36 (1H, m), 4.72 (1H, d, J=13.2 Hz), 5.62 (1H, dd, J=10.0, 2.2 Hz), 5.80 (1H, dt, J=12.2, 4.6 Hz), 6.00-6.20 (3H, m), 6.20-6.31 (2H, m), 7.65 (1H, t, J=7.6 Hz), 7.79 (1H, ddd, J=8.3, 7.1, 1.5 Hz), 8.05 (1H, d, J=8.5 Hz), 8.08 (1H, d, J=8.5 Hz), 8.15 (1H, s), 8.33 (1H, d, J=2.2 Hz), 8.36 (1H, d, J=7.6 Hz), 8.87 (1H, d, J=2.2 Hz).

ESI-MS m/z 397[M+H]⁺.

Example 18

(S)—N-(4-amino-6-methylene-5-(quinolin-3-yl)-7,8,9,10-tetrahydro-6H-pyrimido[5',4':4,5]pyrrolo[1,2-a]azepin-8-yl)acrylamide (Compound 18)

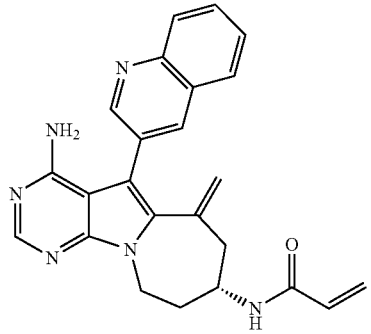 [SMILES: C=CC(=O)N[C@@H]1CCn2c(c(-c3cnc4ccccc4c3)c3c(N)ncnc32)C(=C)C1]

Step 1: Synthesis of (S)-tert-butyl (1-hydroxyhex-5-en-3-yl)carbamate

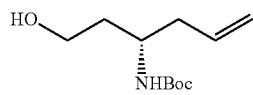

N-methylmorpholine (2.1 g) was added to a solution of (S)-3-((tert-butoxycarbonyl)amino)hex-5-enoic acid (4.0 g) in THF (40 ml), and ethyl chloroformate (1.75 ml) was gradually added at −10° C. Thereafter, the mixture was stirred for 20 minutes at the same temperature, and the generated insoluble matter was filtered through Celite. A solution of sodium tetrahydroborate (904 mg) in water (8 ml) was gradually added to the resulting filtrate at −10° C. After the mixture was stirred for 30 minutes at the same temperature, a saturated aqueous ammonium chloride solution was added. After extraction with ethyl acetate, washing was performed using a 0.5 N potassium hydrogen sulfate aqueous solution, a saturated aqueous sodium bicarbonate solution, and a saturated sodium chloride solution in this order. The resulting organic layer was dried over anhydrous sodium sulfate and then filtered, followed by concentration. The resulting residue was purified by silica gel chromatography (developing solvent: hexane/ethyl acetate), thereby obtaining the title compound (3.54 g) as an oily substance.

Step 2: Synthesis of Compound 18

The same synthesis as in Steps 4 to 10 of Example 13 was performed using the (S)-tert-butyl (1-hydroxyhex-5-en-3-yl) carbamate obtained in Step 1 instead of the (R)-tert-butyl (5-hydroxypent-1-en-3-yl)carbamate used in Step 4 of Example 13, thereby obtaining the title compound (147 mg) as a colorless solid.

$^1$H-NMR (DMSO-d$_6$) δ: 1.68-1.82 (1H, m), 2.17-2.25 (1H, m), 2.42-2.53 (1H, m), 2.75-2.83 (1H, m), 3.86-4.16 (2H, m), 4.64-4.78 (1H, m), 4.84 (1H, d, J=1.7 Hz), 5.26 (1H, s), 5.60 (1H, dd, J=10.0, 2.4 Hz), 6.00 (2H, brs), 6.11 (1H, dd, J=17.1, 2.4 Hz), 6.27 (1H, dd, J=17.1, 10.0 Hz), 7.60-7.64 (1H, m), 7.73-7.77 (1H, m), 7.99-8.04 (2H, m), 8.17 (1H, s), 8.22 (1H, d, J=8.0 Hz), 8.30 (1H, d, J=2.0 Hz), 8.78 (1H, d, J=2.0 Hz).

ESI-MS m/z 411[M+H]$^+$.

Example 19

(S,E)-N-(4-amino-6-ethylidene-5-(quinolin-3-yl)-6,7,8,9-tetrahydropyrimido[5,4-b]indolizin-8-yl)acrylamide (Compound 19)

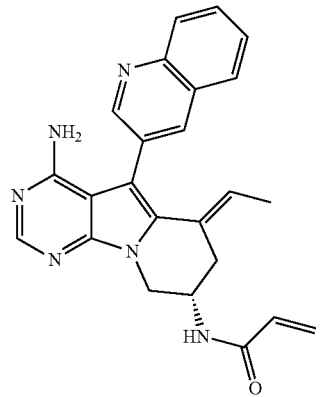 [SMILES: C=CC(=O)N[C@H]1C/C(=C\C)c2c(-c3cnc4ccccc4c3)c3c(N)ncnc3n2C1]

Step 1: Synthesis of (S)-methyl 3-((tert-butoxycarbonyl)amino)-4-hydroxybutanoate

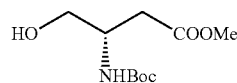

N-methylmorpholine (9.78 ml) and ethyl chloroformate (8.09 ml) were added to a solution of (S)-2-((tert-butoxycarbonyl)amino)-4-methoxy-4-oxobutanoic acid (20.0 g) in THF (200 ml) under ice-cooling, and the mixture was stirred for 1 hour under ice-cooling. The generated insoluble matter was filtered off. A solution of sodium borohydride (4.14 g) in water (41.4 ml) was added to the filtrate under ice-cooling, and the mixture was stirred for 30 minutes under ice-cooling. A 0.5 N potassium hydrogen sulfate aqueous solution and ethyl acetate were added to the reaction mixture. The organic layer was separated, washed with a saturated aqueous sodium bicarbonate solution and a saturated sodium chloride solution, and dried over anhydrous magnesium sulfate. The solvent was then distilled off under reduced pressure, thereby obtaining the title compound (10.82 g).

Step 2: Synthesis of (S)-tert-butyl 4-(2-methoxy-2-oxoethyl)-2,2-dimethyloxazolidine-3-carboxylate

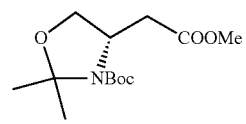

2,2-dimethoxypropane (28.52 ml) and boron trifluoride-diethylether complex (0.294 ml) were added to a solution of the (S)-methyl 3-((tert-butoxycarbonyl)amino)-4-hydroxybutanoate (10.82 g) obtained in Step 1 in acetone (108.2 ml) at room temperature, and the mixture was stirred for 4 hours at the same temperature. The reaction mixture was poured into a saturated aqueous sodium bicarbonate solution, and extracted with ethyl acetate. The resulting organic layer was dried over anhydrous magnesium sulfate, and then filtered, followed by concentration. The resulting residue was purified by silica gel chromatography (developing solvent: hexane/ethyl acetate), thereby obtaining the title compound (8.72 g).

Step 3: Synthesis of (S)-tert-butyl 4-(2-hydroxyethyl)-2,2-dimethyloxazolidine-3-carboxylate

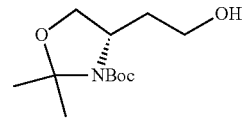

A 1 M diisobutylaluminium hydride-toluene solution (65.7 ml) was added to a solution of the (S)-tert-butyl 4-(2-methoxy-2-oxoethyl)-2,2-dimethyloxazolidine-3-carboxylate (8.71 g) obtained in Step 2 in methylene chloride (87.1 ml) under ice cooling, and the mixture was stirred for 2 hours under ice cooling. A 5% potassium sodium tartrate aqueous solution and ethyl acetate were added to the reaction mixture, and the mixture was stirred overnight at room temperature. The resulting organic layer was dried over anhydrous magnesium sulfate, and then filtered, followed by concentration. The resulting residue was purified by silica gel chromatography (developing solvent: hexane/ethyl acetate), thereby obtaining the title compound (5.94 g).

Step 4: Synthesis of (S)-tert-butyl 2,2-dimethyl-4-(2-oxoethyl)oxazolidine-3-carboxylate

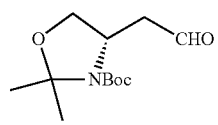

Triethylamine (16.9 ml) and a sulfur trioxide pyridine complex (12.56 g) were added to a solution of the (S)-tert-butyl 4-(2-hydroxyethyl)-2,2-dimethyloxazolidine-3-carboxylate (5.94 g) obtained in Step 3 in DMSO (59.4 ml) at room temperature, and the mixture was stirred for 1 hour at the same temperature. The reaction mixture was poured into a saturated aqueous sodium bicarbonate solution, and extracted with ethyl acetate. The resulting organic layer was dried over anhydrous magnesium sulfate, and then filtered, followed by concentration. The resulting residue was purified by silica gel chromatography (developing solvent: hexane/ethyl acetate), thereby obtaining the title compound (6.06 g).

Step 5: Synthesis of (S)-tert-butyl 4-(but-2-en-1-yl)-2,2-dimethyloxazolidine-3-carboxylate

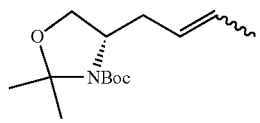

A 2.69 M n-butyllithium-hexane solution (7.0 ml) was added to a suspension of ethyltriphenylphosphonium bromide (5.60 g) in THF (25.2 ml) under ice-cooling, and the mixture was stirred for 30 minutes under ice-cooling. A solution of the (S)-tert-butyl 2,2-dimethyl-4-(2-oxoethyl)oxazolidine-3-carboxylate (3.06 g) obtained in Step 4 in THF (3.06 ml) was added to the reaction mixture under ice-cooling, and the mixture was stirred for 14 hours at room temperature. Hexane was added to the reaction mixture, and the insoluble matter was filtered off, followed by washing with THF-hexane=2/1. The filtrate was concentrated under reduced pressure. The resulting residue was purified by silica gel chromatography (developing solvent: hexane/ethyl acetate), thereby obtaining the title compound (1.81 g).

Step 6: Synthesis of (S)-tert-butyl (1-hydroxyhex-4-en-2-yl)carbamate

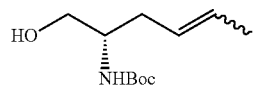

A 4 N hydrogen chloride-dioxane solution (18.1 ml) was added to the (S)-tert-butyl 4-(but-2-en-1-yl)-2,2-dimethyloxazolidine-3-carboxylate (1.81 g) obtained in Step 5 at room temperature, and the mixture was stirred for 2 hours at 70° C. The reaction mixture was cooled, and then concentrated under reduced pressure. The resulting residue was dissolved in THF (18.1 ml), and a saturated aqueous sodium bicarbonate solution (18.1 ml) and di-tert-butyl dicarbonate (1.53 g) were added thereto at room temperature. The mixture was stirred overnight at the same temperature. The reaction mixture was poured into water, and extracted with ethyl acetate. The resulting organic layer was dried over anhydrous magnesium sulfate, and then filtered, followed by concentration. The resulting residue was purified by silica gel chromatography (developing solvent: hexane/ethyl acetate), thereby obtaining the title compound (1.57 g).

Step 7: Synthesis of Compound 19

The same synthesis as in Steps 4 to 10 of Example 13 was performed using the (S)-tert-butyl (1-hydroxyhex-4-en-2-yl)carbamate obtained in Step 6 instead of the (R)-tert-butyl (5-hydroxypent-1-en-3-yl)carbamate used in Step 4 of Example 13, thereby obtaining the title compound (327 mg).

$^1$H-NMR (DMSO-d$_6$) δ: 1.47 (3H, d, J=7.1 Hz), 2.64-2.70 (1H, m), 2.81-2.85 (1H, m), 4.00-4.09 (1H, m), 4.32-4.43 (2H, m), 5.41-5.46 (1H, m), 5.60-5.63 (1H, m), 5.82 (2H, brs), 6.11-6.16 (1H, m), 6.21-6.31 (1H, m), 8.05 (1H, d, J=7.3 Hz), 8.08 (1H, d, J=8.5 Hz), 8.13 (1H, s), 8.35-8.39 (2H, m), 8.87-8.92 (1H, m).

ESI-MS m/z 411[M+H]$^+$.

Example 20

Mixture of (S)—N-(4-amino-6-isopropyl-5-(quinolin-3-yl)-8,9-dihydropyrimido[5,4-b]indolizin-8-yl)acrylamide (Compound 20A) and (S)—N-(4-amino-6-(propan-2-ylidene)-5-(quinolin-3-yl)-6,7,8,9-tetrahydropyrimido[5,4-b]indolizin-8-yl)acrylamide (Compound 20B)

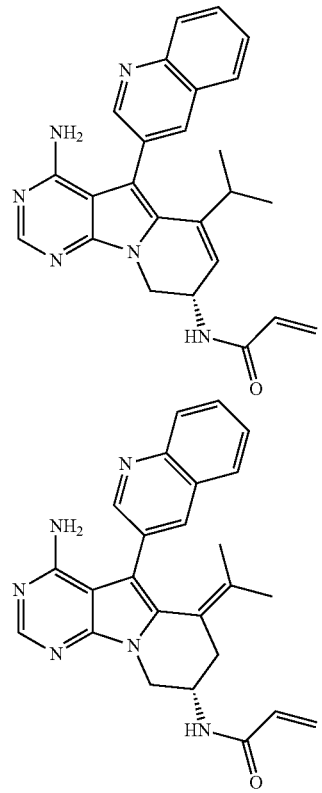

The same synthesis as in Example 19 was performed using isopropyltriphenylphosphonium iodide instead of the ethyltriphenylphosphonium bromide used in Step 5 of Example 19, thereby obtaining a mixture (18.9 mg) of the title compound.

$^1$H-NMR (DMSO-d$_6$) δ: 0.85-4.71 (11H, m), 5.63-5.68 (1H, m), 5.88 (1H, brs), 6.03 (1H, brs), 6.12-6.19 (1H, m), 6.24-6.31 (1H, m), 7.59-7.64 (1H, m), 7.72-7.78 (1H, m), 7.96-7.99 (1H, m), 8.01-8.05 (1H, m), 8.16 (1H, d, J=3.4 Hz), 8.24-8.28 (1H, m), 8.39-8.44 (1H, m), 8.90 (1H, d, J=2.0 Hz).
ESI-MS m/z 425[M+H]$^+$.

Example 21

(R)—N-(4-amino-6-methylene-5-(quinolin-3-yl)-7,8-dihydro-6H-pyrimido[5,4-b]pyrrolizin-7-yl)-N-methylacrylamide (Compound 21)

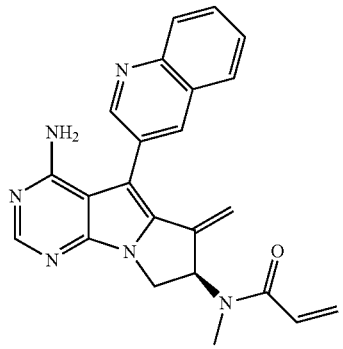 [SMILES: C=CC(=O)N(C)[C@H]1Cn2c(c(-c3cnc4ccccc4c3)c3c(N)ncnc32)C1=C]

Step 1: Synthesis of (R)-tert-butyl (1-(4-chloro-5-iodo-7H-pyrrolo[2,3-d]pyrimidin-7-yl)but-3-en-2-yl) carbamate

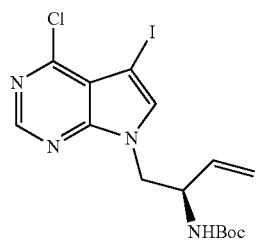 [SMILES: C=C[C@H](Cn1cc(I)c2c(Cl)ncnc21)NC(=O)OC(C)(C)C]

The same synthesis as in Step 1 of Example 1 was performed using (R)-tert-butyl (1-hydroxybut-3-en-2-yl) carbamate instead of the (S)-tert-butyl (1-hydroxybut-3-en-2-yl)carbamate used in Step 1 of Example 1, thereby obtaining the title compound (1.083 g) as a light-yellow solid.
ESI-MS m/z 448, 450 [M+H]$^+$.

Step 2: Synthesis of (R)-tert-butyl (1-(4-chloro-5-iodo-7H-pyrrolo[2,3-d]pyrimidin-7-yl)but-3-en-2-yl)(methyl)carbamate

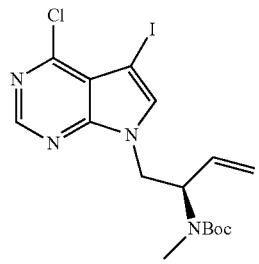 [SMILES: C=C[C@H](Cn1cc(I)c2c(Cl)ncnc21)N(C)C(=O)OC(C)(C)C]

Methyl iodide (1.58 ml), and sodium hydride (224 mg) dispersed in liquid paraffin were added to a solution of the (R)-tert-butyl (1-(4-chloro-5-iodo-7H-pyrrolo[2,3-d]pyrimidin-7-yl)but-3-en-2-yl)carbamate (2.28 g) obtained in Step 1 in DMF (11.4 ml) at room temperature, and the mixture was stirred for 1 hour at the same temperature. The resulting mixture was poured into water, and extracted with ethyl acetate. The resulting organic layer was washed with water and a saturated sodium chloride solution, and was dried over anhydrous sodium sulfate; thereafter, the solvent was distilled off under reduced pressure. The resulting residue was purified by silica gel column chromatography (developing solvent: hexane/ethyl acetate), thereby obtaining the title compound (2.41 g) as a light-yellow solid.
ESI-MS m/z 462, 464 [M+H]$^+$.

Step 3: Synthesis of Compound 21

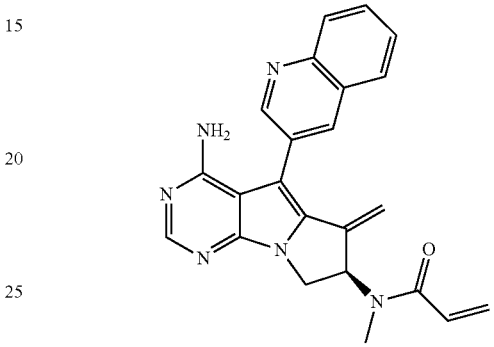

The same synthesis as in Steps 5 to 10 of Example 13 was performed using the (R)-tert-butyl (1-(4-chloro-5-iodo-7H-pyrrolo[2,3-d]pyrimidin-7-yl)but-3-en-2-yl)(methyl)carbamate obtained in Step 2 instead of the (R)-tert-butyl (5-(4-chloro-5-iodo-7H-pyrrolo[2,3-d]pyrimidin-7-yl) pent-1-en-3-yl) carbamate used in Step 5 of Example 13, thereby obtaining the title compound (256 mg) as a light-yellow solid.
$^1$H-NMR (DMSO-d$_6$) δ: 2.75 and 2.94 (total 3H, each s), 4.06-4.20 (1H, m), 4.46-4.72 (1H, m), 4.81-4.89 (1H, m), 5.26-5.35 (1H, m), 5.70-5.80 (1H, m), 5.98-6.37 (4H, m), 6.77-7.01 (1H, m), 7.62-7.68 (1H, m), 7.77-7.83 (1H, m), 8.03-8.10 (2H, m), 8.14-8.18 (1H, m), 8.41-8.45 (1H, m), 8.96-9.01 (1H, m).
ESI-MS m/z 397[M+H]$^+$.

Example 22

(R)—N-(4-amino-6-methylene-5-(quinolin-3-yl)-6,7,8,9-tetrahydropyrimido[5,4-b]indolizin-8-yl)-N-methylacrylamide (Compound 22)

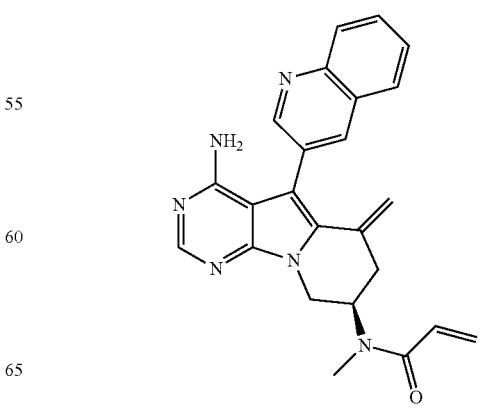

Step 1: Synthesis of (R)-tert-butyl (1-(4-chloro-5-iodo-7H-pyrrolo[2,3-d]pyrimidin-7-yl)pent-4-en-2-yl)(methyl)carbamate

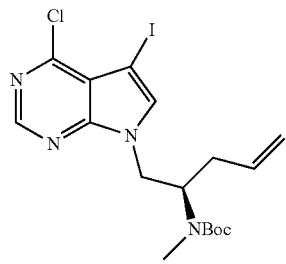 [SMILES: C=CC[C@H](Cn1cc(I)c2c(Cl)ncnc21)N(C)C(=O)OC(C)(C)C]

The same synthesis as in Step 2 of Example 21 was performed using the (R)-tert-butyl (1-(4-chloro-5-iodo-7H-pyrrolo[2,3-d]pyrimidin-7-yl)pent-4-en-2-yl)carbamate obtained in Steps 16 and 17 instead of the (R)-tert-butyl (1-(4-chloro-5-iodo-7H-pyrrolo[2,3-d]pyrimidin-7-yl)but-3-en-2-yl)carbamate used in Step 2 of Example 21, thereby obtaining the title compound (2.743 g) as a light-yellow solid.
ESI-MS m/z 477, 479 [M+H]$^+$.

Step 2: Synthesis of (R)-tert-butyl (4-amino-6-methylene-5-(quinolin-3-yl)-6,7,8,9-tetrahydropyrimido[5,4-b]indolizin-8-yl)(methyl)carbamate

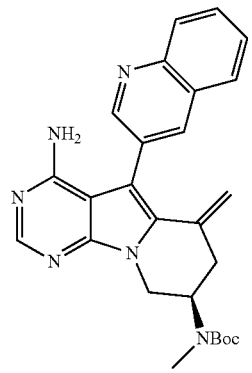 [SMILES: C=C1C[C@@H](N(C)C(=O)OC(C)(C)C)Cn2c1c(-c1cnc3ccccc3c1)c1c(N)ncnc12]

The same synthesis as in Steps 5 to 8 of Example 13 was performed using the (R)-tert-butyl (1-(4-chloro-5-iodo-7H-pyrrolo[2,3-d]pyrimidin-7-yl)pent-4-en-2-yl)(methyl)carbamate obtained in Step 1 instead of the (R)-tert-butyl (5-(4-chloro-5-iodo-7H-pyrrolo[2,3-d]pyrimidin-7-yl)pent-1-en-3-yl)carbamate used in Step 5 of Example 13, thereby obtaining the title compound (1.366 g) as a light-brown solid.
ESI-MS m/z 457 [M+H]$^+$.

Step 3: Synthesis of (R)—N$^8$-methyl-6-methylene-5-(quinolin-3-yl)-6,7,8,9-tetrahydropyrimido[5,4-b]indolizin-4,8-diamine

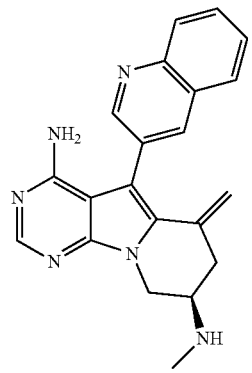 [SMILES: C=C1C[C@@H](NC)Cn2c1c(-c1cnc3ccccc3c1)c1c(N)ncnc12]

5 N hydrochloric acid (0.5 ml) was added to a solution of the (R)-tert-butyl (4-amino-6-methylene-5-(quinolin-3-yl)-6,7,8,9-tetrahydropyrimido[5,4-b]indolizin-8-yl)(methyl)carbamate (228 mg) obtained in Step 2 in ethanol (3 ml), and the mixture was stirred for 4 days at 50° C. After cooling, the reaction mixture was basified with a 5 N aqueous sodium hydroxide solution, followed by extraction with chloroform. After the resulting organic layer was dried over anhydrous sodium sulfate, the solvent was distilled off under reduced pressure. The resulting residue was purified by basic silica gel column chromatography (developing solvent: chloroform/methanol), thereby obtaining the title compound (197 mg) as a light-brown solid.
ESI-MS m/z 357 [M+H]$^+$.

Step 4: Synthesis of Compound 22

The same synthesis as in Step 10 of Example 13 was performed using the (R)—N$^8$-methyl-6-methylene-5-(quinolin-3-yl)-6,7,8,9-tetrahydropyrimido[5,4-b]indolizin-4,8-diamine obtained in Step 3 instead of the ((R)-6-methylene-5-(quinolin-3-yl)-6,7,8,9-tetrahydropyrimido[5,4-b]indolizin-4,7-diamine used in Step 10 of Example 13, thereby obtaining the title compound (68.5 mg) as a light-yellow solid.
$^1$H-NMR (DMSO-d$_6$) δ: 2.53-2.68 (1H, m), 2.88-3.11 (4H, m), 4.04-4.20 (1H, m), 4.34-4.96 (4H, m), 5.58-6.21 (4H, m), 6.72-7.01 (1H, m), 7.62-7.68 (1H, m), 7.78-7.83 (1H, m), 8.02-8.10 (2H, m), 8.15 (1H, brs), 8.37-8.44 (1H, m), 8.86-8.90 (1H, m).
ESI-MS m/z 411[M+H]$^+$.

Example 23

(R)—N-(4-amino-6-methyl-5-(quinolin-3-yl)-8,9-dihydropyrimido[5,4-b]indolizin-8-yl)-N-methylacrylamide (Compound 23)

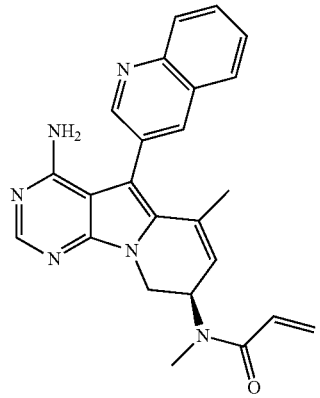 [SMILES: C=CC(=O)N(C)[C@@H]1C=C(C)c2c(-c3cnc4ccccc4c3)c3c(N)ncnc3n2C1]

Step 1: Synthesis of (R)—N' 6-dimethyl-5-(quinolin-3-yl)-8,9-dihydropyrimido[5,4-b]indolizin-4,8-diamine

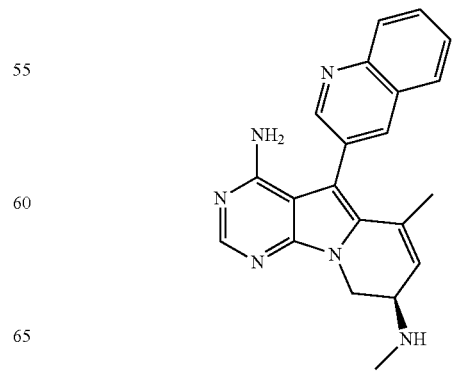

5 N hydrochloric acid (1 ml) was added to a solution of the (R)-tert-butyl (4-amino-6-methylene-5-(quinolin-3-yl)-6,7,8,9-tetrahydropyrimido[5,4-b]indolizin-8-yl)(methyl)carbamate (228 mg) obtained in Step 2 of Example 22 in ethanol (4 ml), and the mixture was stirred for 24 hours while being heated under reflux. After cooling, the reaction mixture was basified with a 5 N aqueous sodium hydroxide solution, followed by extraction with chloroform. After the resulting organic layer was dried over anhydrous sodium sulfate, the solvent was distilled off under reduced pressure. The resulting residue was purified by basic silica gel column chromatography (developing solvent: chloroform/methanol), thereby obtaining the title compound (190.8 mg) as a light-brown solid.

ESI-MS m/z 357 [M+H]$^+$.

Step 2: Synthesis of Compound 23

The same synthesis as in Step 10 of Example 13 was performed using the (R)—N$^8$,6-dimethyl-5-(quinolin-3-yl)-8,9-dihydropyrimido[5,4-b]indolizin-4,8-diamine obtained in Step 1 instead of the ((R)-6-methylene-5-(quinolin-3-yl)-6,7,8,9-tetrahydropyrimido[5,4-b]indolizin-4,7-diamine used in Step 10 of Example 13, thereby obtaining the title compound (150.9 mg) as a yellow solid.

$^1$H-NMR (DMSO-d$_6$) δ: 1.52 (3H, s), 2.74 and 2.88 (total 3H, each brs), 4.14-4.42 (2H, m), 5.21-5.98 (5H, m), 6.09-6.22 (1H, m), 6.71-7.03 (1H, m), 7.64-7.69 (1H, m), 7.79-7.85 (1H, m), 8.02-8.07 (1H, m), 8.08-8.12 (1H, m), 8.14 (1H, s), 8.43-8.49 (1H, m), 8.89-8.96 (1H, m).

ESI-MS m/z 411[M+H]$^+$.

Example 24

N-((7S)-4-amino-6-methyl-5-(quinolin-3-yl)-7,8-dihydro-6H-pyrimido[5,4-b]pyrrolizin-7-yl)acrylamide (Compound 24)

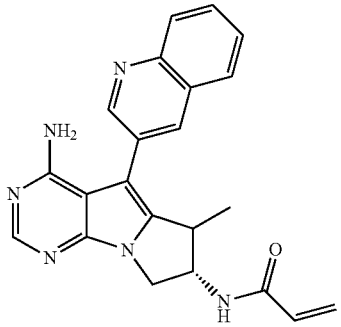 [SMILES: C=CC(=O)N[C@@H]1Cn2c(c(-c3cnc4ccccc4c3)c3c(N)ncnc32)C1C]

Step 1: Synthesis of tert-butyl ((7S)-4-amino-6-methyl-5-(quinolin-3-yl)-7,8-dihydro-6H-pyrimido[5,4-b]pyrrolizin-7-yl)carbamate

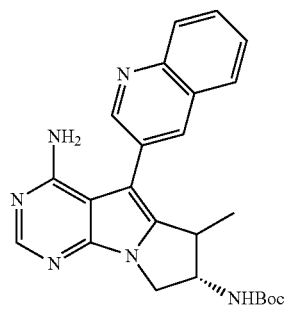 [SMILES: CC1c2c(-c3cnc4ccccc4c3)c3c(N)ncnc3n2C[C@H]1NC(=O)OC(C)(C)C]

10% palladium-carbon (50% wet, 15.0 mg) was added to a solution of the (S)-tert-butyl (4-amino-6-methylene-5-(quinolin-3-yl)-7,8-dihydro-6H-pyrimido[5,4-b]pyrrolizin-7-yl)carbamate (15.0 mg) obtained in Step 5 of Example 1 in ethyl acetate (2 ml)-ethanol (1 ml), and the mixture was stirred for 12 hours at room temperature under a hydrogen atmosphere. The reaction mixture was filtered through Celite, and the filtrate was concentrated under reduced pressure. The resulting residue was purified by preparative thin-layer chromatography (developing solvent: chloroform/methanol), thereby obtaining the title compound (10.0 mg).

ESI-MS m/z 357 [M+H]$^+$.

Step 2: Synthesis of Compound 24

The same synthesis as in Steps 9 and 10 of Example 13 was performed using the tert-butyl ((7S)-4-amino-6-methyl-5-(quinolin-3-yl)-7,8-dihydro-6H-pyrimido[5,4-b]pyrrolizin-7-yl)carbamate obtained in Step 1 instead of the (R)-tert-butyl (4-amino-6-methylene-5-(quinolin-3-yl)-6,7,8,9-tetrahydropyrimido[5,4-b]indolizin-7-yl)carbamate used in Step 9 of Example 13, thereby obtaining the title compound (3.10 mg) as a colorless solid.

$^1$H-NMR (DMSO-d$_6$) δ: 0.86 (2.7H, d, J=7.6 Hz), 1.08 (0.3H, d, J=7.6 Hz), 3.43-4.02 (2H, m), 4.34-4.62 (1H, m), 5.08-5.19 (1H, m), 5.59-5.68 (1H, m), 5.99-6.17 (3H, m), 6.18-6.33 (1H, m), 7.62 (1H, dd, J=7.6, 7.6 Hz), 7.75 (1H, dd, J=7.6, 7.6 Hz), 7.99-8.07 (2H, m), 8.12 (1H, s), 8.29-8.36 (1H, m), 8.53-8.76 (1H, m), 8.98 (1H, d, J=2.2 Hz).

ESI-MS m/z 385[M+H]$^+$.

Example 25

(R)—N-(4-amino-6-methylene-5-(quinolin-3-yl)-7,8-dihydro-6H-pyrimido[5,4-b]pyrrolizin-7-yl)acrylamide (Compound 25)

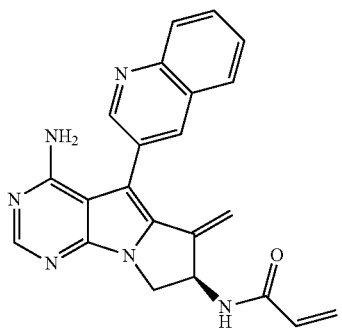 [SMILES: C=CC(=O)N[C@H]1Cn2c(c(-c3cnc4ccccc4c3)c3c(N)ncnc32)C1=C]

The same synthesis as in Steps 2 to 6 of Example 1 was performed using the (R)-tert-butyl (1-(4-chloro-5-iodo-7H-pyrrolo[2,3-d]pyrimidin-7-yl)but-3-en-2-yl)carbamate obtained in Step 1 of Example 21 instead of the (S)-tert-butyl (1-(4-chloro-5-iodo-7H-pyrrolo[2,3-d]pyrimidin-7-yl)but-3-en-2-yl)carbamate used in Step 2 of Example 1, thereby obtaining the title compound (44.6 mg) as a light-yellow solid.

$^1$H-NMR (DMSO-d$_6$) δ: 3.88-3.93 (1H, m), 4.57-4.63 (1H, m), 5.03 (1H, d, J=2.4 Hz), 5.24 (1H, d, J=2.4 Hz), 5.55-5.62 (1H, m), 5.68 (1H, dd, J=10.0, 2.4 Hz), 6.12-6.38 (4H, m), 7.65 (1H, dd, J=7.8, 7.8 Hz), 7.77-7.83 (1H, m), 8.04-8.11 (2H, m), 8.15 (1H, s), 8.41 (1H, d, J=2.2 Hz), 8.82 (1H, d, J=7.8 Hz), 8.98 (1H, d, J=2.2 Hz).

ESI-MS m/z 383[M+H]$^+$.

Example 26

(S)—N-(4-amino-6-methylene-5-(quinolin-3-yl)-7,8-dihydro-6H-pyrimido[5,4-b]pyrrolizin-7-yl)-N-methylacrylamide (Compound 26)

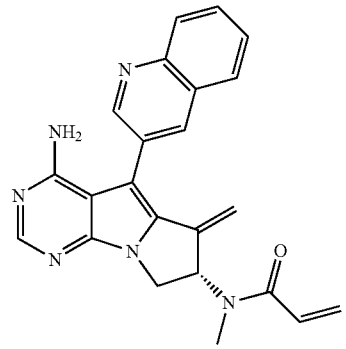 [SMILES: C=CC(=O)N(C)[C@@H]1Cn2c(c(-c3cnc4ccccc4c3)c3c(N)ncnc32)C1=C]

The same synthesis as in Steps 2 and 3 of Example 21 was performed using the (S)-tert-butyl (1-(4-chloro-5-iodo-7H-pyrrolo[2,3-d]pyrimidin-7-yl)but-3-en-2-yl)carbamate obtained in Step 1 of Example 1 instead of the (R)-tert-butyl (1-(4-chloro-5-iodo-7H-pyrrolo[2,3-d]pyrimidin-7-yl)but-3-en-2-yl)carbamate used in Step 2 of Example 21, thereby obtaining the title compound (143 mg) as a light-yellow solid.

$^1$H-NMR (DMSO-d$_6$) δ: 2.75 and 2.94 (total 3H, each s), 4.06-4.20 (1H, m), 4.46-4.72 (1H, m), 4.81-4.89 (1H, m), 5.26-5.35 (1H, m), 5.70-5.80 (1H, m), 5.98-6.37 (4H, m), 6.77-7.01 (1H, m), 7.62-7.68 (1H, m), 7.77-7.83 (1H, m), 8.03-8.10 (2H, m), 8.14-8.18 (1H, m), 8.41-8.45 (1H, m), 8.96-9.01 (1H, m).

ESI-MS m/z 397[M+H]$^+$.

Example 27

(S)—N-(4-amino-5-(quinolin-3-yl)-8,9-dihydropyrimido[5,4-b]indolizin-8-yl)acrylamide (Compound 27)

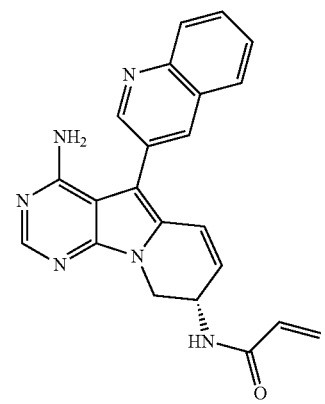 [SMILES: C=CC(=O)N[C@H]1C=Cc2c(-c3cnc4ccccc4c3)c3c(N)ncnc3n2C1]

Step 1: Synthesis of (S)-tert-butyl (4-amino-5-(quinolin-3-yl)-6,7,8,9-tetrahydropyrimido[5,4-b]indolizin-8-yl)carbamate

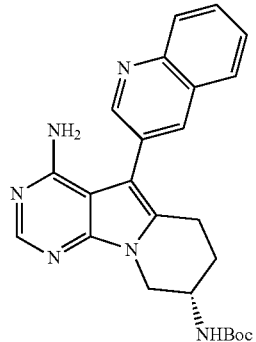 [SMILES: CC(C)(C)OC(=O)N[C@H]1CCc2c(-c3cnc4ccccc4c3)c3c(N)ncnc3n2C1]

A solution of 0.5 M 9-borabicyclo[3.3.1]nonane in tetrahydrofuran (141.3 ml) was added to a solution of the (S)-tert-butyl (1-(4-amino-6-bromo-5-(quinolin-3-yl)-7H-pyrrolo[2,3-d]pyrimidin-7-yl)but-3-en-2-yl)carbamate (6.0 g) obtained in Step 4 of Example 1 in tetrahydrofuran (42 ml) under a nitrogen atmosphere. The mixture was stirred at room temperature for 2 hours. A 2 N aqueous sodium hydroxide solution (84.8 ml) was gradually added to the reaction mixture at room temperature, and degassed under reduced pressure. Under a nitrogen atmosphere, (tetrakistriphenylphosphine)palladium(0) (1.70 g) was added, and the mixture was stirred at 66° C. for 12 hours. After the reaction mixture was cooled, the organic layer was separated and washed with a 20% aqueous ammonium chloride solution (60 ml). SH silica gel (6.0 g) was then added to the organic layer, and the mixture was stirred at 50° C. under a nitrogen atmosphere for 14 hours, and then filtered. SH silica gel (produced by Fuji Silysia Chemical Ltd.) (6.0 g) was added to the filtrate again, and the mixture was stirred under a nitrogen atmosphere at 50° C. for 14 hours, and then filtered. The solvent was distilled off from the filtrate under reduced pressure. The resulting residue was purified by silica gel column chromatography (developing solvent: ethyl acetate/methanol), thereby obtaining the title compound (4.46 g; yield=88%) as a light-yellow solid.

ESI-MS m/z 431 [M+H]$^+$.

Step 2: Synthesis of (8S)-4-amino-8-((tert-butoxycarbonyl)amino)-5-(quinolin-3-yl)-6,7,8,9-tetrahydropyrimido[5,4-b]indolizin-6-yl acetate

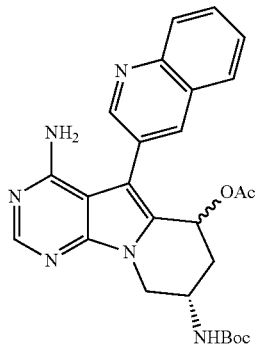 [SMILES: CC(=O)OC1C[C@H](NC(=O)OC(C)(C)C)Cn2c1c(-c1cnc3ccccc3c1)c1c(N)ncnc12]

Tetrabutylammonium iodide (37 mg) and iodobenzene diacetate (241 mg) were added to a solution of the (S)-tert-butyl (4-amino-5-(quinolin-3-yl)-6,7,8,9-tetrahydropyrimido[5,4-b]indolizin-8-yl)carbamate (215 mg) obtained in Step 1 in acetic acid (2 ml) and methylene chloride (2 ml)

under ice-cooling. The mixture was stirred for 2 hours under ice-cooling and for 2 hours at room temperature. After concentration under reduced pressure, the reaction mixture was basified with a saturated aqueous sodium bicarbonate solution, followed by extraction with ethyl acetate. The resulting organic layer was dried over anhydrous sodium sulfate, followed by filtration. Then the solvent was distilled off under reduced pressure. The resulting residue was purified by silica gel chromatography (developing solvent: ethyl acetate/methanol), thereby obtaining the title compound (216 mg) as a light-brown solid.

ESI-MS m/z 489 [M+H]$^+$.

Step 3: Synthesis of tert-butyl ((8S)-4-amino-6-hydroxy-5-(quinolin-3-yl)-6,7,8,9-tetrahydropyrimido[5,4-b]indolizin-8-yl)carbamate

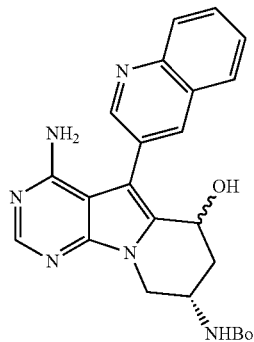

A 2 N aqueous sodium hydroxide solution (1 ml) was added to a solution of the (8S)-4-amino-8-((tert-butoxycarbonyl)amino)-5-(quinolin-3-yl)-6,7,8,9-tetrahydropyrimido[5,4-b]indolizin-6-yl acetate (215 mg) obtained in Step 2 in methanol (3 ml) at room temperature, and the mixture was stirred for 1 hour at room temperature. The reaction mixture was poured into water, and extracted with chloroform. The resulting organic layer was dried over anhydrous sodium sulfate, followed by filtration. Then, the solvent was distilled off under reduced pressure. The resulting residue was purified by silica gel chromatography (developing solvent: ethyl acetate/methanol), thereby obtaining the title compound (166.7 mg) as a light-yellow solid.

ESI-MS m/z 447 [M+H]$^+$.

Step 4: Synthesis of (S)-5-(quinolin-3-yl)-8,9-dihydropyrimido[5,4-b]indolizin-4,8-diamine

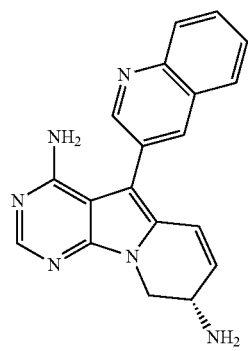 [SMILES: Nc1ncnc2c1c(-c1cnc3ccccc3c1)c1n2C[C@@H](N)C=C1]

A mixture of the tert-butyl ((8S)-4-amino-6-hydroxy-5-(quinolin-3-yl)-6,7,8,9-tetrahydropyrimido[5,4-b]indolizin-8-yl)carbamate (44.6 mg) obtained in Step 3, p-toluenesulfonic acid monohydrate (95 mg), and toluene (3 ml) was stirred for 4 hours at 100° C. After cooling the reaction mixture, the solvent was distilled off under reduced pressure. The resulting residue was purified by silica gel chromatography (developing solvent: chloroform/methanol), thereby obtaining the title compound (39 mg) as a light-brown, oily substance.

ESI-MS m/z 329 [M+H]$^+$.

Step 5: Synthesis of Compound 27

The same synthesis as in Step 10 of Example 13 was performed using the (S)-5-(quinolin-3-yl)-8,9-dihydropyrimido[5,4-b]indolizin-4,8-diamine obtained in Step 4 instead of the (R)-6-methylene-5-(quinolin-3-yl)-6,7,8,9-tetrahydropyrimido[5,4-b]indolizin-4,7-diamine used in Step 10 of Example 13, thereby obtaining the title compound (44.1 mg) as a yellow solid.

$^1$H-NMR (DMSO-d$_6$) δ: 4.19-4.30 (2H, m), 4.86-4.94 (1H, m), 5.63 (1H, dd, J=9.8, 2.7 Hz), 6.08-6.32 (5H, m), 6.70 (1H, dd, J=9.8, 1.1 Hz), 7.62-7.69 (1H, m), 7.75-7.82 (1H, m), 8.04-8.09 (2H, m), 8.17 (1H, s), 8.34 (1H, d, J=2.0 Hz), 8.55 (1H, d, J=7.3 Hz), 8.91 (1H, d, J=2.4 Hz).

ESI-MS m/z 383[M+H]$^+$.

Example 28

(R)—N-(4-amino-5-(quinolin-3-yl)-9,10-dihydro-8H-pyrimido[5',4':4,5]pyrrolo[1,2-a]azepin-8-yl)acrylamide (Compound 28)

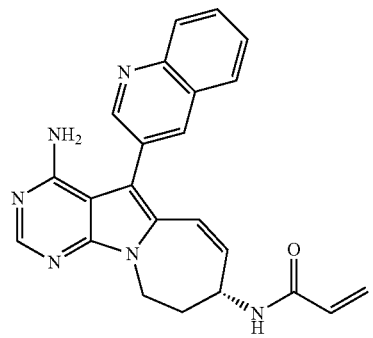 [SMILES: C=CC(=O)N[C@H]1C=Cc2c(-c3cnc4ccccc4c3)c3c(N)ncnc3n2CC1]

The same synthesis as in Example 27 was performed using the (R)-tert-butyl (5-(4-amino-6-bromo-5-(quinolin-3-yl)-7H-pyrrolo[2,3-d]pyrimidin-7-yl)pent-1-en-3-yl)carbamate obtained in Step 7 of Example 13 instead of the (S)-tert-butyl (1-(4-amino-6-bromo-5-(quinolin-3-yl)-7H-pyrrolo[2,3-d]pyrimidin-7-yl)but-3-en-2-yl)carbamate used in Step 1 of Example 27, thereby obtaining the title compound (101.8 mg) as a yellow solid.

$^1$H-NMR (DMSO-d$_6$) δ: 2.01-2.12 (1H, m), 2.23-2.33 (1H, m), 4.28-4.38 (1H, m), 4.55-4.63 (1H, m), 4.84-4.92 (1H, m), 5.62 (1H, dd, J=10.0, 2.4 Hz), 5.68 (1H, dd, J=12.6, 3.8 Hz), 6.08-6.31 (5H, m), 7.63-7.69 (1H, m), 7.78-7.83 (1H, m), 8.03-8.10 (2H, m), 8.18 (1H, s), 8.31 (1H, d, J=2.0 Hz), 8.51 (1H, d, J=8.2 Hz), 8.84 (1H, d, J=2.2 Hz).

ESI-MS m/z 397[M+H]$^+$.

Example 29

N-((6R*,8S)-4-amino-6-methyl-5-(quinolin-3-yl)-6,7,8,9-tetrahydropyrimido[5,4-b]indolizin-8-yl) acrylamide (Compound 29A) and N-((6S*,8S)-4-amino-6-methyl-5-(quinolin-3-yl)-6,7,8,9-tetrahydropyrimido[5,4-b]indolizin-8-yl)acrylamide (Compound 29B)

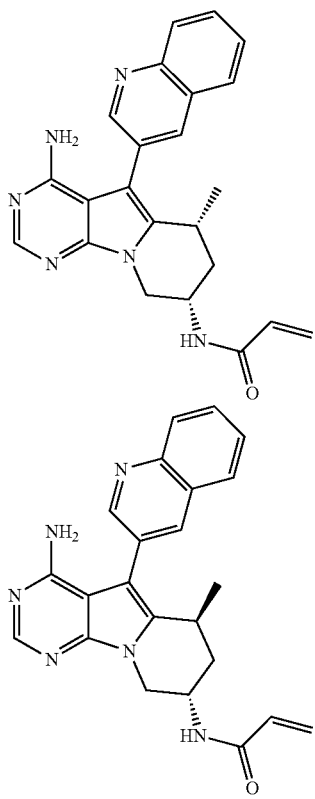

Step 1: Synthesis of (S)-tert-butyl (4-amino-6-methylene-5-(quinolin-3-yl)-6, 7,8,9-tetrahydropyrimido[5,4-b]indolizin-8-yl)carbamate

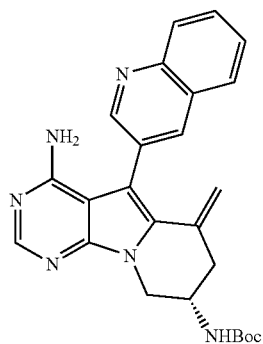 [SMILES: C=C1C[C@H](NC(=O)OC(C)(C)C)Cn2c1c(-c1cnc3ccccc3c1)c1c(N)ncnc12]

A mixture of the (S)-tert-butyl (4-amino-6-methyl-5-(quinolin-3-yl)-8,9-dihydropyrimido[5,4-b]indolizin-8-yl)carbamate and (S)-tert-butyl (4-amino-6-methylene-5-(quinolin-3-yl)-6,7,8,9-tetrahydropyrimido[5,4-b]indolizin-8-yl)carbamate obtained by the same synthesis as in Step 5 of Example 14 using the (S)-tert-butyl (1-(4-amino-6-bromo-5-(quinolin-3-yl)-7H-pyrrolo[2,3-d]pyrimidin-7-yl)pent-4-en-2-yl)carbamate (1.263 g) obtained in Step 4 of Example 14 was purified by silica gel chromatography (developing solvent: ethyl acetate/methanol), thereby obtaining the title compound (0.805 g) as a light-yellow solid.
ESI-MS m/z 443 [M+H]+.

Step 2: Synthesis of tert-butyl ((8S)-4-amino-6-methyl-5-(quinolin-3-yl)-6,7,8,9-tetrahydropyrimido[5,4-b]indolizin-8-yl)carbamate

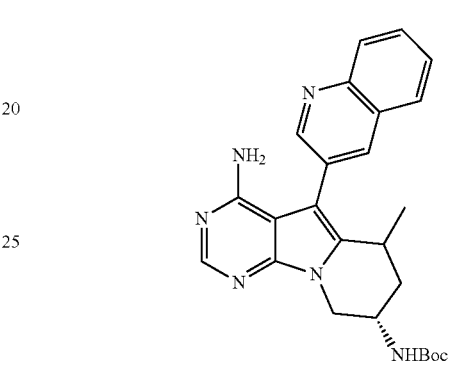

10% palladium-carbon (50% wet, 100.6 mg) was added to a solution of the (S)-tert-butyl (4-amino-6-methylene-5-(quinolin-3-yl)-6,7,8,9-tetrahydropyrimido[5,4-b]indolizin-8-yl)carbamate (100.0 mg) obtained in Step 1 in methanol (10 ml), and the mixture was stirred for 12 hours at room temperature under a hydrogen atmosphere. The reaction mixture was filtered through a glass fiber filter, and the filtrate was concentrated under reduced pressure. The resulting residue was purified by basic silica gel column chromatography (developing solvent: chloroform/methanol), thereby obtaining the title compound (122.1 mg).
ESI-MS m/z 445 [M+H]+.

Step 3: Synthesis of (8S)-6-methyl-5-(quinolin-3-yl)-6, 7,8,9-tetrahydropyrimido[5,4-b]indolizin-4,8-diamine

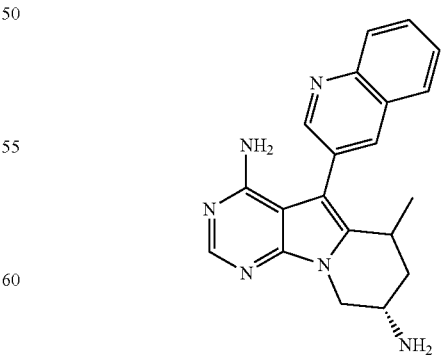

Trifluoroacetic acid (1 ml) was added to a solution of the tert-butyl ((8S)-4-amino-6-methyl-5-(quinolin-3-yl)-6,7,8,9-tetrahydropyrimido[5,4-b]indolizin-8-yl)carbamate (122.1 mg) obtained in Step 2 in chloroform (3 ml), and the mixture was stirred for 30 minutes at room temperature. The reaction mixture was concentrated under reduced pressure, and the resulting residue was dissolved in methanol. After desalting with a basic solid-phase extraction column (VARIAN BondElut), the mixture was concentrated under reduced pressure, thereby obtaining the title compound (58.9 mg) as a light-yellow solid.

ESI-MS m/z 345 [M+H]$^+$.

Step 4: Synthesis of N-((8S)-4-amino-6-methyl-5-(quinolin-3-yl)-6,7,8,9-tetrahydropyrimido[5,4-b]indolizin-8-yl)acrylamide

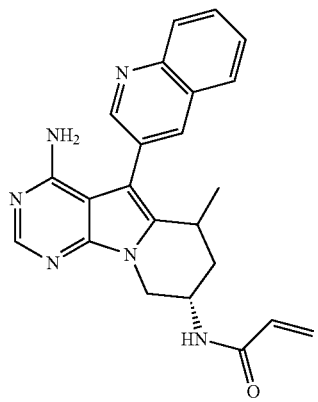 [SMILES: C=CC(=O)N[C@H]1CC(C)c2c(-c3cnc4ccccc4c3)c3c(N)ncnc3n2C1]

The same synthesis as in Step 7 of Example 14 was performed using the (8S)-6-methyl-5-(quinolin-3-yl)-6,7,8,9-tetrahydropyrimido[5,4-b]indolizin-4,8-diamine (58.9 mg) obtained in Step 3, thereby obtaining the title compound (30.3 mg) as a light-yellow solid.

ESI-MS m/z 399 [M+H]$^+$.

Step 5: Syntheses of Compound 29A and Compound 29B

A diastereomer mixture containing the (6R*,8S) isomer and (6S*,8S) isomer obtained in Step 4 was separated by a preparative chiral column chromatography (column: CHIRALCEL OZ-H (20 mm×250 mm×5 μm), manufactured by Daicel Chemical Industries, Ltd., developing solvent: hexane/ethanol/triethylamine=60/40/0.01), thereby obtaining Compound 29A and Compound 29B as a first fraction (15.8 mg) and a second fraction (6.1 mg), respectively, as colorless solids.

Compound 29A $^1$H-NMR (CDCl$_3$) δ: 0.96 (3H, d, J=6.6 Hz), 1.68 (1H, m), 2.29-2.39 (1H, m), 3.49-3.63 (1H, m), 3.81 (1H, dd, J=11.7, 10.2 Hz), 4.56-4.69 (1H, m), 4.76 (1H, dd, J=12.2, 5.1 Hz), 4.81 (2H, brs), 5.70 (1H, dd, J=10.5, 1.2 Hz), 6.17 (1H, dd, J=16.6, 10.2 Hz), 6.15-6.25 (1H, m), 6.36 (1H, dd, J=17.1, 1.2 Hz), 7.64 (1H, t, J=7.6 Hz), 7.75-7.82 (1H, m), 7.88 (1H, d, J=8.0 Hz), 8.18 (1H, d, J=8.5 Hz), 8.21-8.29 (2H, m), 9.05 (1H, d, J=2.0 Hz).

ESI-MS m/z 399[M+H]$^+$.

Compound 29B $^1$H-NMR (CDCl$_3$) δ: 1.06 (3H, d, J=6.8 Hz), 1.83-2.08 (1H, m), 2.18-2.31 (1H, m), 3.46-3.59 (1H, m), 4.00 (1H, dd, J=12.4, 7.6 Hz), 4.59 (1H, dd, J=12.4, 4.6 Hz), 4.73-4.93 (3H, m), 5.70 (1H, d, J=10.5 Hz), 6.18 (1H, dd, J=16.8, 10.2 Hz), 6.26-6.42 (2H, m), 7.63 (1H, t, J=7.6 Hz), 7.78 (1H, t, J=8.3 Hz), 7.88 (1H, d, J=8.0 Hz), 8.17 (1H, d, J=8.0 Hz), 8.20-8.27 (2H, m), 9.02 (1H, d, J=1.7 Hz).

ESI-MS m/z 399[M+H]$^+$.

Comparative Example 1

N-(3-(4-amino-6,7,8,9-tetrahydropyrimido[5,4-b]indolizin-5-yl)phenyl)benzamide (Comparative Compound 1)

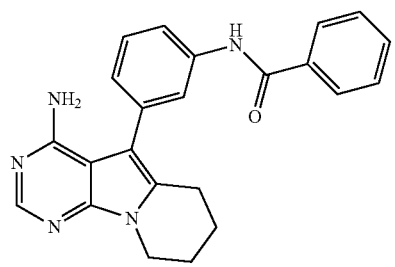 [SMILES: Nc1ncnc2c1c(-c1cccc(NC(=O)c3ccccc3)c1)c1n2CCCC1]

The compound was synthesized according to the method disclosed in the International Publication No. WO2006/102079 pamphlet.

ESI-MS m/z 384 [M+H]$^+$.

Test Examples

The compounds of the present invention were evaluated using the test methods below.

Test Example 1

Measurement of Inhibitory Action Against Various EGFR Kinase Activities (In Vitro)

1) Measurement of EGFR (T790M/L858R) Kinase Inhibitory Activity

The inhibitory activities of the compounds of the present invention against EGFR (T790M/L858R) kinase activity were measured.

Among the materials of the inhibitory activity measurement, the substrate peptide and the kinase protein were obtained as follows. A peptide with biotinylated N-terminus (biotin-EEPLYWSFPAKKK) was synthesized with reference to FL-Peptide 22, a reagent for LabChip® series of PerkinElmer, Inc. For the kinase protein, a purified recombinant human EGFR (T790M/L858R) protein of Carna Biosciences, Inc. was purchased.

The inhibitory activity measurement was performed as follows. The compounds of the present invention were individually dissolved in dimethyl sulfoxide (DMSO), and serial dilutions of these compounds were prepared using DMSO. Subsequently, a solution containing the substrate peptide (final concentration: 250 nM), magnesium chloride (final concentration: 10 mM), manganese chloride (final concentration: 10 mM), and ATP (final concentration: 1 μM) in a buffer solution for kinase reaction (Carna Biosciences, Inc.) was mixed with the dilutions of the compounds (final concentration of DMSO upon kinase reaction: 2.5%) or DMSO (final concentration: 2.5%). EGFR (T790M/L858R) protein was further added thereto, and the mixtures were incubated at 25° C. for 120 minutes to carry out a kinase reaction. EDTA was added thereto to a final concentration of 24 mM to thereby terminate the reaction. A phosphorylated thyrosine detection solution containing europium (Eu)-labeled anti-phosphorylated tyrosine antibody PT66 (PerkinElmer, Inc.) and SureLight APC-SA (PerkinElmer, Inc.) was added to the reaction mixtures, and the mixtures were allowed to stand at room temperature for 2 hours or more. For the background, a sample to which EDTA was added before addition of EGFR (T790M/L858R) protein was incubated at 25° C. for 120 minutes, using DMSO instead of the DMSO solution of the compound. The detection solution was also added to this sample, and the mixture was allowed to stand for 2 hours or more. Finally, for all of the test samples, the amount of fluorescence at the time of irradiation of excitation light having a wavelength of 337 nm was measured at dual wavelengths of 620 nm and 665 nm by PHERAstar FS (BMG LABTECH), and a ratio of the fluorescence amounts at the two wavelengths was obtained as data.

In the analysis of measured data, a ratio of the fluorescence amounts of the sample in which the kinase reaction was carried out with the addition of DMSO at a final concentration of 2.5% was set as a phosphorylation inhibition rate of 0%, and a ratio of the fluorescence amounts of the background was set as a phosphorylation inhibition rate of 100%. Based on the above rates, phosphorylation inhibition rates (%) were calculated for the samples to which various concentrations of the compound solutions were added. Finally, the obtained reaction inhibition rates (%) at the respective concentrations were plotted for each compound, and the $IC_{50}$ value (nM), which is a compound concentration at which phosphorylation by EGFR (T790M/L858R) is inhibited by 50%, was determined using XLfit curve-fitting software (IDBS).

2) Measurement of EGFR (d746-750/T790M) Kinase Inhibitory Activity

The inhibitory activities of the compounds of the present invention against EGFR (d746-750/T790M) kinase activity were measured.

The materials, the measurement method, and the data analysis method were substantially the same as those shown in the above description regarding "Measurement of EGFR (T790M/L858R) Kinase Inhibitory Activity," except that a purified recombinant human EGFR (d746-750/T790M) protein purchased from Carna Biosciences, Inc. was used as the kinase protein, and the measurement was performed with an ATP final concentration of 1.5 μM. Finally, the $IC_{50}$ value (nM) of each compound with respect to EGFR (d746-750/T790M) was determined by data analysis.

3) Measurement of EGFR (L858R) Kinase Inhibitory Activity

The inhibitory activities of the compounds of the present invention against EGFR (L858R) kinase activity were measured.

The materials, the measurement method, and the data analysis method were substantially the same as those shown in the above description regarding "Measurement of EGFR (T790M/L858R) Kinase Inhibitory Activity," except that a purified recombinant human EGFR (L858R) protein purchased from Carna Biosciences, Inc. was used as the kinase protein, and the measurement was performed with ATP at a final concentration of 4 μM. Finally, the $IC_{50}$ value (nM) of each compound with respect to EGFR (L858R) was determined by data analysis.

4) Measurement of EGFR (d746-750) Kinase Inhibitory Activity

The inhibitory activities of the compounds of the present invention against EGFR (d746-750) kinase activity were measured.

The materials, the measurement method, and the data analysis method were substantially the same as those shown in the above description regarding "Measurement of EGFR (T790M/L858R) Kinase Inhibitory Activity," except that a purified recombinant human EGFR (d746-750) protein purchased from Carna Biosciences, Inc. was used as the kinase protein, the measurement was performed with ATP at a final concentration of 5 μM, and the incubation for the kinase reaction was performed for 90 minutes. Finally, the $IC_{50}$ value (nM) of each compound with respect to EGFR (d746-750) was determined by data analysis.

5) Measurement of EGFR (WT) Kinase Inhibitory Activity

The inhibitory activities of the compounds of the present invention against EGFR (WT) kinase activity were measured.

The materials, the measurement method, and the data analysis method were substantially the same as those shown in the above description regarding "Measurement of EGFR (T790M/L858R) Kinase Inhibitory Activity," except that a kinase protein prepared by expressing a cytoplasmic domain of human EGFR (WT) with its N-terminus fused to a FLAG tag in insect Sf9 cells using a baculovirus expression system and then purifying it with anti-FLAG antibody agarose (Sigma-Aldrich) was used as the kinase protein, the final concentration of the substrate peptide was 500 nM, and the final concentration of ATP was 4.7 μM. Finally, the $IC_{50}$ value (nM) of each compound with respect to EGFR (WT) was determined by data analysis.

Table 1 shows the results of the tests using the various EGFR.

It was confirmed that the compounds of the present invention had strong inhibitory activities not only for EGFR (L858R) and EGFR (d746-750), but also for EGFR (T790M/L858R) and EGFR (d746-750/T790M). It was also confirmed that their inhibitory activities for EGFR (WT) were lower than those for the above EGFR proteins.

In contrast, it was confirmed that the compound of Comparative Example 1, which was a compound having a structure similar to that of the compound of the present invention, had almost no inhibitory activity against these EGFR kinases.

TABLE 1

| Example | Type of EGFR | | | | |
|---|---|---|---|---|---|
| | EGFR (T790M/ L858R) | EGFR (d746- 750/ T790M) | EGFR (L858R) | EGFR (d746- 750) | EGFR (WT) |
| 1 | <0.50 | <0.15 | <0.50 | <0.15 | 0.70 |
| 2 | 77 | 30 | 230 | 78 | 1400 |
| 3 | 6.1 | 1.8 | 15 | 7.6 | 110 |
| 4 | 0.40 | <0.50 | 0.63 | 0.45 | 6.0 |
| 5 | <0.15 | <0.15 | <0.15 | <0.15 | 0.78 |
| 6 | 0.24 | <0.15 | 0.45 | 0.24 | 4.9 |
| 7 | 1.0 | 0.53 | 1.7 | 1.2 | 12 |
| 8 | <0.50 | <0.15 | <0.50 | <0.15 | 1.0 |
| 9 | 2.1 | 0.45 | 5.9 | 2.3 | 52 |
| 10 | 1.5 | 0.61 | 2.6 | 1.8 | 22 |
| 11 | 0.76 | 0.32 | 1.4 | 0.88 | 12 |
| 12 | 0.66 | 0.29 | 1.2 | 0.75 | 11 |
| 13 | 2.1 | 1.1 | 2.8 | 2.1 | 24 |
| 14 | 0.24 | <0.50 | 0.32 | 0.19 | 2.9 |
| 15 | 1.6 | 1.2 | 1.3 | 1.4 | 7.9 |
| 16 | 11 | 3.0 | 39 | 15 | 480 |
| 17 | 23 | 11 | 50 | 39 | 580 |
| 18 | 4.7 | 1.3 | 12 | 4.5 | 68 |
| 19 | 0.26 | 0.28 | 0.27 | 0.42 | 2.2 |
| 20 | 3.7 | 2.4 | 4.1 | 2.9 | 28 |
| 21 | 0.60 | 0.34 | 1.1 | 0.72 | 7.8 |
| 22 | 0.35 | 0.23 | 0.37 | 0.33 | 5.5 |
| 23 | 0.44 | 0.30 | 0.63 | 0.29 | 7.3 |

TABLE 1-continued

| | Type of EGFR | | | | |
|---|---|---|---|---|---|
| Example | EGFR (T790M/ L858R) | EGFR (d746- 750/ T790M) | EGFR (L858R) | EGFR (d746- 750) | EGFR (WT) |
| 24 | 0.83 | 0.31 | 1.1 | 0.85 | 8.6 |
| 25 | 36 | 11 | 100 | 59 | |
| 26 | 1.0 | 0.31 | 1.7 | 1.1 | |
| 27 | 0.34 | 0.25 | 0.35 | 0.38 | |
| 28 | 0.30 | <0.50 | 0.49 | 0.27 | |
| 29 | 14 | 8.4 | 19 | 21 | |
| Comparative Example 1 | >5000 | >5000 | >5000 | 1500 | >5000 |

Test Example 2

Test for Activity of Growth Inhibition Against Wild-Type and Mutated EGFR-Expressing Cell Lines (In Vitro)

(1) A human small cell lung cancer cell line NCI-H1975 expressing EGFR (T790M/L858R), (2) a human non-small cell lung cancer cell line HCC827 expressing EGFR (d746-750), and (3) a human epithelioid cancer cell line A431 expressing EGFR (WT) were each suspended in complete growth medium recommended by ATCC. The cell suspensions were seeded in each well of a 384-well flat microplate or a 96-well flat plate, and cultured in an incubator containing 5% carbon dioxide gas at 37° C. for one day. Each compound of the present invention was dissolved in DMSO, and serial dilutions of the test compound were prepared using DMSO (to a concentration 500 times the final concentration). The DMSO solution of the test compound or DMSO was diluted with complete growth medium, and the resulting solution was added to each well of the cell culture plate so that the final concentration of DMSO was 0.2%. Then, the cells were cultured in an incubator containing 5% carbon dioxide gas at 37° C. for three days. The number of cells was measured before the addition of the DMSO solution of the test compound, as well as after addition and culture by using a CellTiter-Glo Assay® (produced by Promega) according to a protocol recommended by Promega.

For each cell, the cell growth inhibition rates of the wells to which the test compounds at various concentrations were added were calculated by the following formula. Then, the obtained inhibition rates (%) at the respective concentrations were plotted for each test compound, and the $GI_{50}$ value (nM), which is a test compound concentration at which the cell growth can be inhibited by 50%, was determined using XLfit curve-fitting software (IDBS).
Cell Growth Inhibition Rate (%)=(C−T)/(C−C0)×100
T: Luminescence intensity of well cultured for three days after addition of the test compound solution
C: Luminescence intensity of well cultured for three days after addition of DMSO
C0: Luminescence intensity of well before addition of the test compound solution Table 2 shows the results.
It was confirmed that the compounds of the present invention showed strong growth inhibitory effects not only for EGFR (d746-750) expressing cells, but also for EGFR (T790M/L858R) expressing cells. It was also confirmed that their growth inhibitory effects for EGFR (WT) expressing cells were lower than those for the above EGFR proteins.

TABLE 2

| | Type of EGFR | | |
|---|---|---|---|
| | EGFR (T790M/L858R) | EGFR (d746-750) | EGFR (WT) |
| Example | Cell name | | |
| | NCI-H1975 | HCC827 | A431 |
| 1 | 9.0 | 1.9 | 370 |
| 2 | 4200 | 780 | >10000 |
| 3 | 560 | 16 | >10000 |
| 4 | 140 | 5.5 | 2400 |
| 5 | 51 | 8.1 | 2200 |
| 6 | 54 | 3.3 | 520 |
| 7 | 150 | 5.6 | 2600 |
| 8 | 800 | 66 | 1100 |
| 9 | 770 | 7.5 | 4200 |
| 10 | 310 | 8.1 | 4400 |
| 11 | 260 | 9.7 | 3900 |
| 12 | 240 | 7.9 | 3500 |
| 13 | 150 | 13 | 1200 |
| 14 | 22 | 2.5 | 1900 |
| 15 | 85 | 22 | 2000 |
| 16 | 600 | 27 | >10000 |
| 17 | 2900 | 160 | >10000 |
| 18 | 160 | 8.9 | 4000 |
| 19 | 49 | 5.6 | 990 |
| 20 | 310 | 23 | 3900 |
| 21 | 56 | 8.1 | 2600 |
| 22 | 56 | 5.7 | 1500 |
| 23 | 47 | 3.3 | 5100 |
| 24 | 110 | 4.9 | 3400 |
| 25 | 2500 | 260 | >10000 |
| 26 | 150 | 18.4 | 4700 |
| 27 | 110 | 15 | 1000 |
| 28 | 48 | 14 | 1200 |
| 29 | 1600 | 89 | >10000 |

The invention claimed is:
1. A compound represented by Formula (I) below or a salt thereof:

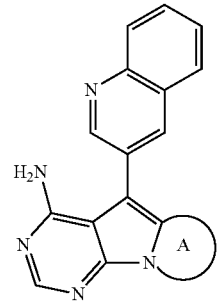

wherein the group:

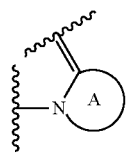

is (1) a group represented by Formula A1:

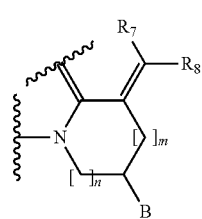

(in Formula A1, B is a group represented by:

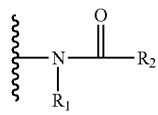

[$R_1$ is a hydrogen atom or a C1-C6 alkyl group; and $R_2$ is a group represented by:

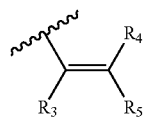

wherein $R_3$, $R_4$, and $R_5$ are the same or different, and each represents a hydrogen atom, a halogen atom, a C1-C6 alkyl group, a C6-C12 aryl group, a C4-C9 heteroaryl group, an aminomethyl group that may be substituted with a C1-C6 alkyl group, or a 1-piperidinomethyl group, or a group represented by:

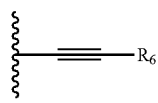

wherein $R_6$ represents a hydrogen atom or a C1-C6 alkyl group], $R_7$ and $R_8$ are the same or different, and each represents a hydrogen atom or a C1-C6 alkyl group; m is 0 or 1; and n is 1 or 2);

(2) a group represented by Formula A2:

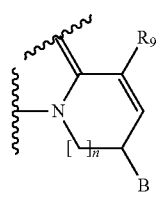

(in Formula A2, B and n are as defined in Formula A1; and $R_9$ is a hydrogen atom or a C1-C6 alkyl group); or (3) a group represented Formula A3:

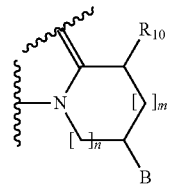

(in Formula A3, B, m, and n are as defined in Formula A1; and $R_{10}$ is a C2-C6 alkyl group).

2. The compound or a salt thereof according to claim 1, wherein $R_2$ is a group represented by:

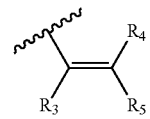

wherein $R_3$, $R_4$, and $R_5$ are the same or different, and each represents a hydrogen atom, a halogen atom, a C1-C6 alkyl group, an aminomethyl group that may be substituted with a C1-C6 alkyl group, or a 1-piperidinomethyl group, or a group represented by:

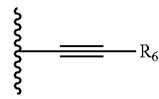

wherein $R_6$ represents a hydrogen atom or a C1-C6 alkyl group.

3. The compound or a salt thereof according to claim 1, wherein $R_2$ is a group represented by:

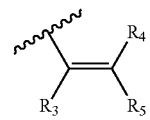

wherein $R_3$, $R_4$, and $R_5$ are the same or different, and each represents a hydrogen atom, a halogen atom, an aminomethyl group that may be substituted with a methyl group, or a 1-piperidinomethyl group.

4. The compound or a salt thereof according to claim 1, wherein the group:

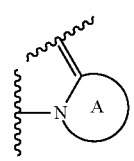

is (1) a group represented by Formula A1:

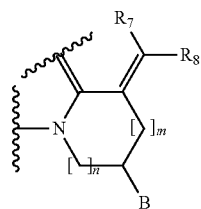

(in Formula A1, B is a group represented by:

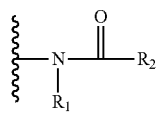

wherein R$_1$ is a hydrogen atom or a C1-C6 alkyl group; and R$_2$ is a group represented by:

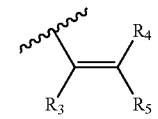

wherein R$_3$, R$_4$, and R$_5$ are the same or different, and each represents a hydrogen atom or a halogen atom,
R$_7$ and R$_8$ are the same or different, and each represents a hydrogen atom or a C1-C6 alkyl group; m is 0 or 1; and n is 1); or (2) a group represented by Formula A2:

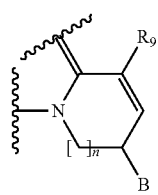

(in Formula A2, B and n are as defined in Formula A1; and R$_9$ is a hydrogen atom or a C1-C6 alkyl group).

5. The compound or a salt thereof according to claim 1, wherein the group:

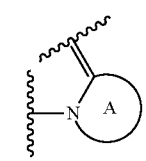

is (1) a group represented by Formula A1:

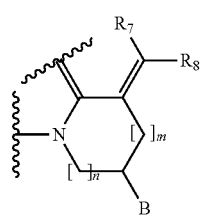

(in Formula A1, B is a group represented by:

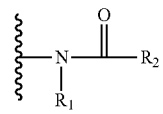

wherein R$_1$ is a hydrogen atom; and R$_2$ is a group represented by:

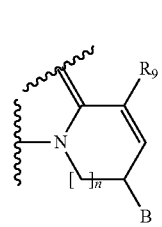

wherein R$_3$, R$_4$, and R$_5$ each represents a hydrogen atom, R$_7$ and R$_8$ each represents a hydrogen atom; m is 0; and n is 1); or (2) a group represented by Formula A2:

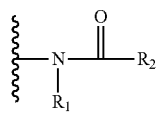

(in Formula A2, B and n are as defined in Formula A1; and R$_9$ represents a C1-C6 alkyl group).

6. The compound or a salt thereof according to claim 1, wherein the compound is selected from the following group of compounds:

(S)—N-(4-amino-6-methylene-5-(quinolin-3-yl)-7,8-dihydro-6H-pyrimido[5,4-b]pyrrolizin-7-yl)acrylamide;

(S)—N-(4-amino-6-methylene-5-(quinolin-3-yl)-7,8-dihydro-6H-pyrimido[5,4-b]pyrrolizin-7-yl)methacrylamide;

(S)—N-(4-amino-6-methylene-5-(quinolin-3-yl)-7,8-dihydro-6H-pyrimido[5,4-b]pyrrolizin-7-yl)but-2-enamide (mixture of E and Z);

(S,E)-N-(4-amino-6-methylene-5-(quinolin-3-yl)-7,8-dihydro-6H-pyrimido[5,4-b]pyrrolizin-7-yl)-4-(dimethylamino)but-2-enamide;

(S,E)-N-(4-amino-6-methylene-5-(quinolin-3-yl)-7,8-dihydro-6H-pyrimido[5,4-b]pyrrolizin-7-yl)-3-chloroacrylamide;

(S,Z)-N-(4-amino-6-methylene-5-(quinolin-3-yl)-7,8-dihydro-6H-pyrimido[5,4-b]pyrrolizin-7-yl)-3-chloroacrylamide;

(S,E)-N-(4-amino-6-methylene-5-(quinolin-3-yl)-7,8-dihydro-6H-pyrimido[5,4-b]pyrrolizin-7-yl)-4-(piperidin-1-yl)but-2-enamide;

(S)—N-(4-amino-6-methylene-5-(quinolin-3-yl)-7,8-dihydro-6H-pyrimido[5,4-b]pyrrolizin-7-yl)propiolamide;

(S)—N-(4-amino-6-methylene-5-(quinolin-3-yl)-7,8-dihydro-6H-pyrimido[5,4-b]pyrrolizin-7-yl)but-2-ynamide;

(S,E)-N-(4-amino-6-methylene-5-(quinolin-3-yl)-7,8-dihydro-6H-pyrimido[5,4-b]pyrrolizin-7-yl)-4-(diethylamino)but-2-enamide;

(S,E)-N-(4-amino-6-methylene-5-(quinolin-3-yl)-7,8-dihydro-6H-pyrimido[5,4-b]pyrrolizin-7-yl)-4-(ethyl(methyl)amino)but-2-enamide;

(S,E)-N-(4-amino-6-methylene-5-(quinolin-3-yl)-7,8-dihydro-6H-pyrimido[5,4-b]pyrrolizin-7-yl)-4-(isopropyl(methyl)amino)but-2-enamide;

(R)—N-(4-amino-6-methylene-5-(quinolin-3-yl)-6,7,8,9-tetrahydropyrimido[5,4-b]indolizin-7-yl)acrylamide;

(S)—N-(4-amino-6-methyl-5-(quinolin-3-yl)-8,9-dihydropyrimido[5,4-b]indolizin-8-yl)acrylamide;

(S)—N-(4-amino-6-methylene-5-(quinolin-3-yl)-6,7,8,9-tetrahydropyrimido[5,4-b]indolizin-8-yl)acrylamide;

(R)—N-(4-amino-6-methyl-5-(quinolin-3-yl)-8,9-dihydropyrimido[5,4-b]indolizin-8-yl)acrylamide;

(R)—N-(4-amino-6-methylene-5-(quinolin-3-yl)-6,7,8,9-tetrahydropyrimido[5,4-b]indolizin-8-yl)acrylamide;

(S)—N-(4-amino-6-methylene-5-(quinolin-3-yl)-7,8,9,10-tetrahydro-6H-pyrimido[5',4':4,5]pyrrolo[1,2-a]azepin-8-yl)acrylamide;

(S,E)-N-(4-amino-6-ethylidene-5-(quinolin-3-yl)-6,7,8,9-tetrahydropyrimido[5,4-b]indolizin-8-yl)acrylamide;

(S)—N-(4-amino-6-isopropyl-5-(quinolin-3-yl)-8,9-dihydropyrimido[5,4-b]indolizin-8-yl)acrylamide;

(S)—N-(4-amino-6-(propan-2-ylidene)-5-(quinolin-3-yl)-6,7,8,9-tetrahydropyrimido[5,4-b]indolizin-8-yl)acrylamide;

(R)—N-(4-amino-6-methylene-5-(quinolin-3-yl)-7,8-dihydro-6H-pyrimido[5,4-b]pyrrolizin-7-yl)-N-methylacrylamide;

(R)—N-(4-amino-6-methylene-5-(quinolin-3-yl)-6,7,8,9-tetrahydropyrimido[5,4-b]indolizin-8-yl)-N-methylacrylamide;

(R)—N-(4-amino-6-methyl-5-(quinolin-3-yl)-8,9-dihydropyrimido[5,4-b]indolizin-8-yl)-N-methylacrylamide;

(R)—N-(4-amino-6-methylene-5-(quinolin-3-yl)-7,8-dihydro-6H-pyrimido[5,4-b]pyrrolizin-7-yl)acrylamide;

(S)—N-(4-amino-6-methylene-5-(quinolin-3-yl)-7,8-dihydro-6H-pyrimido[5,4-b]pyrrolizin-7-yl)-N-methylacrylamide;

(S)—N-(4-amino-5-(quinolin-3-yl)-8,9-dihydropyrimido[5,4-b]indolizin-8-yl)acrylamide; and (R)—N-(4-amino-5-(quinolin-3-yl)-9,10-dihydro-8H-pyrimido[5',4':4,5]pyrrolo[1,2-a]azepin-8-yl)acrylamide.

7. The compound or a salt thereof according to claim 1, wherein the compound is selected from the following group of compounds:

(S)—N-(4-amino-6-methylene-5-(quinolin-3-yl)-7,8-dihydro-6H-pyrimido[5,4-b]pyrrolizin-7-yl)acrylamide;

(S,E)-N-(4-amino-6-methylene-5-(quinolin-3-yl)-7,8-dihydro-6H-pyrimido[5,4-b]pyrrolizin-7-yl)-3-chloroacrylamide;

(S,Z)-N-(4-amino-6-methylene-5-(quinolin-3-yl)-7,8-dihydro-6H-pyrimido[5,4-b]pyrrolizin-7-yl)-3-chloroacrylamide;

(S)—N-(4-amino-6-methyl-5-(quinolin-3-yl)-8,9-dihydropyrimido[5,4-b]indolizin-8-yl)acrylamide;

(S)—N-(4-amino-6-methylene-5-(quinolin-3-yl)-6,7,8,9-tetrahydropyrimido[5,4-b]indolizin-8-yl)acrylamide;

(S,E)-N-(4-amino-6-ethylidene-5-(quinolin-3-yl)-6,7,8,9-tetrahydropyrimido[5,4-b]indolizin-8-yl)acrylamide;

(R)—N-(4-amino-6-methylene-5-(quinolin-3-yl)-7,8-dihydro-6H-pyrimido[5,4-b]pyrrolizin-7-yl)-N-methylacrylamide;

(R)—N-(4-amino-6-methylene-5-(quinolin-3-yl)-6,7,8,9-tetrahydropyrimido[5,4-b]indolizin-8-yl)-N-methylacrylamide;

(R)—N-(4-amino-6-methyl-5-(quinolin-3-yl)-8,9-dihydropyrimido[5,4-b]indolizin-8-yl)-N-methylacrylamide; and (R)—N-(4-amino-5-(quinolin-3-yl)-9,10-dihydro-8H-pyrimido[5',4':4,5]pyrrolo[1,2-a]azepin-8-yl)acrylamide.

8. (S)—N-(4-amino-6-methylene-5-(quinolin-3-yl)-7,8-dihydro-6H-pyrimido[5,4-b]pyrrolizin-7-yl)acrylamide or a salt thereof.

9. (S)—N-(4-amino-6-methyl-5-(quinolin-3-yl)-8,9-dihydropyrimido[5,4-b]indolizin-8-yl)acrylamide or a salt thereof.

10. An EGFR inhibitor comprising the compound or a salt thereof according to claim 1, as an active ingredient.

11. A pharmaceutical composition comprising the compound or a salt thereof according to claim 1.

12. An antitumor agent comprising the compound or a salt thereof according to claim 1, as an active ingredient.

13. A method for inhibiting EGFR in a mammal in need thereof, the method comprising the step of administering, to the mammal, a compound or a salt thereof according to claim 1 at a dose effective for inhibiting EGFR, wherein said mammal has cancer.

14. A method for the manufacture of an antitumor agent, comprising combining the compound or a salt thereof according to claim 1 with a pharmaceutical carrier acceptable for use in an antitumor agent.

15. The compound or a salt thereof according to claim 1 for use in the prevention or treatment of cancer.

\* \* \* \* \*